US009919010B2

(12) United States Patent
Tamai et al.

(10) Patent No.: US 9,919,010 B2
(45) Date of Patent: Mar. 20, 2018

(54) METHOD FOR COLLECTING FUNCTIONAL CELLS IN VIVO WITH HIGH EFFICIENCY

(75) Inventors: Katsuto Tamai, Osaka (JP); Takehiko Yamazaki, Osaka (JP); Takenao Chino, Osaka (JP); Yasufumi Kaneda, Osaka (JP)

(73) Assignees: GENOMIX CO., LTD., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 12/990,086

(22) PCT Filed: Apr. 30, 2009

(86) PCT No.: PCT/JP2009/058525
§ 371 (c)(1),
(2), (4) Date: Jan. 4, 2011

(87) PCT Pub. No.: WO2009/133943
PCT Pub. Date: Nov. 5, 2009

(65) Prior Publication Data
US 2011/0104803 A1 May 5, 2011

(30) Foreign Application Priority Data
Apr. 30, 2008 (JP) .................. 2008-119355

(51) Int. Cl.
A61K 35/28 (2015.01)
C12N 5/0775 (2010.01)
A61K 35/12 (2015.01)

(52) U.S. Cl.
CPC ............ *A61K 35/28* (2013.01); *C12N 5/0663* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 3,896,810 A * | 7/1975 | Akiyama .................... 604/117 |
| 5,661,127 A | 8/1997 | Bhatnagar et al. |
| 5,851,986 A | 12/1998 | Takada et al. |
| 5,902,799 A * | 5/1999 | Herrmann et al. ............ 514/58 |
| 8,673,580 B2 | 3/2014 | Tamai et al. |
| 2002/0058019 A1* | 5/2002 | Berenson et al. ........... 424/93.7 |
| 2003/0003482 A1 | 1/2003 | Halle et al. |
| 2003/0060410 A1 | 3/2003 | Tracey et al. |
| 2004/0031072 A1 | 2/2004 | La Rosa et al. |
| 2004/0053841 A1 | 3/2004 | Tracey et al. |
| 2004/0191246 A1* | 9/2004 | Connelly et al. ........... 424/140.1 |
| 2004/0242481 A1 | 12/2004 | Bianchi et al. |
| 2004/0265971 A1 | 12/2004 | Sato et al. |
| 2005/0014255 A1* | 1/2005 | Tang et al. ..................... 435/366 |
| 2005/0260174 A1* | 11/2005 | Fraser ................ C12N 5/0667 424/93.7 |
| 2006/0035851 A1 | 2/2006 | Bianchi et al. |
| 2006/0111287 A1 | 5/2006 | Bianchi |
| 2006/0127373 A1 | 6/2006 | Son et al. |
| 2006/0281674 A1 | 12/2006 | Tessier et al. |
| 2007/0154529 A1 | 7/2007 | Bullerdiek |
| 2008/0214454 A1 | 9/2008 | Tracey et al. |
| 2009/0053277 A1 | 2/2009 | Nagaya et al. |
| 2009/0062187 A1 | 3/2009 | Bianchi et al. |
| 2009/0202500 A1 | 8/2009 | Tamai et al. |
| 2009/0280488 A1 | 11/2009 | Okazawa |
| 2011/0091928 A1 | 4/2011 | Tamai et al. |
| 2011/0097309 A1 | 4/2011 | Tamai et al. |
| 2011/0104803 A1* | 5/2011 | Tamai .................... A61K 35/28 435/378 |
| 2012/0251510 A1 | 10/2012 | Tamai et al. |

FOREIGN PATENT DOCUMENTS

| | | |
|---|---|---|
| AU | 2003/228099 A1 | 1/2004 |
| AU | 2004/203732 A1 | 7/2004 |
| CA | 2325226 | 5/2001 |
| CA | 2512512 A1 | 7/2004 |
| CA | 2 636 788 | 5/2008 |
| CN | 1516739 A | 7/2004 |
| CN | 1671742 A | 9/2005 |
| CN | 101374538 A | 2/2009 |
| CN | 102076350 A | 5/2011 |
| CN | 102443064 | 5/2012 |
| CN | 102711777 A | 10/2012 |
| EP | 0 791 601 A2 | 8/1997 |
| EP | 1 114 862 A2 | 7/2001 |
| EP | 1 459 759 A1 | 9/2004 |

(Continued)

OTHER PUBLICATIONS

Wu et al., Mesenchymal stem cells enhance wound healing through differentiation and angiogenesis; Stem Cells, vol. 10, pp. 2648-2659, 2007.*
Shing et al., Heparin Affinity: Purification of a Tumor-Derived Capillary Endothelial Cell Growth Factor; Science, vol. 223, pp. 1296-1299, 1984.*
Palumbo and Bianchi, High mobility box 1 protein, a cue for stem cell recruitment; Biochemical Pharmacology, vol. 68, No. 6, pp. 1165-1170, 2004.*
Kern et al., Comparative Analysis of Mesenchymal Stem Cells from Bone Marrow, Umbilical Cord Blood, or Adipose Tissue; Stem cells; vol. 24, pp. 1294-1301, 2006.*
Mouse care guidance from the Institutional Animal Care and Use Committee at University of California, San Franscisco; iacuc.ucsf.edu/Policies/BloodCollectionMice.doc; accessed May 15, 2014.*
Alden et al., "In Vivo Endochondral Bone Formation Using a Bone Morphogenetic Protein 2 Adenoviral Vector", *Human Gene Therapy*, 1999, vol. 10, No. 13, pp. 2245-2253.

(Continued)

*Primary Examiner* — Addison D Ault
(74) *Attorney, Agent, or Firm* — Saliwanchik, Lloyd & Eisenschenk

(57) ABSTRACT

Biologically low invasive vessels are filled with biological factors that have the activity of mobilizing specific functional cells in the body. The vessels are indwelled in the body. After specific functional cells are mobilized into the vessels, the vessels are removed from the body to collect functional cell populations mobilized to the vessels. Alternatively, the cells are directly collected from the vessels indwelled in the body.

27 Claims, 37 Drawing Sheets

(56) References Cited

FOREIGN PATENT DOCUMENTS

| | | |
|---|---|---|
| EP | 2 039 367 | 3/2009 |
| EP | 2055308 A1 | 5/2009 |
| EP | 2 284 255 A1 | 2/2011 |
| EP | 2 301 559 A1 | 3/2011 |
| JP | H9-227403 | 9/1997 |
| JP | 2001-321434 A | 11/2001 |
| JP | 2003-505506 A | 2/2003 |
| JP | 2005-508913 A | 4/2005 |
| JP | 2005-512507 | 5/2005 |
| JP | 2005-537253 A | 12/2005 |
| JP | 2006-124389 A | 5/2006 |
| JP | 2006-517537 A | 7/2006 |
| JP | 2006-523085 A | 10/2006 |
| JP | 2007-320919 | 12/2007 |
| JP | 2008-507505 A | 3/2008 |
| KR | 20090078304 A | 7/2009 |
| RU | 2005102593 A | 10/2005 |
| RU | 2 410 125 C2 | 1/2011 |
| WO | WO 01/08683 A1 | 2/2001 |
| WO | WO 02/074337 A1 | 9/2002 |
| WO | WO 02/088181 A2 | 11/2002 |
| WO | WO 02/092004 A2 | 11/2002 |
| WO | WO 03/043651 A1 | 5/2003 |
| WO | WO 2004/004763 A2 | 1/2004 |
| WO | WO 2004/004763 A3 | 1/2004 |
| WO | WO 2004/004770 A1 | 1/2004 |
| WO | WO 2004/044001 A2 | 5/2004 |
| WO | WO 2004/046345 A2 | 6/2004 |
| WO | WO 2004/061456 A2 | 7/2004 |
| WO | WO 2004/061456 A3 | 7/2004 |
| WO | WO 2005/025604 A2 | 3/2005 |
| WO | WO 2005/074984 A1 | 8/2005 |
| WO | WO 2006/008779 A1 | 1/2006 |
| WO | WO 2006/010628 A1 | 2/2006 |
| WO | WO 2006/024547 A2 | 3/2006 |
| WO | WO 2006/047820 A1 | 5/2006 |
| WO | WO 2006/077614 A1 | 7/2006 |
| WO | WO 2006/080434 A1 | 8/2006 |
| WO | WO 2006/100651 A1 | 9/2006 |
| WO | WO 2006/114805 A2 | 11/2006 |
| WO | WO 2007/015546 A1 | 2/2007 |
| WO | WO 2007/031100 A1 | 3/2007 |
| WO | WO 2007-130725 A | 11/2007 |
| WO | WO 2008/018641 A1 | 2/2008 |
| WO | WO 2008/053892 A1 | 5/2008 |
| WO | WO 2009/133939 | 11/2009 |
| WO | WO 2009/133940 | 11/2009 |
| WO | WO 2011/046570 | 4/2011 |
| WO | WO 2012/147470 A1 | 11/2012 |
| WO | WO 2014/065347 A1 | 5/2014 |

OTHER PUBLICATIONS

Bustin, "Regulation of DNA-Dependent Activities by the Functional Motifs of the High-Mobility-Group Chromosomal Proteins", *Molecular and Cellular Biology*, 1999, vol. 19, No. 8, pp. 5237-5246.

Charoonpatrapong et al., "HMGB1 Expression and Release by Bone Cells", *Journal of Cellular Physiology*, 2006, vol. 207, No. 2, pp. 480-490.

Chou et al., "Identity of nuclear high-mobility-group protein, HMG-1, and sulfoglucuronyl carbohydrate-binding protein, SPB-1, in brain", *Journal of Neurochemistry*, 2001, vol. 77, No. 1, pp. 120-131.

Degryse et al., "The High Mobility Group (HMG) Boxes of the Nuclear Protein HMG1 Induce Chemotaxis and Cytoskeleton Reorganization in Rat Smooth Muscle Cells", *The Journal of Cell Biology*, 2001, vol. 152, No. 6, pp. 1197-1206.

Delarosa et al., "Modulation of Adult Mesenchymal Stem Cells Activity by Toll-Like Receptors: Implications on Therapeutic Potential", *Mediators of Inflammation*, 2010, vol. 2010, Article ID: 865601, pp. 1-9.

Eckert et al., "S100 Proteins in the Epidermis", *The Journal of Investigative Dermatology*, 2004, vol. 123, No. 1, pp. 23-33.

Fujii et al., "Roles of Bone Morphogenetic Protein Type I Receptors and Smad Proteins in Osteoblast and Chondroblast Differentiation", *Molecular Biology of the Cell*, 1999, vol. 10, No. 11, pp. 3801-3813.

Germani et al., "Pivotal Advance: High-Mobility group box 1 protein—a cytokine with a role in cardiac repair", *Journal of Leukocyte Biology*, 2007, vol. 81, No. 1, pp. 41-45.

Granero-Molto et al., "Role of mesenchymal stem cells in regenerative medicine: application to bone and cartilage repair", *Expert Opinion on Biological Therapy*, 2008, vol. 8, No. 3, pp. 255-268.

Harris et al., "The nuclear protein HMGB1 as a proinflammatory mediator", *European Journal of Immunology*, 2004, vol. 34, No. 6, pp. 1503-1512.

Harris et al., "Alarmin(g) news about danger", *EMBO reports*, 2006, vol. 7, No. 8, pp. 774-778.

Hori et al., "The Receptor for Advanced Glycation End Products (RAGE) Is a Cellular Binding Site for Amphoterin", *The Journal of Biological Chemistry*, 1995, vol. 270, No. 43, pp. 25752-25761.

Jansen et al., "Transplantation of hematopoietic stem cells from the peripheral blood", *Journal of Cellular and Molecular Medicine*, 2005, vol. 9, No. 1, pp. 37-50.

Jayaraman et al., "High mobility group protein-1 (HMG-1) is a unique activator of p53", *Genes & Development*, 1998, Vo. 12, No. 4, pp. 462-472.

Jiang et al., "Pluripotency of mesenchymal stem cells derived from adult marrow", *Nature*, 2002, vol. 418, No. 6893, pp. 41-49.

Limana et al., "Exogenous High-Mobility Group Box 1 Protein Induces Myocardial Regeneration After Infarction via Enhanced Cardiac C-Kit $^+$Cell Proliferation and Differentiation", *Circulation Research*, 2005, Vo. 97, No. 8, pp. e73-e83.

Liotta et al., "Toll-Like Receptors 3 and 4 Are Expressed by Human Bone Marrow-Derived Mesenchymal Stem Cells and Can Inhibit Their T-Cell Modulatory Activity by Impairing Notch Signaling", *Stem Cells*, 2008, vol. 26, No. 1, pp. 279-289.

Meng et al., "HMGB1 induces migration of human bone marrow-derived mesenchymal stem cells", *Bull Acad. Mil. Med. Sci.*, 2006, vol. 30, No. 3, pp. 213-216. See English Translation.

Merenmies et al., "30-kDa Heparin-binding Protein of Brain (Amphoterin) Involved in Neurite Outgrowth", *The Journal of Biological Chemistry*, 1991, vol. 266, No. 25, pp. 16722-16729.

Müller et al., "The double life of HMGB-1 chromatin protein: architectural factor and extracellular signal", *The EMBO Journal*, 2001, vol. 20, No. 16, pp. 4337-4340.

Nakamura et al., "p38 Mitogen-Activated Protein Kinase Functionally Contributes to Chondrogenesis induced by Growth/Differentiation Factor-5 in ATDC5 Cells", *Experimental Cell Research*, vol. 250, No. 2, pp. 351-363.

Optiz et al., "Toll-like Receptor Engagement Enhances the Immunosuppressive Properties of Human Bone Marrow-Derived Mesenchymal Stem Cells by Inducing Indoleamine-2,3-dioxygenase-1 via Interferon-β and Protein Kinase R", *Stem Cells*, 2009, vol. 27, No. 4, pp. 909-919.

Otsuru et al., "BMP-2 mobilizes robust bone marrow mesenchymal progenitor cells to the circulating blood in bone regeneration", *The 28$^{th}$ Annual Meeting of the Molecular Biology Society of Japan*, Nov. 25, 2005, 733(3P-1012). See English Translation.

Palumbo et al., "Extracellular HMGB1, a signal of tissue damage, induces mesoangioblast migration and proliferation", *The Journal of Cell Biology*, 2004, vol. 164, No. 3, pp. 441-449.

Palumbo et al., "High mobility group box 1 protein, a cue for stem cell recruitment", *Biochemical Pharmacology*, 2004, vol. 68, No. 6, pp. 1165-1170.

Pevsner-Fischer et al., "Toll-like receptors and their ligands control mesenchymal stem cell functions", *Blood*, 2007, vol. 109, No. 4, pp. 1422-1432.

Raicevic et al., "Inflammation modifies the pattern and the function of Toll-like receptors expressed by human mesenchymal stromal cells", *Human Immunology*, 2010, vol. 71, No. 3, pp. 235-244.

Robinson et al., "The S100 Family Heterodimer, MRP-8/14, Binds with High Affinity to Heparin and Heparan Sulfate Glycosaminoglycans on Endothelial Cells", *The Journal of Biological Chemistry*, 2002, vol. 277, No. 5, pp. 3658-3665.

(56) References Cited

OTHER PUBLICATIONS

Ryckman et al., "Proinflammatory Activities of S100: Proteins S100A8, S100A9, and S100A8/A9 Induce Neutrophil Chemotaxis and Adhesion", *The Journal of Immunology*, 2003, vol. 170, No. 6, pp. 3233-3242.
Schäffer et al., "Wound Fluid Inhibits Wound Fibroblast Nitric Oxide Synthesis", *Journal of Surgical Research*, 2004, vol. 122, No. 1, pp. 43-48.
Shibata et al., "Fibroblast growth-stimulating activity of S100A9 (MRP-14)", *European Journal of Biochemistry*, 2004, vol. 271, No. 11, pp. 2137-2143.
Sun et al., "Isolation of Mouse Marrow Mesenchymal Progenitors by a Novel and Reliable Method", *Stem Cells*, 2003, vol. 21, No. 5, pp. 527-535.
Tagami et al., "Elevation of serum high-mobility group box 1 protein during granulocyte colony-stimulating factor-induced peripheral blood stem cell mobilisation", *British Journal of Haematology*, 2006, vol. 135, No. 4, pp. 567-569.
Tamai et al., "New Wave of Wound Healing", *Japanese Journal of Dermatology*, 2008, vol. 118, No. 4, pp. 645, #EL28-4. See English translation.
Tamai et al., U.S. Appl. No. 11/997,475, "Mesenchymal Stem Cell Inducer, Tissue Regeneration Promoter and Method of Preparing Mesenchymal Stem Cell", Filed Jan. 31, 2008, Now Abandoned.
Wang et al., "HMG-1 as a Late Mediator of Endotoxin Lethality in Mice", *Science*, 1999, vol. 285, No. 5425, pp. 248-251.
Wu et al., "Mesenchymal Stem Cells Enhance Wound Healing Through Differentiation and Agiogenesis", *Stem Cells*, 2007, vol. 25, No. 10, pp. 2648-2659.
Instruction Manual of HiTrap chelating HP (Amersham Biosciences), 2003, pp. 1-6.
Lonza BenchGuides, "Poietics Human Mesenchymal Stem Cells and Media hMSC", 2008, (Document # TS-PT-212-7 04/08).
Muhammad, Sajjad. et al. "The HMGBl Receptor Rage Mediates Ischemic Brain Damage," *The Journal of Neuroscience*, Nov. 12, 2008, vol. 28, No. 46, pp. 12023-12031.
Mistry, A.R. et al. "Recombinant HMG1 Protein Produced in Pichia Pastoris: A Nonviral Gene Delivery Agent" *BioTechniques*, 1997, vol. 22, pp. 718-729.
U.S. Appl. No. 13/503,329, filed Apr. 20, 2012 (Tamai et al.).
Uchida et al."The chemotactic activity of PDGF-bb, BMP-2, and FGF-2 towards committed and uncommitted mesenchymal stem cells", *The Journal of Japanese Orthopaedic Surgical Society*, 2005, vol. 79, No. 8, S832, 1-P6-6.
Vandal, Karen et al. "Blockade of S100A8 and S100A9 Suppresses Neutrophil Migration in Response to Lipopolysaccharide", *The Journal of Immunology*, Sep. 1, 2003, vol. 171, No. 5, pp. 2602-2609.
Wang, Huan Liang et al. "High mobility group protein B1 and the research progress of its biological effect", *Journal of Chinese Modern Surgery*, Dec. 31, 2006, vol. 3, No. 22, pp. 1806-1809.
Bittira et al., "Mobilization and homing of bone marrow stromal cells in myocardial infarction", *European Journal of Cardio-Thoracic Surgery*, Sep. 2003, vol. 24, No. 3, pp. 393-398.
Heil, Matthias et al., "An engineered heparin-binding form of VEGF-E (hbVEGF-E): Biological effects in vitro and mobilization of precursor cells", *Angiogenesis*, 2003, vol. 6, No. 3, pp. 201-211.
Kassis, I. et al., "Isolation of mesenchymal stem cells from G-CSF-mobilized human peripheral blood using fibrin microbeads", *Bone Marrow Transplantation*, May 2006, vol. 37, No. 10, pp. 967-976.
Laflamme et al. "Regenerating the heart", *Nature Biotechnology*, Jul. 2005, vol. 23, No. 7, pp. 845-856.
Lin, Siang-Yo et al., "The isolation of novel mesenchymal stromal cell chemotactic factors from the conditioned medium of tumor cells", *Experimental Cell Research*, 2008, vol. 314, No. 17, pp. 3107-3117.
Maruyama, "Inflammation and HMGB1/RAGE system", *Kekkan Igaku*, 2005, vol. 6, No. 5, pp. 519-525. See English translation.
Meng, Erhong et al., "High Mobility Group Box 1 Protein Inhibits the Proliferation of Human Mesenchymal Stem Cell and Promotes Their Migration and Differentiation along Osteoblastic Pathway", *Stem Cells and Development*, 2008, vol. 17, No. 4, pp. 805-814.
"Isolating culture and induced differentiation of marrow mesenchyma stem cells", *Principles and Protocols of Tissue Engineering*, Jun. 2004, pp. 277-278. See English Translation.
Ozaki, Yoshie et al., "Comprehensive Analysis of Chemotactic Factors for Bone Marrow Mesenchymal Stem Cells", *Stem Cells and Development*, Feb. 2007, vol. 16, No. 1, pp. 119-129.
Palumbo, Roberta et al., "Cells migrating to sites of tissue damage in response to the danger signal HMGB1 require NF-κB activation", *The Journal of Cell Biology*, Oct. 8, 2007, vol. 179, No. 1, pp. 33-40.
Pusterla, Tobias et al., "High mobility group B2 is secreted by myeloid cells and has mitogenic and chemoattractant activities similar to high mobility group B1", *Autoimmunity*, Apr. 2009, vol. 42, No. 4, pp. 308-310.
Sasaki, Mikako et al., "Mesenchymal Stem Cells Are Recruited into Wounded Skin and Contribute to Wound Repair by Transdifferentiation into Multiple Skin Cell Type[1] ", *The Journal of Immunology*, Feb. 15, 2008, vol. 180, No. 4, pp. 2581-2587.
Telusma et al., "Dendritic cell activating peptides induce distinct cytokine profiles", *International Immunology*, Nov. 2006, vol. 18, No. 11, pp. 1563-1573.
Kim, S. et al. "Skin Regeneration Using Keratinocytes and Dermal Fibroblasts Cultured on Biodegradable Microspherical Polymer Scaffolds" *Journal of Biomedical Materials Research Part : Applied Biomaterials*, Nov. 2005, vol. 75, No. 2, pp. 369-377.
Thorey, I. et al. "The $Ca^{2+}$-binding Proteins S100A8 and S100A9 are Encoded by Novel Injury-regulated Genes", *The Journal of Biological Chemistry*, Sep. 21, 2001, vol. 276, No. 38, pp. 35818-35825. (Epub Jul. 19, 2001).
Wang, Huating et al., "Theories and Technologies for Stem Cells," *Science Press*, Mar. 2005, vol. 5, p. 58-61.
Koc, On et al. "Mesenchymal Stem Cells: Heading into the Clinic," *Bone Marrow Transplantation*, 2001, vol. 27, No. 3, pp. 235-239.
Pittenger, Mark F. et al. "Multilineage Potential of Adult Human Mesenchymal Stem Cells," *Science*, 1999, vol. 284, No. 5411, pp. 143-147.
Wexler, Sarah A. et al. "Adult Bone Marrow is a Rich Source of Human Mesenchymal 'Stem' Cells but Umbilical Cord and Mobilized Adult Blood Are Not," *British Journal of Haematology*, 2003, vol. 121, No. 2, pp. 368-374.
Tamai et al. U.S. Appl. No. 14/114,395, "Peptide for Inducing Regeneration of Tissue and Uses Thereof," filed on Oct. 28, 2013, assigned to Genomix Co. Ltd. and Osaka University.
Hiratsuka, Sachie et al. "Tumour-mediated upregulation of chemoattractants and recruitment of myeloid cells predetermines lung metastasis," *Nature Cell Biology*, Dec. 2006; Epub Nov. 26, 2006; vol. 8 No. 12, pp. 1369-1375, Supplemental 1-7, Dec. 2006; *Epub* Nov. 26, 2006 (Nature Publishing Group).
Chen, Xiaoguang et al. "Human Bone Marrow Stromal Cell Cultures Conditioned by Traumatic Brain Tissue Extracts: Growth Factor Production," *Journal of Neuroscience Research*, 2002, 69:687-691.
Forte, Giancarlo et al. "Hepatocyte Growth Factor Effects on Mesenchymal Stem Cells: Proliferation, Migration, and Differentiation," *Stem Cells*, 2006, 24:23-33.
Huttunen, Henri J. et al. "Receptor for Advanced Glycation End Products-binding COOH-terminal Motif of Amphoterin Inhibits Invasive Migration and Metastasis," *Cancer Research*, 2002, 62:4805-4811.
La Rosa, TJ et al. "Glycine max protein SEQ ID No. 211221," Geneseq Accession No. AFQ20044, 2007.
Liu, Ke-Xin et al. "Human Placental Extract Stimulates Liver Regeneration in Rats," *Biological and Pharmaceutical Bulletin*, 1998, 21(1):44-49.
Mori, Taisuke et al. "Stem Cells/ ES cells—Mesenchymal Stem Cells—Human Bone Marrow Derived Mesenchymal Stem Cells," *Saisei Iryou—Regenerative Medicine*, 2005, 4(3); 421-9, 351.
Takami, Yoichiro et al. "Synergistic Induction of Hepatocyte Growth Factor in Human Skin Fibroblasts by the Inflammatory Cytokines Interleukin-1 and Interferon-γ," *Biochemical and Biophysical Research Communications*, 2005, 327:212-217.

(56) References Cited

OTHER PUBLICATIONS

Tatsumi, Ryuichi et al. HGF/SF Is Present in Normal Adult Skeletal Muscle and Is Capable of Activating Satellite Cells, 1998, *Developmental Biology*, 194:114-128.

Yuan, Yan et al. "Differentiation of Mesenchymal Stem Cells in Cardiomyogenic Cells Under the Induction of Myocardial Cell Lysate," *Chinese Journal of Cardiology*, 2005, 33(2):170-173.

Castro, Raymond F. et al., "Failure of Bone Marrow Cells to Transdifferentiate into Neural Cells in Vivo," *Science*, 2002, 297(5585):1299.

Chen, Y. et al., "Coaxing bone marrow stromal mesenchymal stem cells towards neuronal differentiation: progress and uncertainties," *Cellular and Molecular Life Sciences*, 2006, 63(14):1649-57.

Chopp, Michael et al., "Treatment of neural injury with narrow stromal cells," *The Lancet Neurology*, 2002, 1(2):92-100.

Gueukdjian, S.A. "Intra-Arterial Injections in the Treatment of Peripheral Vascular Disease," *Postgrad Medical Journal*, Jan. 1955, vol. 31, No. 351: 30-31.

Paul, S.R. et al., "Stromal Cell-Associated Hematopoiesis: Immortalization and Characterization of a Primate Bone Marrow-Derived Stromal Cell Line," *Blood*, 1991, 77(8):1723-33.

Schön et al. "Psoriasis," *The New England Journal of Medicine*, May 5, 2005, vol. 352, No. 18: 1899-1912.

Tagliafico, Enrico et al., "TGFβ/BMP activate the smooth muscle/bone differentiation programs in mesoangioblasts," *Journal of Cell Science*, 2004, 117(Pt 19):4377-88.

Tamai, Katsuto et al., "PDGFRα-positive cells in bone marrow are mobilized by high mobility group box 1 (HMGB1) to regenerate injured epithelia," *Proceedings of the National Academy of Sciences*, 2011, vol. 108, No. 16, p. 6609-6614. Epub Apr. 4, 2011.

Yang, De et al., "High mobility group box-1 protein induces the migration and activation of human dendritic cells and acts as an alarmin," *Journal of Leukocyte Biology*, 2007, 81(1):59-66. Epub Sep. 11, 2006.

Youn, Ju Ho et al., "High Mobility Group Box 1 Protein Binding to Lipopolysaccharide Facilitates Transfer of Lipopolysaccharide to CD14 and Enhances Lipopolysaccharide-Mediated TNF-α Production in Human Monocytes," *Journal of Immunology*, 2008, 180(7):5067-74.

Gudjonsson, Johann E. et al. "Psoriasis," *Fitzpatrick's Dermatology in General Medicine*, 8th edition, New York: Mc-Graw Hill Medical, 2012, p. 197-217.

Matsumoto, Kunio et al., "Up-Regulation of Hepatocyte Growth Factor Gene Expression by Interleukin-1 in Human Skin Fibrosis," *Biochemical and Biophysical Research Communications*, 1992, 188(1):235-243.

Popovic, Karin et al., "Increased Expression of the Novel Proinflammatory Cytokine High Mobility Group Box Chromosomal Protein 1 in Skin Lesions of Patients With Lupus Erythematosus," *Arthritis & Rheumatism*, 2005, 52(11):3639-3645.

Tamai, Katsuto et al.,"PDGFRα-positive cells in bone marrow are mobilized by high mobility group box 1 (HMGB1) to regenerate injured epithelia," http://www.pnas.org/content/suppl/2011/03/31/1016753108.DCSupplemental/pnas.201016753SI.pdf, Apr. 4, 2011.

Li, S. and Huang, L. "Millennium Review, Nonviral gene therapy: promises and challenges" *Gene Ther.* 7:31-34, 2000, Macmillan Publishers Ltd.

Somia, Nikunj and Verma, Inder M. "Reviews, Gene Therapy: Trials and Tribulations" *Nat. Rev. Genet.* 1(2):91-99, Nov. 2000), Macmillan Publishers Ltd.

Wang, Lei et al.: "Ischemic cerebral tissue and MCP-1 enhance rat bone marrow stromal cell migration in interface culture," *Experimental Hematology*, 2002, 30:831-836.

Yamada, Takayuki et al., "Regulation of osteoclast development by Notch signaling directed to osteoclast precursors and through stromal cells," *Blood*, Mar. 2003, 101(6):2227-2234.

Ehrchen, Jan M. et al. "The endogenous Toll-like receptor 4 agonist S100A8/S100A9 (calprotectin) as innate amplifier of infection, autoimmunity, and cancer," *Journal of Leukocyte Biology*, 2009, 86: 557-566.

Türker, Selcan et al. "Nasal route and drug delivery systems," *Pharmacy World and Science*, 2004, 26:137-142.

Li, Zihai et al., "Heat-Shock Proteins," *Current Protocols in Immunology*, 2003, Supplement 58, A.IT.1-A.IT.6.

Martin-Murphy, Brittany V. et al., "The Role of Damage Associated Molecular Pattern Molecules in Acetaminophen-Induced Liver Injury in Mice," *Toxicol Lett*, Feb. 2010, 192(3):1-20.

Panepucci, Rodrigo A. et al., "Abstract# 4427: Comparison of Gene Expression of Mesenchymal Stem Cells from the Umbilical Cord and from the Bone Marrow," *Blood*, Nov. 2003, 16(102):Abstract.

Pankov, Roumen et al., "Fibronectin at a glance," *J Cell Sci*, Oct. 2002, 115(20):3861-3863.

Santamaria-Kiseil, Liliana et al., "Calcium-dependent and -independent interactions of the S100 protein family," *Biochem J.*, 2006, 396:201-214.

Seong, Yong Seong et al., "Hydrophobicity: an ancient damage-associated molecular pattern that initiates innate immune responses," *Nature Reviews: Immunology*, Jun. 2004, 4(6):469-78.

Soo, Eliza T. L. et al., "Heat Shock Proteins as Novel Therapeutic Targets in Cancer," in vivo, 2008, 22(3):311-5.

Dong, Yingying et al., "HMGB1 Protein Does Not Mediate the Inflammatory Response in Spontaneous Spinal Cord Regeneration," *The Journal of Biological Chemistry*, Jun. 21, 2013, 288(25):18204-18218.

Kikuchi, Kiyoshi et al., "HMGB1 as a therapeutic target in spinal cord injury: A hypothesis for novel therapy development (Review)," *Experimental and Therapeutic Medicine*, 2011, 2:767-770.

Ulloa, Luis et al., "High-mobility group box 1 (HMGB1) protein: Friend and foe," *Cytokine & Growth Factor Reviews*, 2006, 17:189-201.

Venereau, Emilie et al., "Mutually exclusive redox forms of HMGB1 promote cell recruitment of proinflammatory cytokine release," *J. Exp. Med.*, 2012, 209(9):1519-1528.

De Souza, A.W.S. et al., "HMGB1 in Vascular Diseases: Its Role in Vascular Inflammation and Atherosclerosis," *Autoimmunity Reviews*, 2012, 11:909-917.

Zhou, Xiaoya et al., "Exogenous High-Mobility Group Box 1 Protein Injection Improves Cardiac Function after Myocardial Infarction: Involvement of Wnt Signaling Activation," *Journal of Biomedicine and Biotechnology*, 2012, vol. 2012, pp. 1-5.

Bianchi, M.E., "High mobility group 1 protein (HMGB1) N-terminal peptide." Geneseq Accession No. ADO80180, Aug. 12, 2004.

Bianchi, Marco E. et al., "The DNA binding site of HMG1 protein is composed of two similar segments (HMG boxes), both of which have counterparts in other eukaryotic regulatory proteins," *The EMBO Journal*, Mar. 1992, 11(3):1055-1063.

Gong, Wei et al., "The Anti-Inflammatory Activity of HMGB1 a Box is Enhanced When Fused with C-Terminal Acidic Tail," *Journal of Biomedicine and Biotechnology*, vol. 2010, Article ID 915234, 6 pages, 2-10. Doi:10.1155/2010/915234.

Herrera, M.B., et al., "Exogenous mesenchymal stem cells localize to the kidney by means of CD44 following acute tubular injury," *Kidney International*, 2007; 72:430-441.

Tang, Daolin, et al., "High-Mobility Group Box 1, Oxidative Stress, and Disease," *Antioxidants & Redox Signaling*, 2011; 14(7): 1315-1335. DOI: 10.1089/ars.2010.3356.

Woodbury, Dale et al., "Adult Rat and Human Bone Marrow Stromal Cells Differentiate Into Neurons," *Journal of Neuroscience Research*, Aug. 15, 2000; 61(4):364-370.

Tamai, Katsuto et al. U.S. Appl. No. 14/436,906, "Novel Method for Treating Cardiac Infarction Using HMGBI Fragment," filed on Apr. 20, 2015, and assigned to Genomix Co., Ltd. and Osaka University.

Tamai, Katsuto et al. U.S. Appl. No. 14/436,920, "Novel Method for Treating Spinal Cord Injury Using HMGB1 Fragment," filed on Apr. 20, 2015, assigned to Genomix Co., Ltd. and Osaka University.

Mansbridge, Jonathan, "Skin Tissue Engineering," *J. Biomater. Sci. Polymer Ed.*, Aug. 1, 2008, 19(8):955-968.

Chamberlain, Giselle et al., "Concise Review: Mesenchymal Stem Cells: Their Phenotype, Differentiation Capacity, Immunological Features, and Potential for Homing," *Stem Cells* 2007; 25:2739-2749.

Kessler, Michael W. et al., "Tissue Engineering and Cartilage," *Organogenesis*, Jan. 2008; 4(1):28-32.

(56) References Cited

OTHER PUBLICATIONS

Lanza, Robert et al., and Arnold Caplan, "Essentials of Stem Cell Biology—Chapter 27, Mesenchymal Stem Cells," *Elsevier Academic Press*, 2006, pp. 205-210.

Morosetti, R., et al., "MyoD expression restores defective myogenic differentiation of human mesoangioblasts from inclusion-body myositis muscle." *PNAS*, Nov. 7, 2006, 103(45): 16995-17000.

Esposito, E., et al., "Melatonin reduces stress-activated/mitogen-activated protein kinases in spinal cord injury." *J. Pineal Res.*, 2009, 46: 79-86.

Healthwise Staff, "Age-related Macular Degeneration." *University of Michigan Health System*, Aug. 2015, https://www.uofmhealth.org/health-library/hw176039.

Jiao, C., et al., "Researchers find nerve damage may precede diabetic retinopathy." *EurekAlert! Science News*, Apr. 2016, https://www.eurekalert.org/pub_releases/2016-04/uoih-rfv042616.php.

Kawabata, H., et al., "High Mobility Group Box 1 Is Upregulated After Spinal Cord Injury and Is Associated With Neuronal Cell Apoptosis." *Spine*, 2010, 35(11): 1109-1115.

Slater, M., et al., "Endometriotic cells exhibit metaplastic change and oxidative DNA damage as well as decreased function, compared to normal endometrium." *Journal of Molecular Histology*, 2005, 36(4): 257-263.

Wolf, G., et al., "From the Periphery of the Glomerular Capillary Wall Toward the Center of Disease." *Diabetes*, Jun. 2005, 54(6): 1626-1634.

Cole, John Sterling, "Pharmacologic Mobilization of Mesenchymal Stem Cells for Enhanced Bone Formation," *Colby College, Rush University*, 2009; UMI No. 1466383, pp. 1-82.

Kirov, Sergei A. et al., "In Vivo 2-Photon Microscopy Reveals G-CSF Enhanced Mobilization and Targeting of Neo-Endogenous Bone Marrow Stromal Cells to Stroke Injury Sites," *Stroke*, Apr. 2009, 40(4):1-2, e133, Abstract No. 107.

Straino, Stefania et al., "High-Mobility Group Box 1 Protein in Human and Murine Skin: Involvement in Wound Healing," *Journal of Investigative Dermatology*, 2008, 128:1545-1553.

Basso, D. Michelle et al., "Basso Mouse Scale for Locomotion Detects Differences in Recovery after Spinal Cord Injury in Five Common Mouse Strains," *Journal of Neurotrauma*, 2006, 23(5):635-659.

Fang, Ping et al., "HMGB1 Contributes to Regeneration After Spinal Cord Injury in Adult Zebrafish," *Mol Neurobiol*, 2014, 49:472-483.

Kitahara, Tatsuro et al., "High-Mobility Group Box 1 Restores Cardiac Function After Myocardial Infarcation in Transgenic Mice", *Cardiovascular Research, European Society of Cardiology*, Oct. 1, 2008, 80:40-46.

Kohno, Takashi et al., "High Mobility Group Box 1 Protein is Associated With Post-Infarction Healing Process and Left Ventricular Remodeling", *Circ. J.*, 2008, 72 Supplement 1, PJ-004:510-511.

Nakajima et al., "Dynamics and Role of High Mobility Group Box-1 (HMGB-1) in Injured Spinal Cord," *Nihon Seikei Geka Gakkai Zasshi (J. Jpn. Orthop. Assoc.)*, 2010, 84(8):S1050.

Quertainmont, Renaud et al., "Mesenchymal Stem Cell Graft Improves Recovery after Spinal Cord Injury in Adult Rats through Neurotrophic and Pro-Angiogenic Actions," *PLoS ONE*, Jun. 2012, 7(6):1-15.

Rahimi-Movaghar, Vafa, "Effect of Decompression on Complete Spinal Cord Injury in Rats," *International Journal of Neuroscience*, 2008, 118:1359-1373.

Takahashi, Kunihiko et al., "Effects of HMGB1 on PostInfarction Chronic Heart Failure—Novel Mechanism Regarding Therapeutic Effects of Cell Therapy", *Supplement*, 2011, 27 I-E-19:S189.

Takeishi, Yasuchika et al., "Importance of Inflammation and Immune Response in Heart Failure—Toll-Like Receptor-Mediated Signaling Pathway and Ventricular Remodeling After Myocardial Infarction", *Journal of Clinical and Experimental Medicine*, Jan. 30, 2010, 232(5):378-385.

Tamai, Katsuto et al., "Development and Outlook of Internal Regeneration-Inducing Pharmaceuticals that use in vivo Bone Marrow Mesenchymal Stem / Progenitor Cell-Mobilizing Factors", *Gene & Medicine MOOK*, Jul. 22, 2012, pp. 207-212.

Arminan, Ana et al., "Mesenchymal Stem Cells Provide Better Results Than Hematopoietic Precursors for the Treatment of Myocardial Infarction." *JACC*, May 18, 2010, 55(20): 2244-2253.

Berry, Mark F., et al., "Mesenchymal stem cell injection after myocardial infarction improves myocardial compliance." *Am J Physiol Heart Circ Physiol*, Jun. 2006, 290(6): H2196-H2203.

HMGBIOTECH SRL , "BoxA from HMGB1, human & mouse LPS-free." [online]., pp. 1-2, 2008-2017 [retrieved on Jan. 27, 2017]. Retrieved from the Internet: <URL: http://www.hmgbiotech.com/products.php?ID=91>.

HMGBIOTECH SRL , "BoxA from HMGB1, human & mouse LPS-free. Datasheet" [online]. pp. 1, 2008 [retrieved on Jan. 31, 2017]. Retrieved from the Internet: <URL: http://www.hmgbiotech.com/upload/documenti/0515122144_boxa>.

Ishikane, Shin, "Therapeutic application of allogenic fetal membrane-derived mesenchymal stem cells transplantation in regenerative medicine." *Pharmaceutical Bulletin of Fukuoka University*, Mar. 2011, 11(0): 17-25.

Li, Ying et al., "Advancement of Human Multiply, Sex health and Reproductive Medical Science." *Peking University Medical Press*, Mar. 2007, 1$^{st}$ Edition, 270-271.

Takahashi, Kunihiko, et al., "Modulated Inflammation by Injection of High-Mobility Group Box 1 Recovers Post-Infarction Chronically Failing Heart." *Circulation*, Sep. 2008, 118(14 Suppl): S106-S114.

Wang, Wei et al., "Intravenous administration of bone marrow mesenchymal stromal cells is safe for the lung in a chronic myocardial infarction model," *Regen Med*, Mar. 2011, 6(2): 179-190.

Wang, Yaping, "Biology of hematopoietic stem cell and the research method thereof." *Science Press*, Mar. 2007, 1st Edition, 56-58.

Tamai, K. et al., U.S. Appl. No. 15/691,017, "Peptide for Inducing Regeneration of Tissue and Uses Thereof." filed Aug. 30, 2017.

Panepucci, Rodrigo A., et al., "Comparison of Gene Expression of Umbilical Cord Vein and Bone Marrow-Derived Mesenchymal Stem Cells." Stem Cells, Dec. 2004, 22(7): 1263-1278.

\* cited by examiner

BONE DIFFERENTIATION
INDUCING MEDIUM

ALIZARIN RED STAIN

ADIPOCYTE DIFFERENTIATION INDUCING MEDIUM

OIL RED STAIN

CONTROL MOUSE HEART MOUSE SKIN

CONTROL MOUSE BRAIN MOUSE SKIN

S100A8  S100A9

S100A8

14 15 16 17 18 19 20 21 22 23 24 25 26 M 27 28 29 30 31 32 33 34 35 36 37 38 39 40

S100A9

14 15 16 17 18 19 20 21 22 23 24 25 26 M 27 28 29 30 31 32 33 34 35 36 37 38 39 40

SEQUENCE LISTING

<160> NUMBER OF SEQ ID NOS: 32

<210> SEQ ID NO 1
<211> LENGTH: 215
<212> TYPE: PRT
<213> ORGANISM: Homo sapiens

<400> SEQUENCE: 1

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215
```

<210> SEQ ID NO 2
<211> LENGTH: 648
<212> TYPE: DNA
<213> ORGANISM: Homo sapiens

<400> SEQUENCE: 2

```
atgggcaaag gagatcctaa gaagccgaga ggcaaaatgt catcatatgc atttttgtg      60 caaacttgtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaagcgga caaggcccgt tatgaaagag aaatgaaaac ctatatccct    240
cccaaagggg agacaaaaaa gaagttcaag gatcccaatg cacccaagag gcctccttcg    300
gccttcttcc tcttctgctc tgagtatcgc ccaaaaatca aggagaaca tcctggcctg    360 tccattggtg atgttgcgaa gaaactggga gagatgtgga ataacactgc tgcagatgac    420
aagcagcctt atgaaaagaa ggctgcgaag ctgaaggaaa atacgaaaa ggatattgct    480 gcatatcgag ctaaaggaaa gcctgatgca gcaaaaaagg gagttgtcaa ggctgaaaaa    540
agcaagaaaa agaaggaaga ggaggaagat gaggaagatg aagaggatga ggaggaggag    600
```

```
gaagatgaag aagatgaaga tgaagaagaa gatgatgatg atgaataa                  648
```

```
<210> SEQ ID NO 3
<211> LENGTH: 215
<212> TYPE: PRT
<213> ORGANISM: Mus musculus

<400> SEQUENCE: 3
```

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Asp Glu Asp Glu
        195                 200                 205

Glu Glu Asp Asp Asp Asp Glu
        210                 215

```
<210> SEQ ID NO 4
<211> LENGTH: 648
<212> TYPE: DNA
<213> ORGANISM: Mus musculus

<400> SEQUENCE: 4
```

```
atgggcaaag gagatcctaa aaagccgaga ggcaaaatgt cctcatatgc attctttgtg     60
caaacttgcc gggaggagca agaagaag caccccgatg cttctgtcaa cttctcagag      120
ttctccaaga gtgctcaga gaggtggaag accatgtctg ctaaagaaaa ggggaaattt     180
gaagatatgg caaaggctga caaggctcgt tatgaaagag aaatgaaaac ctacatcccc     240
cccaaagggg agaccaaaaa gaagttcaag accccaatg cacccaagag gcctccttcg     300
gccttcttct tgttctgttc tgagtaccgc cccaaaatca aggcgagca tcctggctta      360 tccattggtg atgttgcaaa gaaactagga gagatgtgga acaacactgc agcagatgac     420
aagcagccct atgagaagaa agctgccaag ctgaaggaga gtatgagaa ggatattgct      480 gcctacagag ctaaaggaaa acctgatgca gcgaaaaagg gggtggtcaa ggctgaaaag     540
```
agcaagaaaa agaaggaaga ggaagatgat gaggaggatg aagaggatga ggaagaggag    600
gaagaagagg aagacgaaga tgaagaagaa gatgatgatg atgaataa                 648

<210> SEQ ID NO 5
<211> LENGTH: 215
<212> TYPE: PRT
<213> ORGANISM: Rattus norvegicus

<400> SEQUENCE: 5

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Asp Glu Glu
            180                 185                 190

Asp Glu Glu Asp Glu Glu Glu Glu Glu Glu Glu Asp Glu Asp Glu
        195                 200                 205

Glu Glu Asp Asp Asp Asp Glu
        210                 215

<210> SEQ ID NO 6
<211> LENGTH: 648
<212> TYPE: DNA
<213> ORGANISM: Rattus norvegicus

<400> SEQUENCE: 6
atgggcaaag gagatcctaa gaagccgaga ggcaaaatgt cctcatatgc attctttgtg    60
caaacctgcc gggaggagca caagaagaag cacccggatg cttctgtcaa cttctcagag   120
ttctccaaga agtgctcaga gaggtggaag accatgtctg ctaaagaaaa ggggaaattt   180
gaagatatgg caaaggctga caaggctcgt tatgaaagag aaatgaaaac ctacatcccc   240
cccaaagggg agaccaaaaa gaagttcaag accccaatg cccccaagag gcctccttcg   300
gccttcttct tgttctgttc tgagtaccgc ccaaaaatca aggcgagca tcctggctta   360 tccattggtg atgttgcgaa gaaactagga gagatgtgga acaacactgc tgcggatgac   420
aagcagccct atgaaaagaa ggccgccaag ctgaaggaga gtatgagaa ggatattgct   480 gcctacagag ctaaaggaaa acctgatgca gcgaaaaagg gggtggtcaa ggctgagaag   540

```
agcaagaaaa agaaggaaga ggaagacgac gaggaggatg aagaggatga ggaagaggag    600
gaagaggagg aagacgaaga tgaagaagaa gatgatgatg atgaataa                 648
```

<210> SEQ ID NO 7
<211> LENGTH: 209
<212> TYPE: PRT
<213> ORGANISM: Homo sapiens

<400> SEQUENCE: 7

```
Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Asp Glu Asp Glu Glu Glu Asp Glu Asp
        195                 200                 205

Glu
```

<210> SEQ ID NO 8
<211> LENGTH: 630
<212> TYPE: DNA
<213> ORGANISM: Homo sapiens

<400> SEQUENCE: 8

```
atgggtaaag gagaccccaa caagccgcgg ggcaaaatgt cctcgtacgc cttcttcgtg    60
cagacctgcc gggaagagca caagaagaaa cacccggact cttccgtcaa tttcgcggaa   120
ttctccaaga agtgttcgga gagatggaag accatgtctg caaaggagaa gtcgaagttt   180
gaagatatgg caaaaagtga caaagctcgc tatgacaggg agatgaaaaa ttacgttcct   240
cccaaaggtg ataagaaggg gaagaaaaag accccaatg ctcctaaaag gccaccatct   300
gccttcttcc tgtttttgctc tgaacatcgc ccaaagatca aaagtgaaca ccctggccta   360
tccattgggg atactgcaaa gaaattgggt gaaatgtggt ctgagcagtc agccaaagat   420
aaacaaccat atgaacagaa agcagctaag ctaaggagaa atatgaaaaa ggatattgct   480
gcatatcgtg ccaagggcaa aagtgaagca ggaaagaagg gccctggcag gccaacaggc   540
```

```
tcaaagaaga agaacgaacc agaagatgag gaggaggagg aggaagaaga agatgaagat      600
gaggaggaag aggatgaaga tgaagaataa                                      630
```

<210> SEQ ID NO 9
<211> LENGTH: 210
<212> TYPE: PRT
<213> ORGANISM: Mus musculus

<400> SEQUENCE: 9

```
Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ser Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Leu Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Lys Asp Pro Asn Ala Pro Lys
                85                  90                  95

Arg Pro Pro Ser Ala Phe Phe Leu Phe Cys Ser Glu Asn Arg Pro Lys
            100                 105                 110

Ile Lys Ile Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
            180                 185                 190

Glu Glu Glu Glu Glu Glu Glu Glu Asp Glu Glu Glu Glu Asp
        195                 200                 205

Glu Glu
    210
```

<210> SEQ ID NO 10
<211> LENGTH: 633
<212> TYPE: DNA
<213> ORGANISM: Mus musculus

<400> SEQUENCE: 10

```
atgggcaagg gtgaccccaa caagccgcgg ggcaaaatgt cctcgtacgc cttcttcgtg       60
cagacctgcc gcgaggagca caagaagaag catcccgact cgtcggtgaa cttcgccgag      120
ttctccaaga atgctccga gagatggaag accatgtctg caaggaaaa gtccaagttt       180 gaagatttgg ccaagagcga caaagctcgt tatgacaggg agatgaagaa ctatgttcct      240
cccaaagggg ataagaaagg aaagaaaaaa gaccccaatg ctccgaagag accaccgtct      300
gccttcttcc tgtttttgctc tgaaaatcgc ccaaagatca aaattgaaca cccaggcctg      360
tctattggag atactgcgaa gaaactgggt gagatgtggt ctgagcaatc tgccaaagat      420
aaacaaccgt atgagcagaa agcagctaaa ctaaaggaga agtatgaaaa ggatattgct      480
```

| | |
|---|---:|
| gcataccgtg ccaagggcaa aagtgaagca ggaaagaagg gtcctggtag gccaacaggc | 540 |
| tcaaagaaga agaacgaacc agaagatgag gaggaggaag agaggagga agaggaggaa | 600 |
| gatgacgagg aagaagagga ggatgaagaa taa | 633 |

<210> SEQ ID NO 11
<211> LENGTH: 210
<212> TYPE: PRT
<213> ORGANISM: Rattus norvegicus

<400> SEQUENCE: 11

Met Gly Lys Gly Asp Pro Asn Lys Pro Arg Gly Lys Met Ser Ser Tyr
1               5                   10                  15
Ala Phe Phe Val Gln Thr Cys Arg Glu Glu His Lys Lys Lys His Pro
            20                  25                  30
Asp Ser Ser Val Asn Phe Ala Glu Phe Ser Lys Lys Cys Ser Glu Arg
        35                  40                  45
Trp Lys Thr Met Ser Ala Lys Glu Lys Ser Lys Phe Glu Asp Leu Ala
    50                  55                  60
Lys Ser Asp Lys Ala Arg Tyr Asp Arg Glu Met Lys Asn Tyr Val Pro
65                  70                  75                  80
Pro Lys Gly Asp Lys Lys Gly Lys Lys Lys Asp Pro Asn Ala Pro Lys
                85                  90                  95
Arg Pro Pro Ser Ala Phe Phe Leu Phe Cys Ser Glu His Arg Pro Lys
            100                 105                 110
Ile Lys Ser Glu His Pro Gly Leu Ser Ile Gly Asp Thr Ala Lys Lys
        115                 120                 125
Leu Gly Glu Met Trp Ser Glu Gln Ser Ala Lys Asp Lys Gln Pro Tyr
    130                 135                 140
Glu Gln Lys Ala Ala Lys Leu Lys Glu Lys Tyr Glu Lys Asp Ile Ala
145                 150                 155                 160
Ala Tyr Arg Ala Lys Gly Lys Ser Glu Val Gly Lys Lys Gly Pro Gly
                165                 170                 175
Arg Pro Thr Gly Ser Lys Lys Lys Asn Glu Pro Glu Asp Glu Glu Glu
            180                 185                 190
Glu Glu Glu Glu Glu Asp Asp Glu Asp Glu Glu Glu Asp Glu Asp
        195                 200                 205
Glu Glu
    210

<210> SEQ ID NO 12
<211> LENGTH: 633
<212> TYPE: DNA
<213> ORGANISM: Rattus norvegicus

<400> SEQUENCE: 12

| | |
|---|---:|
| atgggcaagg gggaccccaa caagccgcgg ggcaagatgt cctcgtacgc cttcttcgtg | 60 |
| cagacctgcc gggaggagca agaagaag catcccgact cgtcggtcaa cttcgccgag | 120 |
| ttctcgaaga atgttcgga gagatggaag accatgtctg ccaaggaaaa gtcgaagttt | 180 |
| gaggatttgg ccaagagcga caaagctcgt tatgacaggg agatgaagaa ctatgttcct | 240 |
| cccaaaggtg ataagaaagg aaagaaaaaa gatccaaatg ctcccaagag accaccgtct | 300 |
| gccttcttcc tgttttgctc tgaacatcgc ccaaagatca aagtgaaca ccccggcctg | 360 |
| tctattggag atactgcaaa gaaactgggg gagatgtggt ctgagcaatc tgccaaagat | 420 |
| aaacaaccgt atgagcagaa agcagctaaa ctaaaggaga gtatgaaaa ggatattgct | 480 |

```
gcataccgtg ccaagggcaa aagtgaagta ggaaagaagg gtcctggtag gccaacaggc    540
tcaaagaaga agaatgaacc agaagatgag gaagaggagg aggaggaaga agatgatgaa    600
gatgaagagg aggaagatga ggatgaagaa taa                                 633
```

<210> SEQ ID NO 13
<211> LENGTH: 200
<212> TYPE: PRT
<213> ORGANISM: Homo sapiens

<400> SEQUENCE: 13

```
Met Ala Lys Gly Asp Pro Lys Lys Pro Lys Gly Lys Met Ser Ala Tyr
1               5                   10                  15

Ala Phe Phe Val Gln Thr Cys Arg Glu Glu His Lys Lys Lys Asn Pro
            20                  25                  30

Glu Val Pro Val Asn Phe Ala Glu Phe Ser Lys Lys Cys Ser Glu Arg
        35                  40                  45

Trp Lys Thr Met Ser Gly Lys Glu Lys Ser Lys Phe Asp Glu Met Ala
50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Lys Leu Gly
        115                 120                 125

Glu Met Trp Asn Asn Leu Asn Asp Ser Glu Lys Gln Pro Tyr Ile Thr
130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Asp Glu Glu Glu Glu Glu Glu Glu Glu
            180                 185                 190

Glu Glu Glu Glu Glu Glu Asp Glu
        195                 200
```

<210> SEQ ID NO 14
<211> LENGTH: 603
<212> TYPE: DNA
<213> ORGANISM: Homo sapiens

<400> SEQUENCE: 14

```
atggctaaag gtgaccccaa gaaaccaaag gcaagatgt ccgcttatgc cttctttgtg     60
cagacatgca gagaagaaca taagaagaaa acccagagg tccctgtcaa ttttgcggaa    120
ttttccaaga agtgctctga gaggtggaag acgatgtccg ggaaagagaa atctaaattt    180
gatgaaatgg caaaggcaga taaagtgcgc tatgatcggg aaatgaagga ttatggacca    240
gctaagggag caagaagaa gaggatcct aatgctccca aaaggccacc gtctggattc    300
ttcctgttct gttcagaatt ccgccccaag atcaaatcca aaccccgg catctctatt    360 ggagacgtgg caaaaaagct gggtgagatg tggaataatt taaatgacag tgaaaagcag    420
ccttacatca ctaaggcggc aaagctgaag gagaagtatg agaaggatgt tgctgactat    480
aagtcgaaag gaaagtttga tggtgcaaag ggtcctgcta agttgcccg gaaaaaggtg    540
```

```
gaagaggaag atgaagaaga ggaggaggaa gaagaggagg aggaggagga ggaggatgaa    600
taa                                                                  603
```

<210> SEQ ID NO 15
<211> LENGTH: 200
<212> TYPE: PRT
<213> ORGANISM: Mus musculus

<400> SEQUENCE: 15

```
Met Ala Lys Gly Asp Pro Lys Pro Lys Gly Lys Met Ser Ala Tyr
1               5                   10                  15

Ala Phe Phe Val Gln Thr Cys Arg Glu Glu His Lys Lys Lys Asn Pro
            20                  25                  30

Glu Val Pro Val Asn Phe Ala Glu Phe Ser Lys Lys Cys Ser Glu Arg
        35                  40                  45

Trp Lys Thr Met Ser Ser Lys Glu Lys Ser Lys Phe Asp Glu Met Ala
    50                  55                  60

Lys Ala Asp Lys Val Arg Tyr Asp Arg Glu Met Lys Asp Tyr Gly Pro
65                  70                  75                  80

Ala Lys Gly Gly Lys Lys Lys Asp Pro Asn Ala Pro Lys Arg Pro
                85                  90                  95

Pro Ser Gly Phe Phe Leu Phe Cys Ser Glu Phe Arg Pro Lys Ile Lys
            100                 105                 110

Ser Thr Asn Pro Gly Ile Ser Ile Gly Asp Val Ala Lys Lys Leu Gly
        115                 120                 125

Glu Met Trp Asn Asn Leu Ser Asp Asn Glu Lys Gln Pro Tyr Val Thr
    130                 135                 140

Lys Ala Ala Lys Leu Lys Glu Lys Tyr Glu Lys Asp Val Ala Asp Tyr
145                 150                 155                 160

Lys Ser Lys Gly Lys Phe Asp Gly Ala Lys Gly Pro Ala Lys Val Ala
                165                 170                 175

Arg Lys Lys Val Glu Glu Glu Glu Glu Glu Glu Glu Glu Glu Glu Glu
            180                 185                 190

Glu Glu Glu Glu Glu Glu Asp Glu
        195                 200
```

<210> SEQ ID NO 16
<211> LENGTH: 603
<212> TYPE: DNA
<213> ORGANISM: Mus musculus

<400> SEQUENCE: 16

```
atggctaaag gtgaccccaa gaaaccaaag ggcaagatgt ctgcttatgc cttctttgtg     60
cagacatgca gggaagaaca taagaagaaa aacccagagg ttcccgtcaa ttttgctgag   120
ttctccaaga agtgctcgga gaggtggaag accatgtcta gcaaagagaa atcaaagttt   180
gatgaaatgg caaaggcaga taaagtccga tatgatcggg agatgaaaga ttatggacca   240
gctaaaggag gcaagaagaa gaaggaccca aatgccccca aaagacctcc gtctggattt   300
ttcttattct gctctgaatt ccgccccaag atcaaatcca caaccctgg catctccatt   360 ggagatgtgg caaaaaagct gggtgagatg tggaataact taagtgacaa tgaaaagcag   420
ccttatgtca ccaaggcagc aaagctgaag gagaagtatg agaaggatgt tgctgactat   480
aagtctaaag ggaagtttga tggtgccaag ggtcctgcta agttgcccg gaaaaagtg   540 gaagaagagg aagaggagga ggaagaggaa gaagaggagg aggaagagga ggaagatgaa   600
``` taa                                                                                           603

<210> SEQ ID NO 17
<211> LENGTH: 89
<212> TYPE: PRT
<213> ORGANISM: Mus musculus

<400> SEQUENCE: 17

Met Pro Ser Glu Leu Glu Lys Ala Leu Ser Asn Leu Ile Asp Val Tyr
1               5                   10                  15

His Asn Tyr Ser Asn Ile Gln Gly Asn His His Ala Leu Tyr Lys Asn
            20                  25                  30

Asp Phe Lys Lys Met Val Thr Thr Glu Cys Pro Gln Phe Val Gln Asn
        35                  40                  45

Ile Asn Ile Glu Asn Leu Phe Arg Glu Leu Asp Ile Asn Ser Asp Asn
    50                  55                  60

Ala Ile Asn Phe Glu Glu Phe Leu Ala Met Val Ile Lys Val Gly Val
65                  70                  75                  80

Ala Ser His Lys Asp Ser His Lys Glu
                85

<210> SEQ ID NO 18
<211> LENGTH: 270
<212> TYPE: DNA
<213> ORGANISM: Mus musculus

<400> SEQUENCE: 18
atgccgtctg aactggagaa ggccttgagc aacctcattg atgtctacca caattattcc      60
aatatacaag gaaatcacca tgccctctac aagaatgact tcaagaaaat ggtcactact     120
gagtgtcctc agtttgtgca gaatataaat atcgaaaact tgttcagaga attggacatc     180
aatagtgaca atgcaattaa cttcgaggag ttccttgcga tggtgataaa agtgggtgtg     240
gcatctcaca agacagcca caaggagtag                                         270

<210> SEQ ID NO 19
<211> LENGTH: 89
<212> TYPE: PRT
<213> ORGANISM: Rattus norvegicus

<400> SEQUENCE: 19

Met Ala Thr Glu Leu Glu Lys Ala Leu Ser Asn Val Ile Glu Val Tyr
1               5                   10                  15

His Asn Tyr Ser Gly Ile Lys Gly Asn His His Ala Leu Tyr Arg Asp
            20                  25                  30

Asp Phe Arg Lys Met Val Thr Thr Glu Cys Pro Gln Phe Val Gln Asn
        35                  40                  45

Lys Asn Thr Glu Ser Leu Phe Lys Glu Leu Asp Val Asn Ser Asp Asn
    50                  55                  60

Ala Ile Asn Phe Glu Glu Phe Leu Ala Leu Val Ile Arg Val Gly Val
65                  70                  75                  80

Ala Ala His Lys Asp Ser His Lys Glu
                85

<210> SEQ ID NO 20
<211> LENGTH: 270
<212> TYPE: DNA
<213> ORGANISM: Rattus norvegicus

<400> SEQUENCE: 20

| atggcaactg aactggagaa ggccttgagc aacgtcattg aagtctacca caattattct | 60 |
| ggtataaaag ggaatcacca tgccctctac agggatgact tcaggaaaat ggtcactact | 120 |
| gagtgccctc agtttgtgca gaataaaaat accgaaagct tgttcaaaga attggacgtc | 180 |
| aatagtgaca acgcaattaa cttcgaagag ttccttgcgt tggtgataag ggtgggcgtg | 240 |
| gcagctcata agacagcca caaggagtaa | 270 |

<210> SEQ ID NO 21
<211> LENGTH: 93
<212> TYPE: PRT
<213> ORGANISM: Homo sapiens

<400> SEQUENCE: 21

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 22
<211> LENGTH: 282
<212> TYPE: DNA
<213> ORGANISM: Homo sapiens

<400> SEQUENCE: 22

| atgttgaccg agctggagaa agccttgaac tctatcatcg acgtctacca caagtactcc | 60 |
| ctgataaagg ggaatttcca tgccgtctac agggatgacc tgaagaaatt gctagagacc | 120 |
| gagtgtcctc agtatatcag gaaaaagggt gcagacgtct ggttcaaaga gttggatatc | 180 |
| aacactgatg gtgcagttaa cttccaggag ttcctcattc tggtgataaa gatgggcgtg | 240 |
| gcagcccaca aaaaagcca tgaagaaagc cacaaagagt ag | 282 |

<210> SEQ ID NO 23
<211> LENGTH: 113
<212> TYPE: PRT
<213> ORGANISM: Mus musculus

<400> SEQUENCE: 23

Met Ala Asn Lys Ala Pro Ser Gln Met Glu Arg Ser Ile Thr Thr Ile
1               5                   10                  15

Ile Asp Thr Phe His Gln Tyr Ser Arg Lys Glu Gly His Pro Asp Thr
            20                  25                  30

Leu Ser Lys Lys Glu Phe Arg Gln Met Val Glu Ala Gln Leu Ala Thr
        35                  40                  45

Phe Met Lys Lys Glu Lys Arg Asn Glu Ala Leu Ile Asn Asp Ile Met
    50                  55                  60

Glu Asp Leu Asp Thr Asn Gln Asp Asn Gln Leu Ser Phe Glu Glu Cys
65                  70                  75                  80

```
Met Met Leu Met Ala Lys Leu Ile Phe Ala Cys His Glu Lys Leu His
                85                  90                  95

Glu Asn Asn Pro Arg Gly His Gly His Ser His Gly Lys Gly Cys Gly
            100                 105                 110

Lys

<210> SEQ ID NO 24
<211> LENGTH: 342
<212> TYPE: DNA
<213> ORGANISM: Mus musculus

<400> SEQUENCE: 24
atggccaaca aagcaccttc tcagatggag cgcagcataa ccaccatcat cgacaccttc      60
catcaatact ctaggaagga aggacaccct gacaccctga gcaagaagga attcagacaa     120
atggtggaag cacagttggc aacctttatg aagaaagaga gagaaatga agccctcata     180 aatgacatca tggaggacct ggacacaaac caggacaatc agctgagctt tgaggagtgt    240
atgatgctga tggcaaagtt gatctttgcc tgtcatgaga agctgcatga gaacaaccca    300
cgtgggcatg gccacagtca tggcaaaggc tgtgggaagt aa                       342

<210> SEQ ID NO 25
<211> LENGTH: 113
<212> TYPE: PRT
<213> ORGANISM: Rattus norvegicus

<400> SEQUENCE: 25

Met Ala Ala Lys Thr Gly Ser Gln Leu Glu Arg Ser Ile Ser Thr Ile
1               5                   10                  15

Ile Asn Val Phe His Gln Tyr Ser Arg Lys Tyr Gly His Pro Asp Thr
            20                  25                  30

Leu Asn Lys Ala Glu Phe Lys Glu Met Val Asn Lys Asp Leu Pro Asn
        35                  40                  45

Phe Leu Lys Arg Glu Lys Arg Asn Glu Asn Leu Arg Asp Ile Met
    50                  55                  60

Glu Asp Leu Asp Thr Asn Gln Asp Asn Gln Leu Ser Phe Glu Glu Cys
65                  70                  75                  80

Met Met Leu Met Gly Lys Leu Ile Phe Ala Cys His Glu Lys Leu His
                85                  90                  95

Glu Asn Asn Pro Arg Gly His Asp His Arg His Gly Lys Gly Cys Gly
            100                 105                 110

Lys

<210> SEQ ID NO 26
<211> LENGTH: 342
<212> TYPE: DNA
<213> ORGANISM: Rattus norvegicus

<400> SEQUENCE: 26
atggctgcca aaacaggatc tcagctggag cgcagcataa gcaccatcat caatgttttc      60
catcagtact ctaggaagta tggacatcct gacaccctga caaggcgga attcaaagaa     120 atggtgaata aggacttgcc aaattttctg aagagggaga aagaaatga aatctcctta     180 agagacatca tggaggacct ggacacaaac caggacaatc aactgtcctt tgaggagtgt    240
atgatgctga tgggaaagtt gatctttgcc tgtcatgaga agctgcatga gaacaaccca    300
cgtgggcatg accacaggca cggcaaaggc tgtgggaagt aa                       342
```

<210> SEQ ID NO 27
<211> LENGTH: 116
<212> TYPE: PRT
<213> ORGANISM: Homo sapiens

<400> SEQUENCE: 27

Met Thr Cys Lys Met Ser Gln Leu Glu Arg Asn Ile Glu Thr Ile Ile
1               5                   10                  15

Asn Thr Pro His Glu His Gln Tyr Ser Val Lys Leu Gly His Pro Asp
            20                  25                  30

Thr Leu Asn Gln Gly Glu Phe Lys Glu Leu Val Arg Lys Asp Leu Gln
        35                  40                  45

Asn Phe Leu Lys Lys Glu Asn Lys Asn Glu Lys Val Ile Glu His Ile
    50                  55                  60

Met Glu Asp Leu Asp Thr Asn Ala Asp Lys Gln Leu Ser Phe Glu Glu
65                  70                  75                  80

Phe Ile Met Leu Met Ala Arg Leu Thr Trp Ala Ser His Glu Lys Met
                85                  90                  95

His Glu Gly Asp Glu Gly Pro Gly His His His Lys Pro Gly Leu Gly
            100                 105                 110

Glu Gly Thr Pro
        115

<210> SEQ ID NO 28
<211> LENGTH: 345
<212> TYPE: DNA
<213> ORGANISM: Homo sapiens

<400> SEQUENCE: 28
atgacttgca aaatgtcgca gctggaacgc aacatagaga ccatcatcaa caccttccac    60
caatactctg tgaagctggg gcacccagac accctgaacc agggggaatt caaagagctg   120
gtgcgaaaag atctgcaaaa ttttctcaag aaggagaata agaatgaaaa ggtcatagaa   180
cacatcatgg aggacctgga cacaaatgca gacaagcagc tgagcttcga ggagttcatc   240
atgctgatgg cgaggctaac ctgggcctcc cacgagaaga tgcacgaggg tgacgagggc   300
cctggccacc accataagcc aggcctcggg gagggcaccc cctaa                   345

<210> SEQ ID NO 29
<211> LENGTH: 63
<212> TYPE: DNA
<213> ORGANISM: Artificial
<220> FEATURE:
<223> OTHER INFORMATION: An artificially synthesized nucleotide sequence

<400> SEQUENCE: 29
atgcagacag acacactcct gctatgggta ctgctgctgt gggttccagg ttccactggt    60
gac                                                                 63

<210> SEQ ID NO 30
<211> LENGTH: 7
<212> TYPE: PRT
<213> ORGANISM: Artificial
<220> FEATURE:
<223> OTHER INFORMATION: An artificially synthesized peptide sequence

<400> SEQUENCE: 30

Asp Tyr Lys Asp Asp Asp Lys
1               5

<210> SEQ ID NO 31
<211> LENGTH: 220
<212> TYPE: PRT
<213> ORGANISM: Artificial
<220> FEATURE:
<223> OTHER INFORMATION: An artificially synthesized peptide sequence

<400> SEQUENCE: 31

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp
    210                 215                 220

<210> SEQ ID NO 32
<211> LENGTH: 660
<212> TYPE: DNA
<213> ORGANISM: Artificial
<220> FEATURE:
<223> OTHER INFORMATION: An artificially synthesized nucleotide sequence

<400> SEQUENCE: 32
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360

```
gattttctta gcaagctacc tgaaatgctg aaaatgttcg aagatcgttt atgtcataaa      420
acatatttaa atggtgatca tgtaacccat cctgacttca tgttgtatga cgctcttgat      480
gttgttttat acatggaccc aatgtgcctg gatgcgttcc caaaattagt ttgttttaaa      540
aaacgtattg aagctatccc acaaattgat aagtacttga aatccagcaa gtatatagca      600
tggcctttgc agggctggca agccacgttt ggtggtggcg accatcctcc aaaatcggat      660
```

METHOD FOR COLLECTING FUNCTIONAL CELLS IN VIVO WITH HIGH EFFICIENCY

CROSS REFERENCE TO A RELATED APPLICATION

This application is a National Stage Application of International Application Number PCT/JP2009/058525, filed Apr. 30, 2009; which claims priority to Japanese Patent Application No. 2008-119355, filed Apr. 30, 2008; which are incorporated herein by reference in their entirety.

TECHNICAL FIELD

The present invention relates to novel highly efficient and minimally invasive methods for collecting functional cells such as stem cells, which exist in an extremely small number in vivo.

BACKGROUND ART

Conventional methods for collecting highly functional cells from the living body include, for example, methods of collecting hematopoietic bone marrow stem cells, which harvest bone marrow fluid from the bone marrow of a long bone or pelvic bone by directly inserting a needle into the bone marrow, and for administration to human, concentrate a stem cell population by centrifugation, and collect and confirm fluorescently labeled cells with a cell sorter using stem cell surface markers as an indicator; methods of collecting peripheral blood stem cells, which mobilize hematopoietic stem cells to peripheral blood by administering G-CSF, collect peripheral blood and isolate hematopoietic stem cells from the blood; and methods of collecting mesenchymal stem cells, which isolate mesenchymal stem cells by collecting adherent proliferating cells from a direct culture of bone marrow fluid, or isolate and culture mesenchymal stem cells from surgically harvested peripheral tissues such as adipose tissues. However, harvesting bone marrow fluid from the bone marrow is highly invasive and painful, and involves risk of myelitis due to intramedullary infection. Thus, the treatment requires highly strict medical management by experts, and cannot be conducted frequently. Surgical harvest of peripheral tissues also has the same risk. The mobilization of hematopoietic stem cells using G-CSF poses a large economic burden, and also cannot be frequently conducted.

It goes without saying that establishment of efficient and safe methods for collecting biologically functional cells will be encouraging news for many patients that suffer from intractable diseases and are in need of such cells.

PRIOR ART DOCUMENTS

Non-Patent Documents

[Non-patent Document 1] Transplantation of hematopoietic stem cells from the peripheral blood. Cell Mol. Med. 2005; 9: 37-50
[Non-patent Document 2] Role of mesenchymal stem cells in regenerate medicine: application to bone and cartilage repair. Expert Opin Biol Ther. 2008; 8: 255-268

DISCLOSURE OF THE INVENTION

Problems to be Solved by the Invention

An objective of the present invention is to provide novel highly efficient and minimally invasive techniques for collecting functional cells such as stem cells, which exist in an extremely small number in vivo.

Means for Solving the Problems

The present invention provides brand new, highly efficient techniques for harvesting biologically functional cells by only implanting a tube into a living body in a minimally invasive manner.

Specifically, cylindrical tubes (which has a length of 10 mm and a cross-sectional area of about 2 $mm^2$, and is open on one side and closed on the other side) made of biologically hypoallergenic silicone were filled with each of HMGB1, hyaluronic acid, phosphate buffer, or such, and then implanted under the dorsal skin of GFP bone marrow-transplanted mice. The tubes were recovered two weeks after implantation, and cells mobilized and accumulated in the tubes were collected. Some of the cells were cultured, and others were analyzed for cell surface markers by FACS. The result shows that as compared to tubes filled with phosphate buffer, significantly more PDGFRα-positive cells were harvested from tubes filled with an agent other than phosphate buffer, and these cell populations contained mesenchymal stem cells with the ability to differentiate into bone and cartilage.

Based on the above findings, the present invention provides:

[1] a method for collecting a cell population from a vessel removed outside the body from under the skin;
[2] a method for harvesting a cell population from a vessel removed outside the body from under the skin, wherein the cell population is mobilized into the vessel by any one of the materials of (a) to (r) described below, or a mixture of any two or more of the materials of (a) to (r) described below:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) a cell or tissue extract; and
(r) a heparin-binding fraction of cell or tissue extract;
[3] a method for collecting a bone marrow cell, which comprises the step of isolating a bone marrow cell from a cell population collected from a vessel implanted under the skin;
[4] a method for collecting a bone marrow cell, which comprises the step of isolating a bone marrow cell from a cell population collected from a vessel implanted under the skin, wherein the cell population is mobilized into the vessel by any one of the materials of (a) to (r) described below, or a mixture of any two or more of the materials of (a) to (r) described below:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) a cell or tissue extract; and
(r) a heparin-binding fraction of cell or tissue extract;
[5] the method of [3] or [4], which comprises the step of collecting the cell population from a vessel removed outside the body before the step of isolating a bone marrow cell from a cell population;
[6] the method of [2] or [4], wherein an extract of cell or tissue is produced by a method comprising the step of immersing a cell or tissue in a solvent;
[7] the method of [2] or [4], wherein a heparin-binding fraction of an extract cell or tissue is produced by a method comprising the steps of:
(a) immersing a cell or tissue in a solvent;
(b) contacting immobilized heparin with an extract prepared in step (a); and
(c) eluting a heparin-binding fraction from the immobilized heparin;
[8] a cell population collected by the method of any one of [1], [2], [6], and [7];
[9] a bone marrow cell isolated by the method of any one of [3] to [7];
[10] a tissue-regenerating agent comprising the cell population of [8];
[11] a tissue-regenerating agent comprising the bone marrow cell of [9];
[12] a method for collecting a cell population, which comprises the steps of:
(I) implanting a vessel under the skin; and
(II) collecting a cell population from the vessel;
[13] the method of [12], which comprises the step of administering any one of (a) to (r) or a mixture of any two or more of (a) to (r) to blood vessel or muscle after step (I):
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein;
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) an extract of a cell or tissue; and
(r) a heparin-binding fraction of an extract of a cell or tissue;
[14] the method of [12], in which the vessel contains any one, or a mixture of any two or more of:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein;
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) an extract of a cell or tissue; and
(r) a heparin-binding fraction of a extract of a cell or tissue;
[15] a method for collecting a bone marrow cell, which comprises the steps of:
(I) implanting a vessel under the skin;
(II) harvesting a cell population from the vessel; and
(III) isolating a bone marrow cell from the harvested cell population;
[16] the method of [15], which comprises the step of administering any one of (a) to (r) or a mixture of any two or more of (a) to (r) to blood vessel or muscle after step (I):
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein;
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;

(p) hyaluronic acid;
(q) a cell or tissue extract; and
(r) a heparin-binding fraction of cell or tissue extract;
[17] the method of [15], in which the vessel contains any one, or a mixture of any two or more of:
(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein;
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) an extract of a cell or tissue; and
(r) a heparin-binding fraction of cell or tissue extract;
[18] the method of any one of [13], [14], [16], and [17], in which the extract of a cell or tissue is produced by a method comprising the step of immersing a cell or tissue in a solvent;
[19] the method of any one of [13], [14], [16], and [17], in which the heparin-binding fraction of the extract of a cell or tissue is produced by a method comprising the steps of:
(a) immersing a cell or tissue in a solvent;
(b) contacting immobilized heparin with an extract prepared in step (a); and
(c) eluting a heparin-binding fraction from the immobilized heparin;
[20] a cell population collected by the method of any one of [12] to [14];
[21] a bone marrow cell isolated by the method of any one of [15] to [17];
[22] a tissue-regenerating agent comprising the cell population of [20]; and
[23] a tissue-regenerating agent comprising the bone marrow cell of [21].

BRIEF DESCRIPTION OF THE DRAWINGS

FIG. 16A shows in a photograph a mouse fixed to a brain stereotaxic apparatus and subjected to a midline incision in the head with a scalpel, followed by trepanation using a drill. FIG. 16B shows in a photograph a brain to which a negative pressure is applied using a syringe to suck part of the brain tissue. FIG. 16C is a photograph of a mouse after injection of 5 µl heparin-column purified fraction of a skin extract dissolved in fibrin adhesive formulation (fibrinogen), and a subsequent injection of 5 µl of fibrin glue formulation (thrombin). FIGS. 16D and 16E are photographs of the brain injury model taken 2 weeks after the treatment. Higher accumulation of GFP-positive cells was observed in the treatment group using the heparin-column purified fraction of skin extract in E compared to the control in D. FIGS. 16F and 16G are photographs of the brain injury model taken 6 weeks after the treatment. Higher accumulation of GFP-positive cells was observed in the treatment group using the heparin-column purified fraction of skin extract in G compared to the control in F.

Figure 17:
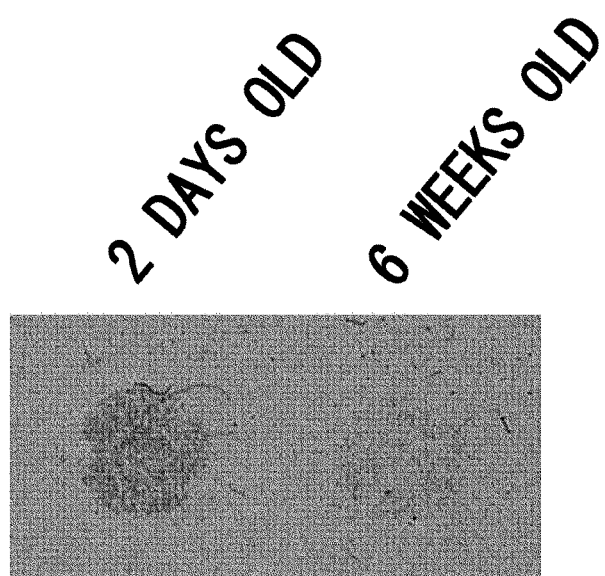

FIG. 17 shows in a photograph assay results of measuring the migratory activity of bone-marrow derived mesenchymal stem cells in skin extracts using a Boyden chamber. These images show blue-stained bone marrow mesenchymal stem cells, which have migrated from the upper compartment of the Boyden chamber through a 8-μm micropore polycarbonate membrane filter into the lower compartment containing skin extracts, and adhered to the lower-compartment side of the membrane. Skin extracts collected from two-day-old or six-week-old mice were placed in the lower chambers.

Figure 18:
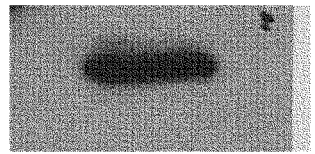
Figure 18:
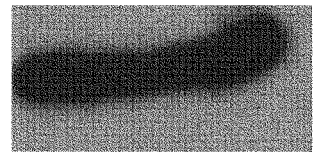

FIG. 18 shows in a set of photographs Western blot detection of the S100A8 and S100A9 proteins in skin extracts.

Figure 19:
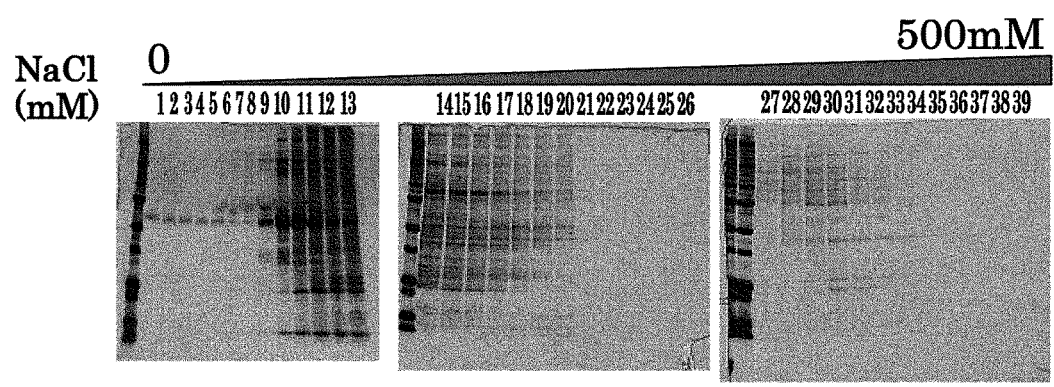

FIG. 19 shows in a photograph elution of a heparin-binding protein in skin extracts eluted from a heparin affinity column by a concentration gradient of NaCl. Proteins in each fraction were separated by SDS-PAGE and detected by silver staining.

Figure 20:
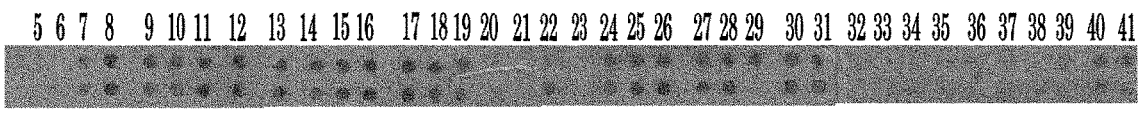

FIG. 20 shows in a photograph assay results of measuring the migratory activity of bone marrow-derived mesenchymal stem cells in skin extracts using a Boyden chamber. The image shows blue-stained bone marrow mesenchymal stem cells, which have migrated from the upper compartment of the Boyden chamber through the micropores of a filter to each heparin-binding fraction in skin extracts (to the lower compartment), and adhered to the lower-compartment side of the membrane.

Figure 21:
Figure 21:

FIG. 21 shows in a set of photographs Western blot detection of the S100A8 and S100A9 proteins in each heparin-binding fraction of skin extracts.

Figure 22:
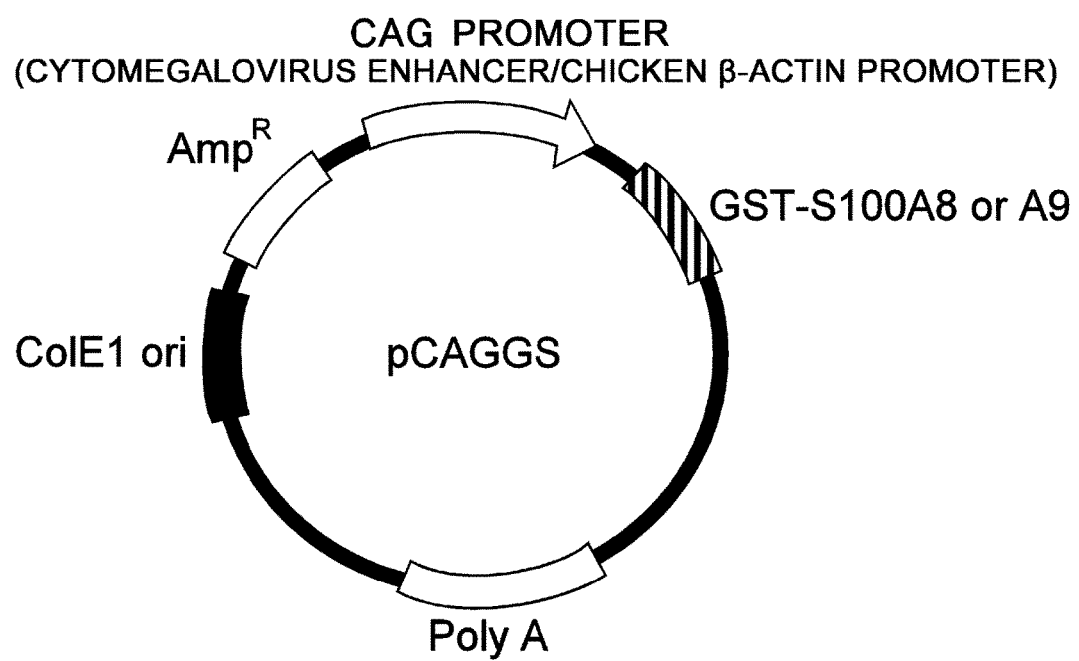

FIG. 22 shows in a diagram the expression vector for S100A8 or S100A9.

Figure 23:
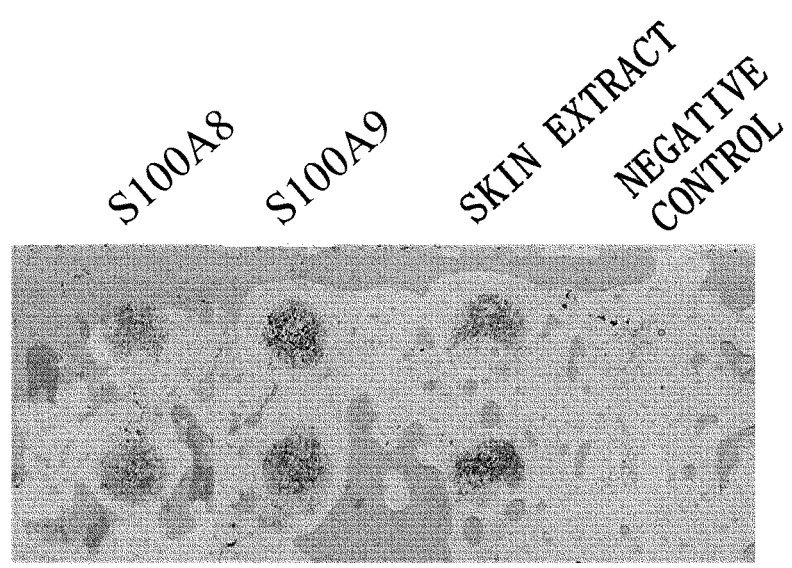

FIG. 23 shows in a photograph assay results of measuring the migratory activity of bone marrow-derived mesenchymal stem cells in skin extracts using a Boyden chamber. These images show blue-stained bone marrow mesenchymal stem cells, which have migrated from the upper compartment of the Boyden chamber through the micropores of a filter into the lower compartment containing recombinant GST-S100A8, GST-S100A9, or skin extracts, and adhered to the lower-compartment side of the membrane.

FIG. 24A shows in a set of diagrams the FACS results for CD44, PDGFRα, and PDGFRβ in the CD45-negative cell fraction in peripheral blood 12 hours after administration of GST-S100A8 or GST-S100A via the mouse caudal vein. FIG. 24B shows in graphs quantitative analysis of the populations of CD45-negative, CD44-positive, PDGFRα-positive cells, or CD45-negative, CD44-positive, PDGFRβ-positive cells in peripheral blood 12 hours after administration of GST-S100A8 or GST-S100A based on the FACS results.

Figure 25:
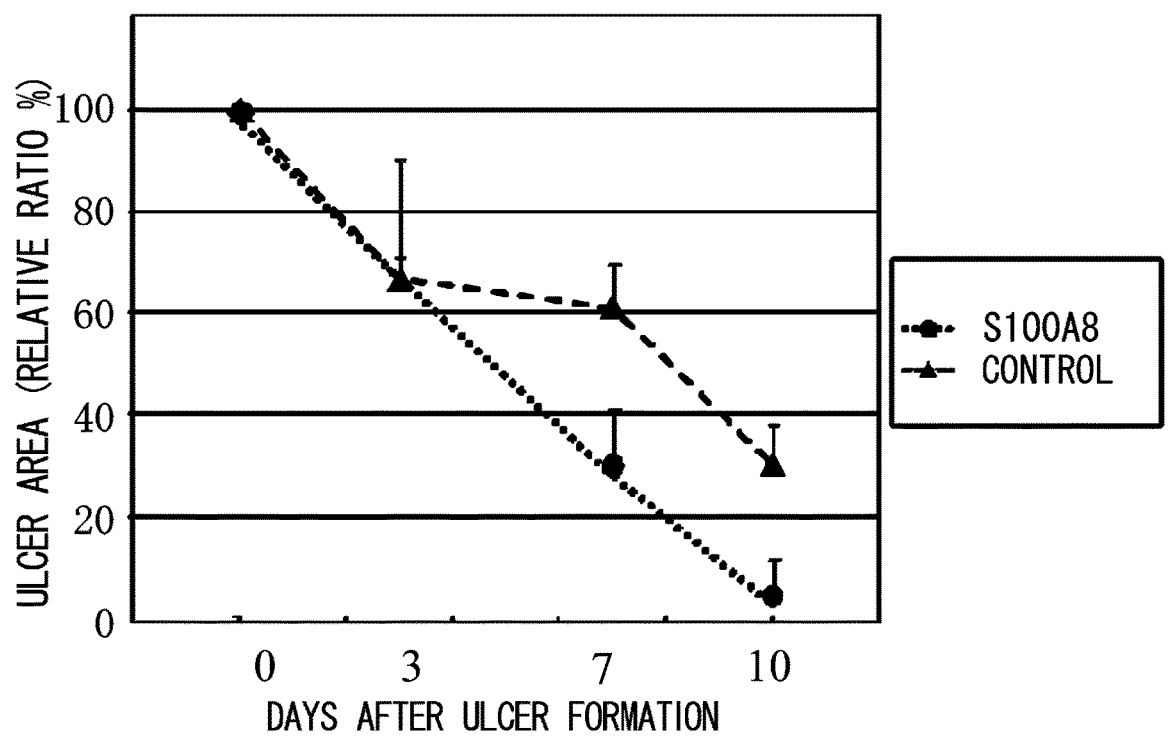

FIG. 25 shows in a graph therapeutic effect of S100A8 on cutaneous ulcer in normal mice.

Figure 26:
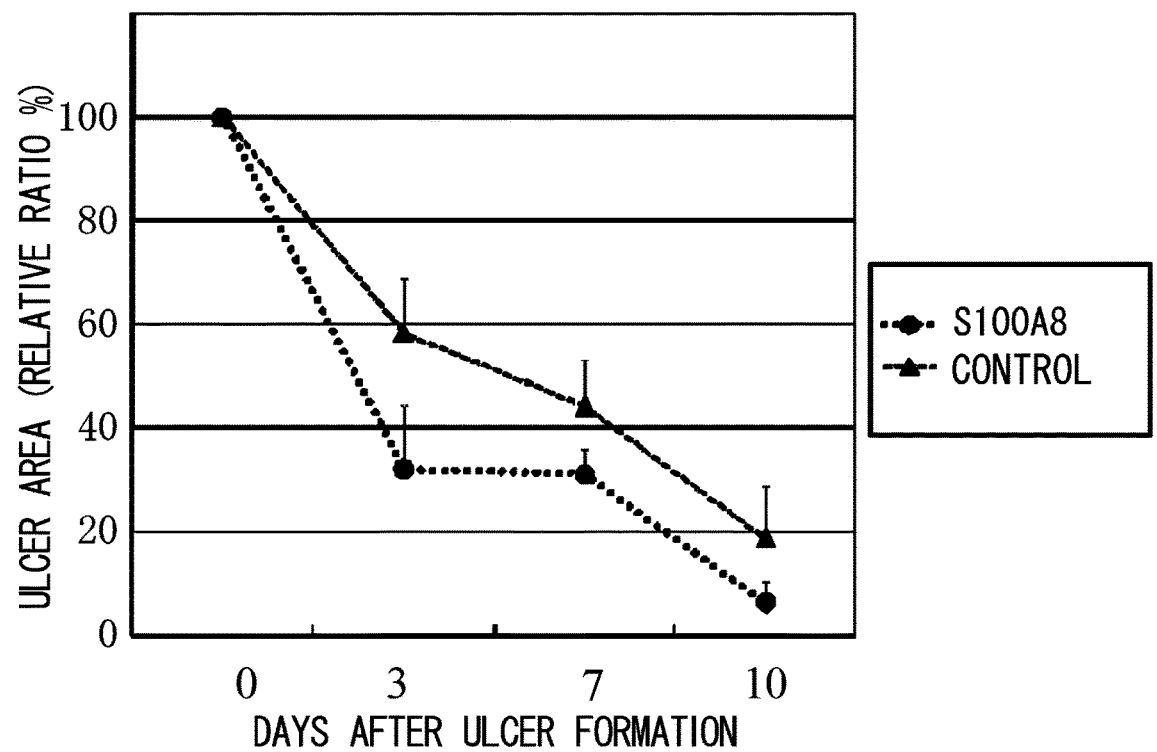

FIG. 26 shows in a graph therapeutic effect of S100A8 on cutaneous ulcer in diabetic mice.

Figure 27:
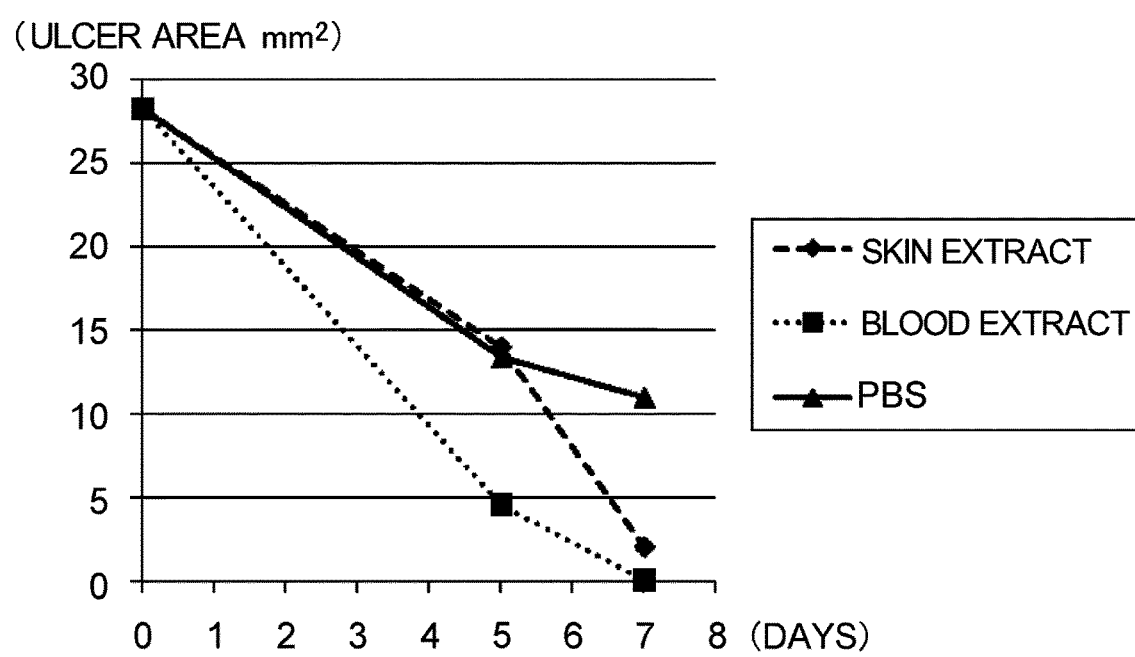

FIG. 27 shows in a graph therapeutic effect of cells that are mobilized into a device using skin extracts or peripheral blood extracts on cutaneous ulcer.

Figure 28:
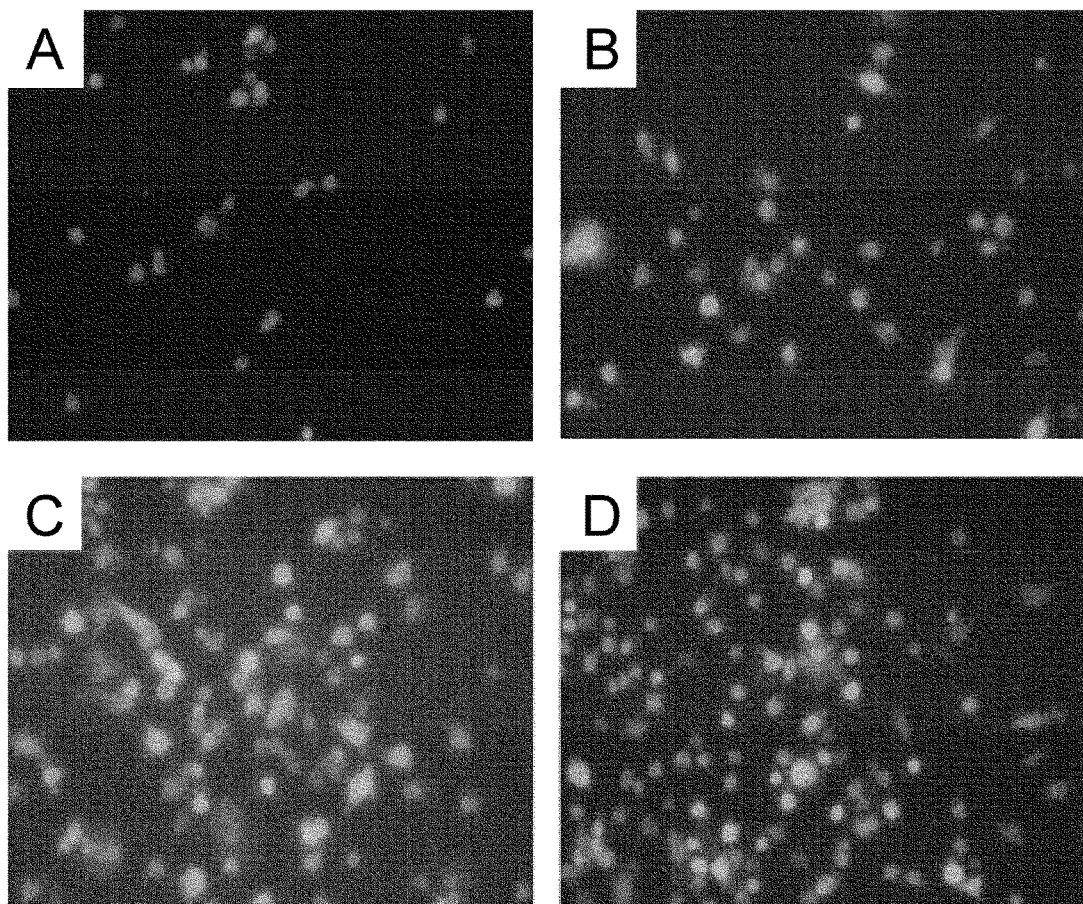

FIG. 28 shows in a set of photographs fluorescence microscopic detection of bone marrow cells mobilized into a device using heparin affinity column-binding components of peripheral blood extracts.

Figure 29:
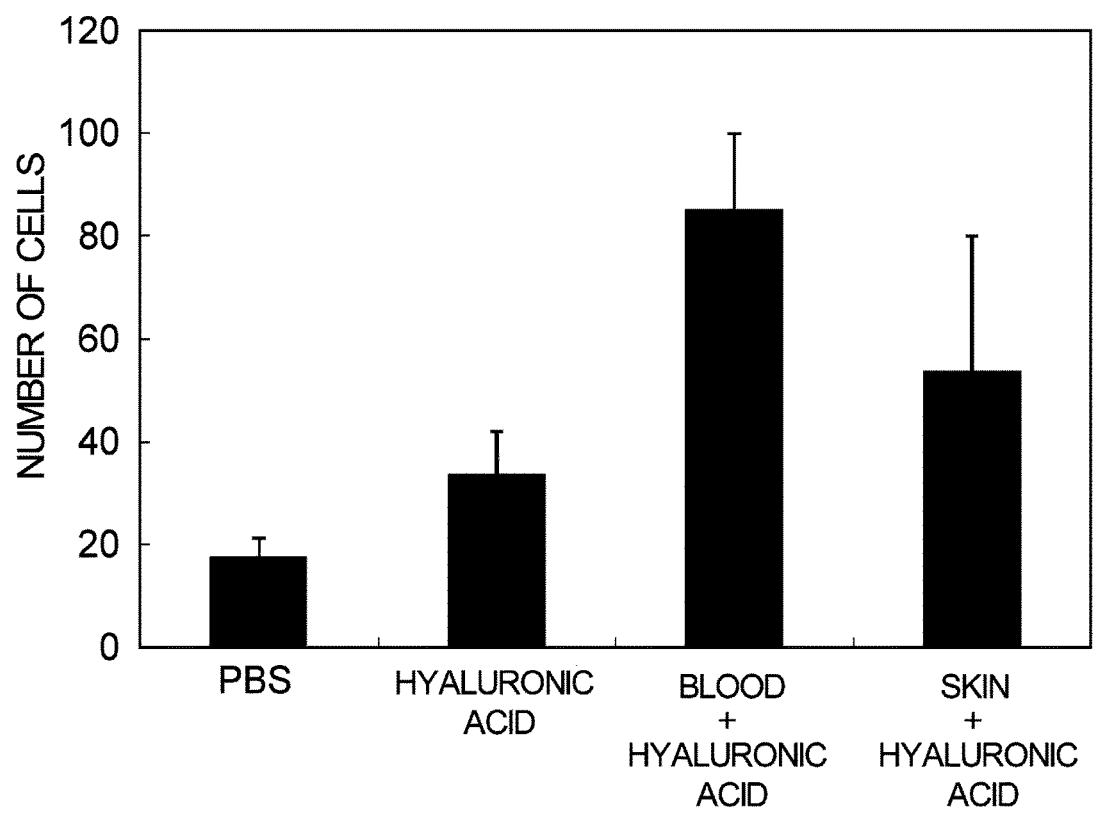

FIG. 29 shows in a graph detection of bone marrow cells mobilized into a device using heparin affinity column-binding components of peripheral blood extracts by fluorescence microscopy, and quantification of the number of bone marrow cells using an image analysis software.

Figure 30:
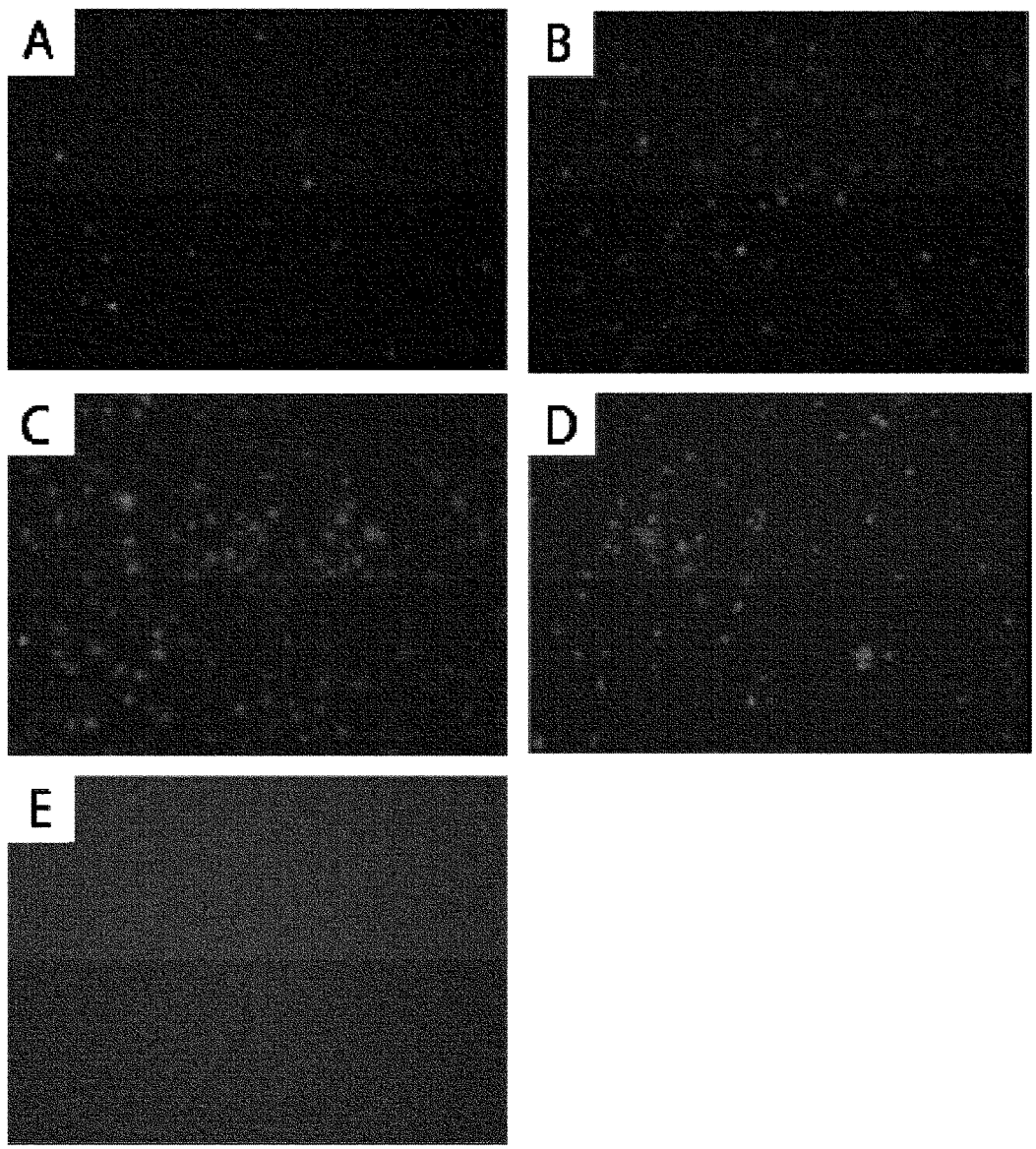

FIG. 30 shows in a graph detection of bone marrow-derived cells (GFP-positive cells) mobilized into a device using S100A8, HMGB1, HMGB2, or HMGB3 (A, S100A8; B, HMGB1; C, HMGB2; D, HMGB3; E, negative control) by fluorescence microscopy.

Figure 31:
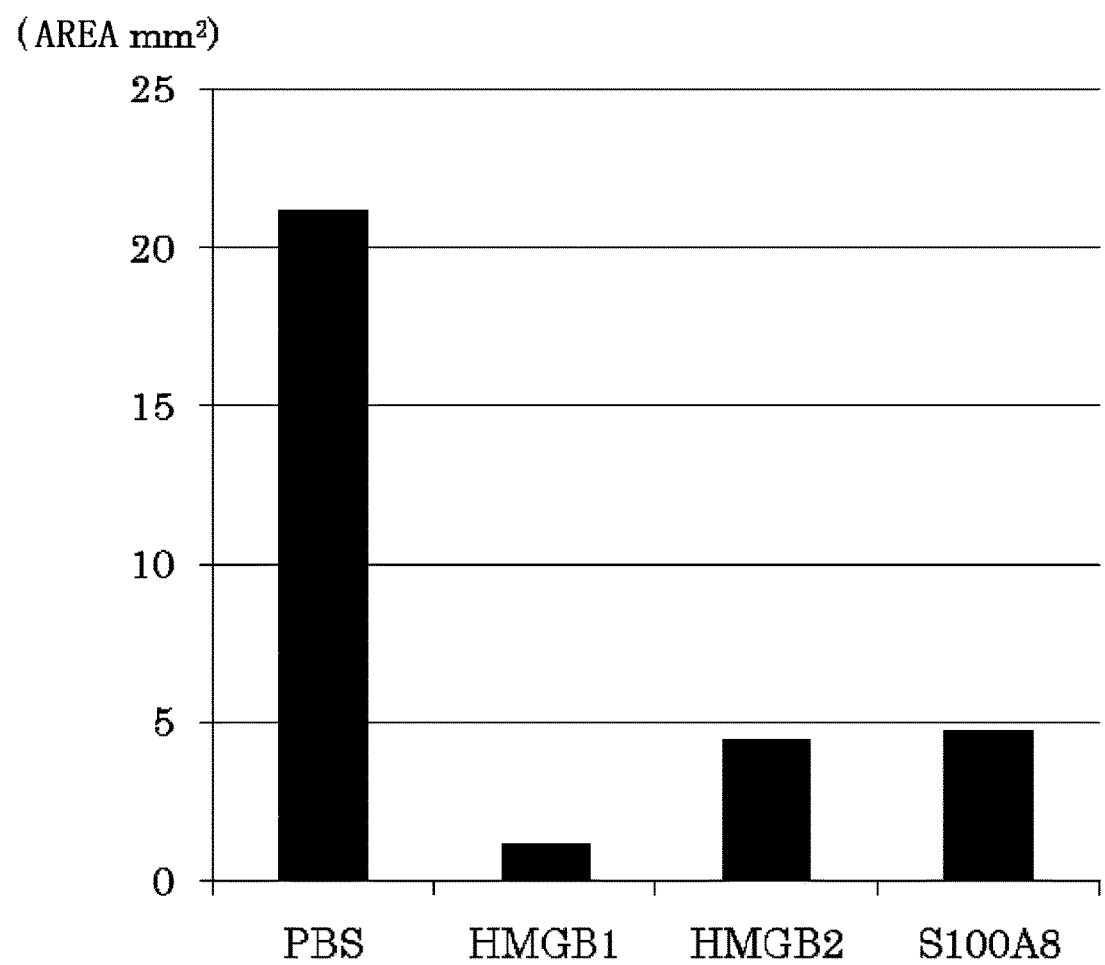

FIG. 31 shows in a set of photographs therapeutic effect on cutaneous ulcer developed in BALB/cAJcl-nu/nu mice, of bone marrow-derived cells mobilized into a device using S100A8, HMGB1, or HMGB2.

Figure 32:
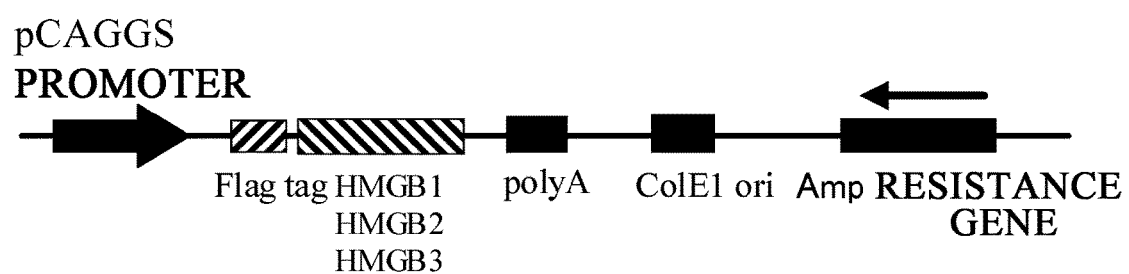

FIG. 32 shows in a diagram an HMGB1 expression vector.

Figure 33:
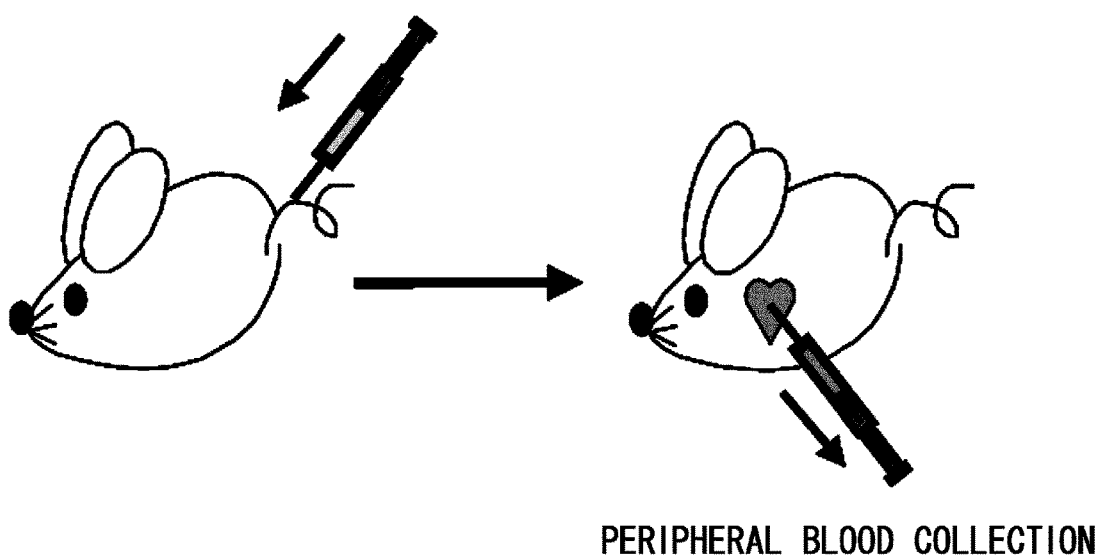

FIG. 33 shows in a diagram administration of skin extract (SE) to a mouse via caudal vein, followed by collection of peripheral blood.

Figure 34:
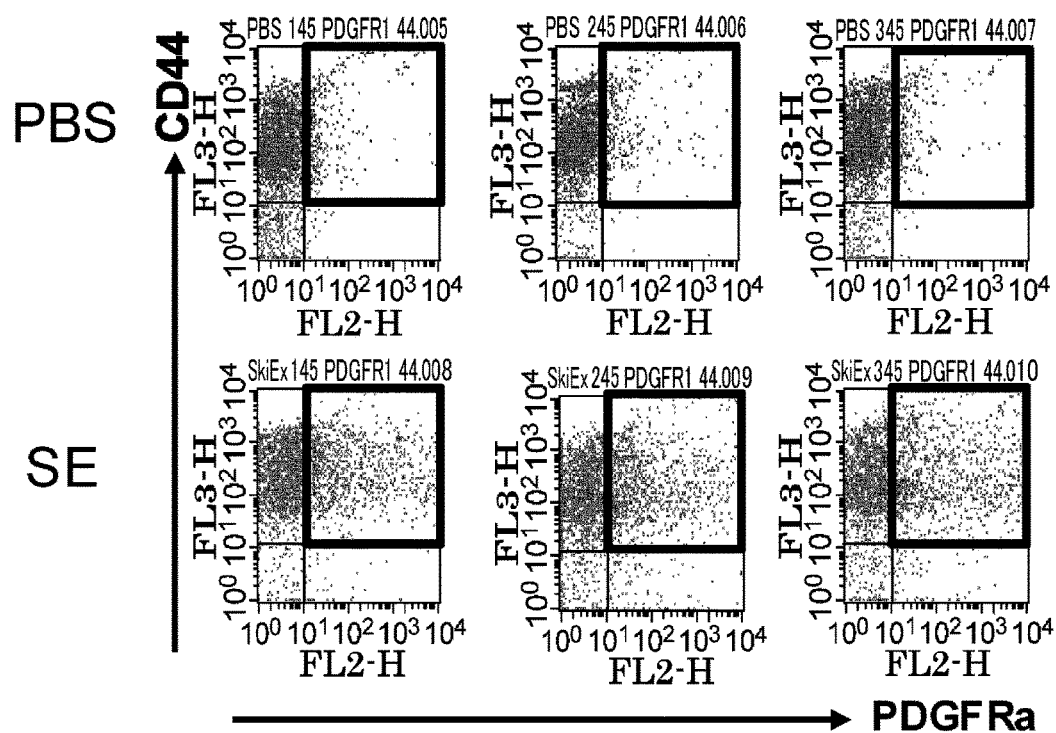

FIG. 34 shows in a diagram flow cytometric fractionation of a mouse peripheral blood mononuclear cell fraction fluorescently labeled with anti-mouse PDGFRα antibody and anti-mouse CD44 antibody 12 hours after administration of skin extract (SE). The upper three charts correspond to the PBS-administered group (n=3) as a negative control, while the lower three charts correspond to the skin extract (SE)-administered group (n=3). The vertical axis indicates the expression level of CD44, and the horizontal axis indicates the expression level of PDGFRα. The area boxed with blue line corresponds to a population of CD44 and PDGFRα double-positive cells. The population was increased in the skin extract-administered group (SE) as compared to the PBS-administered group.

Figure 35:
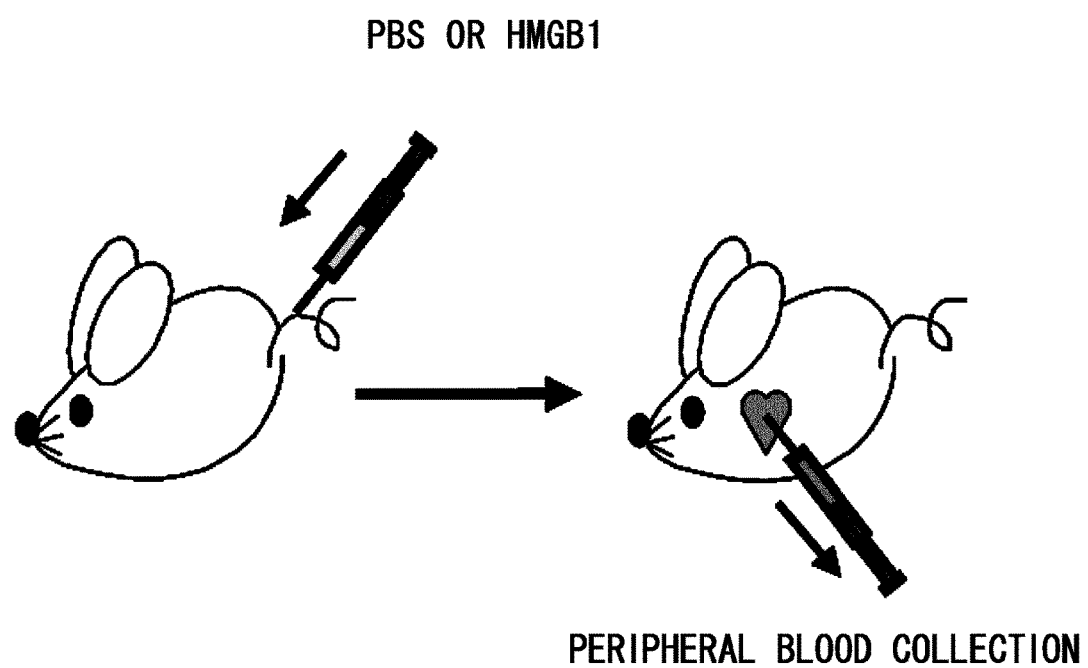

FIG. 35 shows in a diagram administration of HMGB1 to a mouse via caudal vein, followed by collection of peripheral blood.

Figure 36:
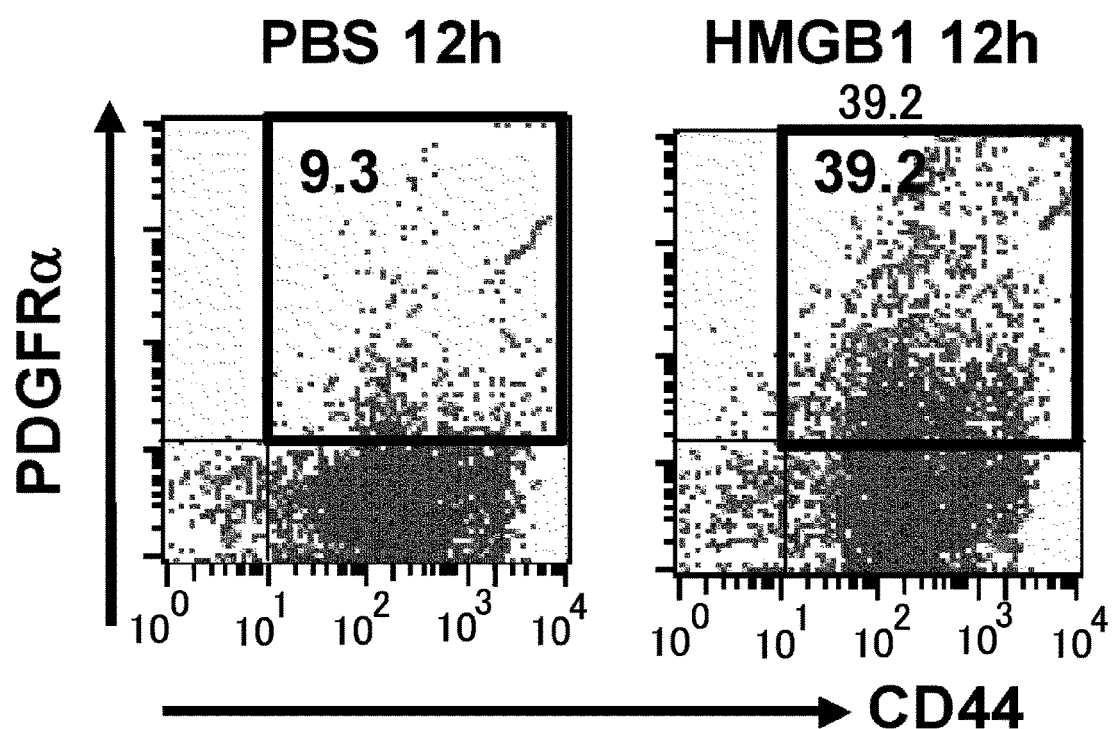

FIG. 36 shows in a diagram flow cytometric fractionation of mouse peripheral blood mononuclear cell fraction fluorescently labeled with anti-mouse PDGFRα antibody and anti-mouse CD44 antibody 12 hours after administration of HMGB1. The left chart corresponds to the PBS-administered mice as a negative control, while the right chart corresponds to the HMGB1-administered mice. The vertical axis indicates the expression level of CD44, and the horizontal axis indicates the expression level of PDGFRα. The area boxed with blue line corresponds to a population of CD44 and PDGFRα double-positive cells. The population was increased in the HMGB1-administered mice as compared to the PBS-administered mice.

FIG. 37A shows in a diagram the flow cytometry result that shows the presence of cells having CD44 and PDGFRα. HMGB1 administration increased both populations of PDGFRα and CD44 double-positive cells, and PDGFRα-positive CD44-negative cells in peripheral blood. FIGS. 37B and 37C show results of comparison between the PBS- and HMGB1-administered groups on the presence of PDGFRα and CD44 double-positive cells, and PDGFRα-positive CD44-negative cells in peripheral blood, respectively. Both cell populations were statistically significantly increased in the HMGB1-administered group.

MODE FOR CARRYING OUT THE INVENTION

The present invention provides a method for collecting a cell population from a vessel removed outside the body from under the skin.

The present invention also provides a method for collecting a bone marrow cell, which comprises the step of isolating a bone marrow cell from a cell population collected from a vessel implanted under the skin. The above method may include the step of collecting the cell population from the vessel removed outside the body before the step of isolating a bone marrow cell from a cell population.

The present invention provides a method for collecting a cell population, which comprises the steps of:
(I) implanting a vessel under the skin; and
(II) collecting a cell population from the vessel.

Furthermore, the present invention provides a method for collecting a bone marrow cell, which comprises the steps of:
(I) implanting a vessel under the skin;
(II) harvesting a cell population from the vessel; and
(III) isolating a bone marrow cell from the harvested cell population.

Alternatively, the methods described above may comprise, subsequent to step (I), the step of removing the vessel from under the skin.

Preferred materials for the above-described vessel include, but are not limited to, silicone, vinyl, plastic, and other biologically hypoallergenic materials. Meanwhile, the size of vessel used in the Examples was: 10 mm length×2 mm cross-sectional area (with a volume of 20 ml; for mice); however, the size is not limited to the above example, as long as the vessel can be implanted under the skin. The wall thickness of vessel used in the Examples was about 0.5 mm; however, the thickness is not limited to the above examples, as long as it is sufficient to maintain adequate strength. The shape of vessel used in the Examples was a cylindrical shape that is open only on one side; however, the shape is not particularly limited, so long as it does not damage biological tissues; and the shape includes cylindrical, spindle, spherical, and ovoid. Vessels used in the present invention include silicone tubes, vinyl bags, and indwelling injection needles. The vessels are not particularly limited, as long as they are implantable medical materials or devices in vivo.

In the present invention, cell populations harvested from the vessel include bone marrow-derived cells.

Bone marrow cells of the present invention are cells other than hematopoietic stem cells, or cells derived therefrom such as leukocytes, erythrocytes, and platelets, and include stem cells represented by cells which have been hitherto called bone marrow mesenchymal stem cells, bone marrow stromal pluripotent stem cells, or bone marrow pluripotent stem cells and tissue progenitor cell populations existing in the bone marrow. Bone marrow cells of the present invention can be isolated from bone-marrow collection (bone marrow cell collection) or peripheral blood collection. Hematopoietic stem cells are nonadherent, while bone marrow cells of the present invention are obtained as adherent cells by means of a cell culture of a mononuclear cell fraction of blood obtained from the bone marrow collection (bone marrow cell collection) or peripheral blood collection. Moreover, bone marrow cells of the present invention include mesenchymal stem cells, and have a potential to differentiate into, preferably, osteoblasts (the induction of differentiation can be identified by observing calcification), chondrocytes (which can be identified by alcian blue positive staining, safranin O positive staining, or the like), adipocytes (which can be identified by Sudan III positive staining), and other mesenchymal cells such as fibroblasts, smooth muscle cells, stromal cells, and tendon cells; and further nerve cells, epithelial cells (for example, epidermal keratinocytes and intestinal epithelial cells express cytokeratin family), and vascular endothelial cells. However, the cells to be differentiated into are not limited to the above cells, and the potential to differentiate into cells of parenchymatous organs such as liver, kidney, and pancreas are also included.

In the present invention, bone marrow-derived mesenchymal stem cells, bone marrow stromal pluripotent stem cells, or bone marrow pluripotent stem cells refer to cells existing in the bone marrow, which are directly collected from the bone marrow or indirectly collected from other tissues (blood, skin, adipose, and other tissues), and can be cultured/proliferated as adherent cells on a culture dish (made of plastic or glass). These cells are characterized in having a potential to differentiate into mesenchymal tissues (mesenchymal stem cells) such as bone, cartilage, and adipose, or skeletal muscles, heart muscles, further, nerve tissues, epithelial tissues (pluripotent stem cells) and can be obtained from a collection of bone marrow blood, peripheral blood, or mesenchymal tissues such as adipose, epithelial tissues such as skin, nerve tissues such as brain. Bone marrow-derived mesenchymal stem cells, bone marrow-derived pluripotent stem cells, or bone marrow pluripotent stem cells are also characterized in having a potential to differentiate into epithelial tissues such as keratinocytes that constitute skin or into nerve tissues that constitute brain, by administrating these cells that have once adhered onto a culture dish to a lesion area of the living body.

Bone marrow mesenchymal stem cells, bone marrow stromal pluripotent stem cells, or bone marrow pluripotent stem cells of the present invention are multipotent stem cells, and have a potency to differentiate preferably into: osteoblasts (the induction of differentiation can be identified by observing calcification), chondrocytes (which can be identified by alcian blue positive staining, safranin O positive staining, or the like), adipocytes (which can be identified by Sudan III positive staining or the like), and other mesenchymal cells such as fibroblasts, smooth muscle cells, skeletal muscle cells, stromal cells, and tendon cells; nerve cells, pigment cells, epidermal cells, hair follicle cells (which express cytokeratin family, hair keratin family, or the like), epithelial cells (for example, epidermal keratinocytes and intestinal epithelial cells express cytokeratin family or the like), and endothelial cells; and further preferably into cells of parenchymatous organs such as liver, kidney, and pancreas. However, differentiated cells are not limited to the above cells.

Tissue progenitor cells are defined as undifferentiated cells having a unidirectional potency to differentiate into specific tissue cells other than the blood system, and include undifferentiated cells having the potency to differentiate into mesenchymal tissue, epithelial tissue, nerve tissue, parenchymatous organs, and vascular endothelium as mentioned above.

Meanwhile, bone marrow cells of the present invention include, but are not limited to, for example, bone marrow cells positive for at least one of the cell surface markers: CD44, PDGFRα, and PDGFRβ.

In the present invention, the step of implanting a vessel under the skin is achieved by performing skin incision of several millimeters with a scalpel after general (or local) anesthesia; creating a necessary space in subcutaneous adipose tissue by blunt dissection using a round-ended metal rod (mosquito forceps or such); implanting a cell harvesting vessel such as a silicone tube into the space; and finally closing the incision by suture or stapling.

Possible alternative methods for indwelling vessels under the skin include methods which insert the inner and outer sheaths of an injection needle under the skin, and then removing the inner sheath (injection needle) and leaving the outer sheath in; and methods which insert balloon catheter over a guide wire under the skin, and indwelling the catheter after removing the guide wire by expanding its balloon with a pharmaceutical fluid.

Subjects of the vessel implantation include humans and nonhuman animals, including, for example, humans, mice, rats, monkeys, pigs, dogs, rabbits, hamsters, and guinea pigs. The preferred subject is humans.

In the present invention, the step of collecting cell populations from vessels may be either the step of harvesting cell populations from vessels implanted under the skin, or the step of removing the vessels from under the skin, followed by collecting cell populations from the removed vessels. For example, the Examples herein describe that silicone tubes implanted under the skin were recovered via skin incision and cells were collected from the tubes by aspiration using pipettes. However, other methods are also available.

Methods for collecting cell populations from vessels implanted under the skin are carried out as follows: a vessel to be implanted under the skin is modified to be elongated to form a tube-shaped end; the tube-like portion is fixed outside the body; a syringe is attached to the tube at the time of cell harvest; and the cells are harvested by vacuum aspiration. Then, a cell inducing solution such as HMGB1 solution is re-injected into the tube implanted in the body. This enables repeated cell harvest from the vessel implanted under the skin. Vessels whose shape is suitable for the methods are implanted in the body.

In the present invention, the step of isolating bone marrow cells from the harvested cell populations is achieved, for example, by isolating adherent cells adhered to culture dishes from the harvested cell populations.

Another method, for example, harvests cells by pipetting from tubes removed from the body; reacting at least one of the cell surface markers, CD44, PDGFRα, and PDGFRβ using antibodies labeled with different types of fluorescent labels; and then using a cell sorter to isolate cell populations having specific cell surface markers with the presence of each type of fluorescence as an indicator.

There is an alternative method (MACS), which is performed, for example, as follows: cell surface markers are reacted in the same way with antibodies labeled with metal particles instead of fluorescence; cells bound with the metal-linked antibodies are attracted and immobilized onto the internal wall of one side of the tube using magnetic force; after thoroughly eluting cells nonreactive to the antibodies, target cells immobilized in the tube are collected by releasing the magnetic force.

The present invention provides methods for collecting cell populations from vessels removed to the outside of the body from under the skin, in which any one of the materials of (a) to (r), or a mixture of any two or more of the materials of (a) to (r) described below are responsible for mobilizing the cell populations into the vessels from the bone marrow.

The present invention also provides methods for collecting bone marrow cells, which comprise the step of isolating bone marrow cells from cell populations harvested from vessels implanted under the skin, and in which any one of the materials of (a) to (r) described below, or a mixture of any two or more of the materials of (a) to (r) described below are responsible for mobilizing the cell populations to the vessels from the bone marrow. The above methods may comprise the step of collecting cell populations from vessels removed from the body before the step of isolating bone marrow cells from the cell populations.

(a) an HMGB1 protein;
(b) a cell that secretes an HMGB1 protein;
(c) a vector inserted with a DNA encoding an HMGB1 protein;
(d) an HMGB2 protein;
(e) a cell that secretes an HMGB2 protein;
(f) a vector inserted with a DNA encoding an HMGB2 protein;
(g) an HMGB3 protein;
(h) a cell that secretes an HMGB3 protein; and
(i) a vector inserted with a DNA encoding an HMGB3 protein;
(j) an S100A8 protein;
(k) a cell that secretes an S100A8 protein;
(l) a vector inserted with a DNA encoding an S100A8 protein;
(m) an S100A9 protein;
(n) a cell that secretes an S100A9 protein;
(o) a vector inserted with a DNA encoding an S100A9 protein;
(p) hyaluronic acid;
(q) an extract of cells or tissues; and
(r) a heparin-binding fraction of cell or tissue extract.

The present invention provides methods comprising the steps of:
(I) implanting a vessel under the skin; and
(II) harvesting a cell population from the vessel;
and further comprising subsequent to step (I), the step of administering to blood vessel or muscle any one, or a mixture of any two or more of the materials of (a) to (r) described above.

To achieve step (II), a cell population may be collected from a vessel in the body or a vessel removed from the body.

The present invention also provides methods for collecting bone marrow cells, which comprise the steps of:
(I) implanting a vessel under the skin;
(II) collecting a population of cells from the vessel; and
(III) isolating bone marrow cells from the harvested cell population;
and further comprising subsequent to step (I), the step of administering to blood vessel or muscle any one of the materials of (a) to (r) described above, or a mixture of any two or more of the materials of (a) to (r) described above.

To achieve step (II), a cell population may be harvested from a vessel in the body or a vessel removed from the body.

The present invention provides methods for collecting cell populations, which comprise the steps of:
(I) implanting a vessel under the skin; and
(II) collecting a population of cells from the vessel;
where the vessel contains any one of the materials of (a) to (r) described above, or a mixture of any two or more of the materials of (a) to (r) described above.

To achieve step (II), cell populations may be harvested from a vessel implanted in the body or a vessel removed from the body.

The present invention also provides methods for collecting bone marrow cells, which comprise the steps of:
(I) implanting a vessel under the skin;
(II) collecting a population of cells from the vessel; and
(III) isolating bone marrow cells from the harvested cell population;
where the vessel contains any one of the materials of (a) to (r) described above, or a mixture of any two or more of the materials of (a) to (r) described above.

To achieve step (II), a cell population may be collected from a vessel implanted in the body or a vessel removed from the body.

The present invention also provides methods for collecting cell populations, which comprise the steps of:
(I) implanting a vessel under the skin; and
(II) collecting a population of cells from the vessel:
where the vessel contains any one of the materials of (a) to (r) described above, or a mixture of any two or more of the materials of (a) to (r) described above; and which also comprise subsequent to step (I), the step of administering to blood vessel or muscle, any one of the materials of (a) to (r) described above, or a mixture of any two or more of the materials of (a) to (r) described above.

To achieve step (II), a cell population may be collected from a vessel implanted in the body or a vessel removed from the body.

The present invention also provides methods for collecting bone marrow cells, which comprise the steps of:
(I) implanting a vessel under the skin;
(II) collecting a population of cells from the vessel; and
(III) isolating bone marrow cells from the harvested cell population;
where the vessel contains any one of the materials of (a) to (r) described above, or a mixture of any two or more of the materials of (a) to (r) described above; and which also comprise subsequent to step (I), the step of administering to blood vessel or muscle any one of the materials of (a) to (r) described above, or a mixture of any two or more of the materials of (a) to (r) described above.

To achieve step (II), a cell population may be harvested from a vessel implanted in the body or a vessel removed from the body.

The HMGB1 protein of the present invention can be exemplified by, but is not limited to proteins comprising the amino acid sequence of SEQ ID NO: 1, 3, or 5. HMGB1 proteins of the present invention can also include proteins which are functionally equivalent to the protein comprising the amino acid sequence of SEQ ID NO: 1, 3, or 5. Examples of such proteins include: 1) isolated proteins which comprise an amino acid sequence with one or more amino acid substitutions, deletions, insertions, and/or additions in the amino acid sequence of SEQ ID NO: 1, 3, or 5, and which are functionally equivalent to the protein comprising the amino acid sequence of SEQ ID NO: 1, 3, or 5; and 2) isolated proteins which are encoded by DNAs that hybridize under stringent conditions with DNAs comprising the nucleotide sequence of SEQ ID NO: 2, 4, or 6, and which are functionally equivalent to the protein comprising the amino acid sequence of SEQ ID NO: 1, 3, or 5.

The HMGB2 protein of the present invention can be exemplified by, but is not limited to proteins comprising the amino acid sequence of SEQ ID NO: 7, 9, or 11. HMGB2 proteins of the present invention can also include proteins which are functionally equivalent to the protein comprising the amino acid sequence of SEQ ID NO: 7, 9, or 11. Examples of such proteins include: 1) isolated proteins which comprise an amino acid sequence with one or more amino acid substitutions, deletions, insertions, and/or additions in the amino acid sequence of SEQ ID NO: 7, 9, or 11, and which are functionally equivalent to the protein comprising the amino acid sequence of SEQ ID NO: 7, 9, or 11; and 2) isolated proteins which are encoded by DNAs that hybridize under stringent conditions with DNAs comprising the nucleotide sequence of SEQ ID NO: 8, 10, or 12, and which are functionally equivalent to the protein comprising the amino acid sequence of SEQ ID NO: 7, 9, or 11.

The HMGB3 protein of the present invention can be exemplified by, but is not limited to proteins comprising the amino acid sequence of SEQ ID NO: 13 or 15. HMGB3 proteins of the present invention can also include proteins which are functionally equivalent to the protein comprising the amino acid sequence of SEQ ID NO: 13 or 15. Examples of such proteins include: 1) isolated proteins which comprise an amino acid sequence with one or more amino acid substitutions, deletions, insertions, and/or additions in the amino acid sequence of SEQ ID NO: 13 or 15, and which are functionally equivalent to the protein comprising the amino acid sequence of SEQ ID NO: 13 or 15; and 2) isolated proteins which are encoded by DNAs that hybridize under stringent conditions with DNAs comprising the nucleotide sequence of SEQ ID NO: 14 or 16, and which are functionally equivalent to the protein comprising the amino acid sequence of SEQ ID NO: 13 or 15.

The S100A8 protein of the present invention can be exemplified by, but is not limited to proteins comprising the amino acid sequence of SEQ ID NO: 17, 19, or 21. S100A8 proteins of the present invention can also include proteins which are functionally equivalent to the protein comprising the amino acid sequence of SEQ ID NO: 17, 19, or 21. Examples of such proteins include: 1) isolated proteins which comprise an amino acid sequence with one or more amino acid substitutions, deletions, insertions, and/or additions in the amino acid sequence of SEQ ID NO: 17, 19, or 21, and which are functionally equivalent to the protein comprising the amino acid sequence of SEQ ID NO: 17, 19, or 21; and 2) isolated proteins which are encoded by DNAs that hybridize under stringent conditions with DNAs comprising the nucleotide sequence of SEQ ID NO: 18, 20, or 22, and which are functionally equivalent to the protein comprising the amino acid sequence of SEQ ID NO: 17, 19, or 21.

The S100A9 protein of the present invention can be exemplified by, but is not limited to, proteins comprising the amino acid sequence of SEQ ID NO: 23, 25, or 27. S100A9 proteins of the present invention can also include proteins which are functionally equivalent to the protein comprising the amino acid sequence of SEQ ID NO: 23, 25, or 27. Examples of such proteins include: 1) isolated proteins which comprise an amino acid sequence with one or more amino acid substitutions, deletions, insertions, and/or additions in the amino acid sequence of SEQ ID NO: 23, 25, or 27, and which are functionally equivalent to the protein comprising the amino acid sequence of SEQ ID NO: 23, 25, or 27; and 2) isolated proteins which are encoded by DNAs that hybridize under stringent conditions with DNAs comprising the nucleotide sequence of SEQ ID NO: 24, 26, or 28, and which are functionally equivalent to the protein comprising the amino acid sequence of SEQ ID NO: 23, 25, or 27.

Isolated proteins which are functionally equivalent to the protein comprising the amino acid sequence of SEQ ID NO: 1, 3, 5, 7, 9, 11, 13, 15, 17, 19, 21, 23, 25, or 27 may be homologues or paralogues to the protein comprising the amino acid sequence of SEQ ID NO: 1, 3, 5, 7, 9, 11, 13, 15, 17, 19, 21, 23, 25, or 27. Those skilled in the art can isolate proteins which are functionally equivalent to the protein comprising the amino acid sequence of SEQ ID NO: 1, 3, 5, 7, 9, 11, 13, 15, 17, 19, 21, 23, 25, or 27, by known methods (supplementary volume of "Jikken Igaku (Experimental Medicine), Idenshi Kougaku Handbook (Genetic Engineering Handbook)", pp 246-251, published by Yodosha Co., Ltd., 1991).

Examples of proteins which are functionally equivalent to the protein comprising the amino acid sequence of SEQ ID NO: 1, 3, 5, 7, 9, 11, 13, 15, 17, 19, 21, 23, 25, or 27 include proteins having bone marrow-derived cell-inducing activity.

Proteins which comprise an amino acid sequence with one or more amino acid substitutions, deletions, insertions, and/or additions in the amino acid sequence of SEQ ID NO: 1, 3, 5, 7, 9, 11, 13, 15, 17, 19, 21, 23, 25, or 27, and which are functionally equivalent to the protein comprising the amino acid sequence of SEQ ID NO: 1, 3, 5, 7, 9, 11, 13, 15, 17, 19, 21, 23, 25, or 27 include naturally-occurring proteins. Generally, eukaryotic genes have polymorphism as known in interferon genes and such. Alterations in nucleotide sequence caused by the polymorphism may result in one or more amino acid substitutions, deletions, insertions, and/or additions. Naturally-occurring proteins such as those comprising an amino acid sequence with one or more amino acid substitutions, deletions, insertions, and/or additions in the amino acid sequence of SEQ ID NO: 1, 3, 5, 7, 9, 11, 13, 15, 17, 19, 21, 23, 25, or 27, and which are functionally equivalent to the protein comprising the amino acid sequence of SEQ ID NO: 1, 3, 5, 7, 9, 11, 13, 15, 17, 19, 21, 23, 25, or 27 are included in HMGB1, HMGB2, HMGB3, S100A8, or S100A9 proteins of the present invention.

The present invention also includes artificially-produced mutant proteins as long as they are functionally equivalent to the protein comprising the amino acid sequence of SEQ ID NO: 1, 3, 5, 7, 9, 11, 13, 15, 17, 19, 21, 23, 25, or 27. Known methods which cause random mutations to a given nucleotide sequence include substitution(s) of base pair(s) through nitrous acid treatment of DNA (Hirose, S. et al., Proc. Natl. Acad. Sci. USA., 79: 7258-7260, 1982). This method enables random introduction of substitution(s) of base pair(s) into a specific segment by nitrous acid treatment of the segment desired to be mutated. Alternatively, technologies for site-directing a target mutation include the gapped duplex method (Kramer W. and Fritz H J., Methods in Enzymol., 154: 350-367, 1987) and the like. A cyclic double stranded vector in which a gene to be introduced with a mutation is cloned, is separated into single strands. These single strands are hybridized with a synthetic oligonucleotide mutated at the target site. A vector-derived complementary single strand DNA linearized by a restriction enzyme is annealed with the cyclic single stranded vector, and the gap between the oligonucleotide and the vector is filled by using a DNA polymerase, which is then made into a complete double stranded vector by ligation.

The number of amino acids to be modified would be typically within 50, preferably within 30, and more preferably within 5 amino acids (for example, one amino acid).

When an amino acid is artificially substituted, substitution with an amino acid having similar properties would result in maintaining the activity of the original protein. Proteins of the present invention include proteins resulting from a conservative substitution in the above substitution of amino acid(s), and which are functionally equivalent to the protein comprising the amino acid sequence of SEQ ID NO: 1, 3, 5, 7, 9, 11, 13, 15, 17, 19, 21, 23, 25, or 27. Conservative substitution is considered important when substituting amino acid(s) of domains important for protein activities. Such a conservative substitution of amino acid(s) is well known to those skilled in the art.

Examples of amino acid groups suitable for conservative substitution include basic amino acids (such as lysine, arginine, and histidine), acidic amino acids (such as aspartic acid and glutamic acid), uncharged polar amino acids (such as glycine, asparagine, glutamine, serine, threonine, tyrosine, and cysteine), nonpolar amino acids (such as alanine, valine, leucine, isoleucine, proline, phenylalanine, methionine, and tryptophane), β branched amino acids (such as threonine, valine, and isoleucine), and aromatic amino acids (such as tyrosine, phenylalanine, tryptophane, and histidine).

Moreover, non-conservative substitution may increase protein activities (for example, constitutively activated proteins).

In addition, proteins which are functionally equivalent to the protein comprising the amino acid sequence of SEQ ID NO: 1, 3, 5, 7, 9, 11, 13, 15, 17, 19, 21, 23, 25, or 27 can be obtained by methods that utilize hybridization. That is to say, a DNA encoding HMGB1, HMGB2, HMGB3, S100A8, or S100A9 protein of the present invention as shown in the SEQ ID NO: 2, 4, 6, 8, 10, 12, 14, 16, 18, 20, 22, 24, 26, or 28 or a fragment thereof is used as a probe, and then DNAs that can hybridize to them are isolated. A hybridization reaction performed under stringent conditions leads to the selection of highly homologous DNA as a nucleotide sequence. This increases the chances of isolated proteins containing proteins that are functionally equivalent to the HMGB1, HMGB2, HMGB3, S100A8, or S100A9 protein. Examples of a highly homologous nucleotide sequence include those having 70% or more, and desirably 90% or more identity.

In a specific example, the term "stringent conditions" refers to hybridization conditions with 6×SSC, 40% formamide at 25° C. and subsequent washing with 1×SSC at 55° C. The stringency depends on conditions such as salt concentration, formamide concentration, or temperature; however it is obvious for those skilled in the art to set these conditions so as to obtain necessary stringency.

With the use of hybridization, for example, DNAs encoding homologues of the HMGB1, HMGB2, HMGB3, S100A8, or S100A9 proteins other than those proteins comprising the amino acid sequence of SEQ ID NO: 1, 3, 5, 7, 9, 11, 13, 15, 17, 19, 21, 23, 25, or 27 can be isolated.

Proteins which are functionally equivalent to a protein comprising the amino acid sequence of SEQ ID NO: 1, 3, 5, 7, 9, 11, 13, 15, 17, 19, 21, 23, 25, or 27 normally have a high homology with the amino acid sequence of SEQ ID NO: 1, 3, 5, 7, 9, 11, 13, 15, 17, 19, 21, 23, 25, or 27. The term "high homology" refers to a sequence identity of at least 30% or more, preferably 50% or more, more preferably 80% or more (for example, 95% or more). The identity of the nucleotide sequences and amino acid sequences can be determined using a homology search site via the interne (For example, homology searches such as FASTA, BLAST, PSI-BLAST, and SSEARCH can be used in the DNA Data Bank of Japan (DDBJ) [examples of which include the homology search page (Search and Analysis) at the DNA Data Bank of Japan (DDBJ) website; http://www.ddbj.nig.ac.jp/E-mail/homology-j.html]). Furthermore, searches using BLAST can be carried out through the web site of the National Center for Biotechnology Information (NCBI) (examples of which include BLAST page at the homepage of NCBI website; http://www.ncbi.nlm.nih.gov/BLAST/; Altschul, S. F. et al., J. Mol. Biol., 1990, 215(3): 403-10; Altschul, S. F. & Gish, W., Meth. Enzymol., 1996, 266: 460-480; Altschul, S. F. et al., Nucleic Acids Res., 1997, 25: 3389-3402)).

For example, in the calculation of the identity of amino acid sequences using Advanced BLAST 2.1, the identity value (%) can be obtained by the following: blastp is used as the program, expect value is set at 10, all filters are set at OFF, BLOSUM62 is used for matrix, and gap existence cost, per residue gap cost, and lambda ratio are set at 11, 1, and 0.85, respectively (default parameters) (Karlin, S, and S. F.

Altschul (1990) Proc. Natl. Acad. Sci. USA 87: 2264-68; Karlin, S, and S. F. Altschul (1993) Proc. Natl. Acad. Sci. USA 90: 5873-7).

Proteins of the present invention, or proteins functionally equivalent thereto may be proteins subjected to various modifications such as physiological modification with sugar chains and the like, labeling with fluorescence or radioactive substances, or fusion with other proteins. Particularly in recombinants that will be described later, sugar chain modification may vary depending on the hosts used for expression. However, even if there is a difference in sugar chain modifications, all proteins having properties similar to those of HMGB1, HMGB2, HMGB3, S100A8, or S100A9 proteins disclosed herein are HMGB1, HMGB2, HMGB3, S100A8, or S100A9 proteins of the present invention or proteins functionally equivalent thereto.

HMGB1, HMGB2, HMGB3, S100A8, or S100A9 proteins can be obtained not only from living materials, but also in the form of recombinants by incorporating genes that encode these proteins into an appropriate expression system. In order to obtain HMGB1, HMGB2, HMGB3, S100A8, or S100A9 proteins by genetic engineering techniques, the above-mentioned DNAs which encode HMGB1, HMGB2, HMGB3, S100A8, or S100A9 proteins may be incorporated into an appropriate expression system, and they can then be expressed. Examples of host/vector systems applicable to the present invention include the expression vector pGEX and *E. coli*. With pGEX, foreign genes can be expressed as a fusion protein with glutathione-S-transferase (GST) (Gene, 67: 31-40, 1988). pGEX incorporated with a gene encoding the HMGB1, HMGB2, HMGB3, S100A8, or S100A9 protein is introduced into an *E. coli* strain such as BL21 by heat shock, incubated for an appropriate time and then isopropylthio-β-D-galactoside (IPTG) is added to induce the expression of GST-fused HMGB1, GST-fused HMGB2, GST-fused HMGB3, GST-fused S100A8, or GST-fused S100A9 proteins. Since GST of the present invention adsorbs onto Glutathione Sepharose 4B, the expression product is readily separated and purified by affinity column chromatography.

In addition, the following may also be applied as host/vector systems to obtain recombinants of HMGB1, HMGB2, HMGB3, S100A8, or S100A9 proteins. First, when bacteria are used as hosts, expression vectors for fusion proteins that utilize histidine-tag, HA-tag, a FLAG-tag, and the like are commercially available. Regarding yeasts, yeasts belonging to the genus *Pichia* are known to be effective for the expression of sugar chain-containing proteins. In terms of the addition of sugar chains, expression systems that utilize baculovirus vector with insect cells as a host are also useful (Bio/Technology, 6: 47-55, 1988). Further, using mammalian cells, transfection of a vector is carried out using promoters such as CMV, RSV, and SV40. Any of these host/vector systems can be used as an expression system of HMGB1, HMGB2, HMGB3, S100A8, or S100A9 proteins. Moreover, genes can also be introduced using viral vectors such as retrovirus vectors, adenovirus vectors, and adeno-associated virus vectors.

Thus obtained proteins of the present invention may be isolated intracellularly or extracellularly (medium and such), and can be purified as proteins that are substantially pure and homogenous. Proteins may be separated and purified using separation and purification methods which are commonly used in protein purification, and are not particularly limited. For example, proteins can be separated and purified by appropriately selecting and combining a chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Examples of chromatographies include affinity chromatography, ion-exchange chromatography, hydrophobic chromatography, gel filtration, reverse phase chromatography, and adsorption chromatography (Marshak et al., Strategies for Protein Purification and Characterization: A Laboratory Course Manual. Ed Daniel R. Cold Spring Harbor Laboratory Press, 1996). These chromatographies can be performed using liquid phase chromatographies such as HPLC and FPLC.

Moreover, proteins of the present invention are preferably substantially purified proteins. Here, the term "substantially purified" means that the protein purity of the present invention (proportion of the protein of the present invention in total protein components) is 50% or more, 60% or more, 70% or more, 80% or more, 90% or more, 95% or more, 100% or close to 100%. The upper limit for "close to 100%" depends on the purification techniques and analytical techniques of those skilled in the art, of which examples are 99.999%, 99.99%, 99.9%, 99%, and the like.

Moreover, a substantially purified protein includes any protein purified by any purification method as long as the protein purity is as mentioned above. Examples include, but are not limited to, proteins substantially purified by appropriately selecting and combining the above-mentioned chromatography columns, filters, ultrafiltration, salting out, solvent precipitation, solvent extraction, distillation, immunoprecipitation, SDS-polyacrylamide gel electrophoresis, isoelectric focusing electrophoresis, dialysis, recrystallization, and the like.

Cells where HMGB1, HMGB2, HMGB3, S100A8, or S100A9 proteins of the present invention are released or secreted basically include all types of tissue-derived cells in vivo. Cells which can be readily collected and cultured are exemplified by, but are not limited to, fibroblasts (such as normal skin fibroblasts and cell lines derived therefrom). Moreover, cells secreting HMGB1, HMGB2, HMGB3, S100A8, or S100A9 proteins can also be produced by the following manner. A vector is produced by inserting an HMGB1, HMGB2, HMGB3, S100A8, or S100A9 protein-encoding DNA, or an HMGB1, HMGB2, HMGB3, S100A8, or S100A9 protein-encoding DNA linked with a secretion signal-encoding DNA (ATG CAG ACA GAC ACA CTC CTG CTA TGG GTA CTG CTG CTG TGG GTT CCA GGT TCC ACT GGT GAC; SEQ ID NO: 29), into a known expression vector or a gene therapy vector. The produced vector is introduced into mammalian cells such as fibroblasts (such as normal skin fibroblasts and cell lines derived therefrom), insect cells, and other cells. Examples of secretion signal-encoding DNAs include, but are not limited to, DNAs with the above-described sequences. Furthermore, there are no particular limitations in the animal type from which these cells derive, although cells from the animal type of the target animal subjected to vector administration, cells from the target itself, or cells derived from a blood relative of the target subjected to vector administration are preferably used.

DNAs which encode HMGB1, HMGB2, HMGB3, S100A8, or S100A9 proteins of the inducers or tissue regeneration promoters of the present invention may be cDNAs, genomic DNAs, natural DNAs, or artificially-synthesized DNAs so long as they encode the HMGB1, HMGB2, HMGB3, S100A8, or S100A9 protein. DNAs which encode HMGB1, HMGB2, HMGB3, S100A8, or S100A9 proteins are normally administered in a form inserted in vectors.

Examples of the vectors of the present invention include, but are not limited to, plasmid vectors, retrovirus vectors, lentivirus vectors, adenovirus vectors, adeno-associated virus vectors, Sendai virus vectors, Sendai virus envelope vectors, and papilloma virus vectors. The vectors may contain promoter DNA sequences which effectively induce gene expression, factors that regulate gene expression, and molecules which are necessary for maintaining DNA stability.

In the present invention, the following vectors may also be used: partial peptides of HMGB1, HMGB2, HMGB3, S100A8, or S100A9 protein which have an activity of inducing bone marrow-derived cells; cells secreting these partial peptides; or vectors inserted with the DNAs encoding these partial peptides.

Hyaluronic acid (also called hyaluronan) is a glycosaminoglycan (mucopolysaccharide) in which the two sugars, N-acetylglucosamine and glucuronic acid, are connected and linked.

The chemical name is: [->3)-2acetamido-2deoxy-β-D-glucopyranosyl-(1->4)β-D-glucopyranosyluronic acid-(1->] n. Most natural hyaluronic acids are high-molecular-weight hyaluronic acids with a molecular weight of several hundred thousands. Meanwhile, low-molecular-weight hyaluronic acids with two to 14 sugars can be artificially produced. In the medical field, for example, sodium hyaluronate has been used for injection into the joint cavity. Methods for producing hyaluronic acids include methods in which hyaluronic acids are extracted and purified from products produced using *Streptococcus zooepidemicus*, a lactic acid bacterium, and methods in which hyaluronic acids are extracted and purified from chicken crest or such. Hyaluronic acids can be variously modified by esterification, periodate oxidation, isourea coupling, sulfation, and such. Hyaluronic acids can also crosslinked via ether or ester bridges. Such modifications stabilize hyaluronic acids against degradation, insolubilize them, make them into a spongy form, or confer them with the property to release substances in a sustained fashion. Meanwhile, CD44 is a hyaluronic acid receptor, and hyaluronic acids have chemotactic activity for mesenchymal stem cells that have CD44 on their cell surface.

Extracts of cells or tissues used in the methods of the present invention can be produced by methods comprising the step of immersing cells or tissues in a solvent.

Cells and tissues to be immersed in a solvent are not particularly limited, but include, for example, tissue-derived cells, cells of cell lines established from tissue-derived cells (including, but not limited to, for example, HeLa and HEK293), isolated cells, non-isolated cells (for example, cells in isolated tissues), and cells transfected with DNA encoding HMGB1, HMGB2, HMGB3, S100A8, or S100A9 protein. The above tissues may be any types of tissue, and include, but are not limited to, for example, live skin tissues and tissues obtained by biopsy (surgery) from the body (brain, lung, heart, liver, stomach, small and large intestines, pancreas, kidney, urinary bladder, spleen, uterus, testis, blood, etc.).

Examples of the above solvent include, but are not limited to, physiological saline, phosphate-buffered saline (PBS), and Tris-buffered saline (TBS). Moreover, the immersion time of cells or tissue in a solvent should be a duration necessary and sufficient for inducing cell necrosis, that is, 1 hour to 48 hours (such as 6 to 48 hours), and preferably 12 to 24 hours, but is not limited thereto. Therefore, the "step of immersing cells in a solvent" can be rephrased as a "step of immersing cells in a solvent for a duration necessary and sufficient for inducing necrosis" or "step of necrosing cells". Moreover, examples of the temperature for immersing cells or tissue in a solvent include, but are not limited to, 4° C. to 25° C. (such as 4° C. to 8° C.), and preferably 4° C. Further, examples of the pH for immersing cells or tissue in a solvent include, without limitation, pH 7 to 8, and preferably pH 7.5. Examples of the buffer include, without limitation, a phosphate buffer solution at a concentration of 10 mM to 50 mM, preferably 10 to 20 mM, but are not limited thereto.

Moreover, in the present invention, cells or tissues can be removed from a solvent containing them after they are immersed in the solvent. The method for removing cells or tissues from a solvent is not particularly limited as long as the method is well known to those skilled in the art. For example, cells or tissues can be removed from a solvent by centrifuging at a gravity acceleration of 10 G to 100,000 G (for example, 440 G) at 4° C. to 25° C. (for example, 4° C.), followed by separation of the supernatant, but the removal method is not limited thereto. The supernatant can be used as an extract of cells or tissues.

The extracts of cells or tissues of the present invention prepared by methods comprising the step of immersing cells or tissues in a solvent include, for example, skin extract and peripheral blood mononuclear cell extract (peripheral blood extract), but are not limited thereto.

The peripheral blood extract is prepared by the following method: after collecting blood with a syringe or the like, the cells are frozen in a freezer or liquid nitrogen, on dry ice, or such, and then thawed at a temperature of 0° C. or higher. Then, to remove insoluble cellular components, the sample is centrifuged, for example, at a gravity of 10 to 100,000 G (for example, at 440 G) and 4° C. to 25° C. (for example, at 4° C.), and the resulting supernatant is collected. The insoluble cellular components can be removed from the solvent by the method described above. However, methods for removing insoluble cellular components are not limited to the above example. The resulting supernatant can be used as an extract of cells or tissues. Alternatively, instead of centrifugation, insoluble cellular components can be removed by filtration through a nitrocellulose filter with micro pores of 0.45 μm, or the like. Alternatively, collected peripheral blood may be allowed to stand for three to 48 hours at 4° C. to induce cell necrosis. The intracellular components can be released from peripheral blood cells by this treatment. Then, to remove insoluble cellular components from the solvent, the sample is centrifuged at a gravity of 10 to 100,000 G (for example, at 440 G), and the resulting supernatant is collected. The insoluble cellular components can be removed from the solvent by the method described above, but are not limited thereto. The resulting supernatant can be used as an extract of cells or tissues. Alternatively, instead of centrifugation, insoluble cellular components can be removed by filtration through a nitrocellulose filter with micro pores of 0.45 μm of the like.

Heparin-binding fractions from the extracts of cells or tissues to be used in the present invention can be produced by a method comprising the following steps.
(a) immersing a cell or tissue in a solvent;
(b) contacting an extract obtained by the step (a) with immobilized heparin; and
(c) eluting a heparin-binding fraction (may also be expressed as heparin-purified fraction or heparin-column purified fraction) from the immobilized heparin.

"Immobilized heparin" refers to heparin covalently bound to an insoluble carrier. Examples of the insoluble carrier include, but are not limited to, Sepharose beads (such as Sepharose 4B, Sepharose 6B and such: GE Healthcare). In the present invention, a commercially available immobilized heparin (Hitrap Heparin HP column: GE Healthcare) may also be used.

Examples of conditions for contacting an extract of cells or tissues with immobilized heparin include, but are not limited to, about pH 7 to 8 (preferably pH 7.5), and a salt concentration of 0 to 200 mM, and preferably about 100 to 200 mM. The time the extract is in contact with immobilized heparin is not specifically limited, but the contact is preferably retained for 5 minutes or more in view of sufficient adsorption of the heparin-binding fraction onto immobilized heparin. Examples of the temperature include, but are not limited to, 4 to 8° C., and preferably 4° C. Further, examples of the elution condition of the heparin-binding fraction adsorbed onto the immobilized heparin include, but are not limited to, a pH of about 7 to 8 and a salt concentration of 200 to 1,000 mM (preferably about 1,000 mM).

Meanwhile, any of the materials of (a) to (r) described above or mixtures of any two or more of the materials, which are used in the methods of the present invention, include but are not limited to, for example, the combinations of: hyaluronic acid and HMGB1 protein; hyaluronic acid and HMGB2 protein; hyaluronic acid and HMGB3 protein; hyaluronic acid and S100A8 protein; hyaluronic acid and S100A9 protein; hyaluronic acid, and HMGB1 and HMGB2 proteins; hyaluronic acid, and HMGB2 and HMGB3 proteins; hyaluronic acid, and HMGB1 and HMGB3 proteins; hyaluronic acid, and HMGB1, HMGB2, and HMGB3 proteins; hyaluronic acid, and S100A8 and S100A9 proteins; hyaluronic acid, and HMGB1 and S100A8 proteins; hyaluronic acid, and HMGB2 and S100A8 proteins; hyaluronic acid, and HMGB3 and S100A8 proteins; hyaluronic acid, and HMGB1 and S100A9 proteins; hyaluronic acid, and HMGB2 and S100A9 proteins; hyaluronic acid, and HMGB3 and S100A9 proteins; hyaluronic acid and extracts of cells or tissues; and hyaluronic acid and heparin-binding fractions of cell or tissue extracts; and preferably mixtures of hyaluronic acid, and extracts of cells or tissues. The mixing ratio is based on the volume of the least amount of ingredient dissolved in a solvent which is taken as 1, where the other ingredients may be added in a volume up to 10,000 times greater, and preferably, the other ingredients may be added in a volume equal or up to 10 times greater when the least amount of ingredient is taken as 1.

The types of animals which serve as a source for an extract, heparin-binding fraction, HMGB1, HMGB2, HMGB3, S100A8, or S100A9 protein of the present invention include human and non-human animals, which can be exemplified by humans, mice, rats, monkeys, pigs, dogs, rabbits, hamsters, and guinea pigs, but the type of animal is preferably the same as the animal to be administered with the above extract or the like.

Extracts, heparin-binding fractions, HMGB1, HMGB2, HMGB3, S100A8, and S100A9 proteins of the present invention are administered to blood vessels or muscles by parenteral administration methods. Specifically, such administration methods include injection. For example, the pharmaceutical agents of the present invention can be administered to blood vessels, muscles, or under the skin (for example, into or near the vessel implanted under the skin) by intravascular injection (intraarterial injection, intravenous injection, etc.), intramuscular injection, subcutaneous injection, and the like. Alternatively, the agents of the present invention may be allowed to absorb in a sustained-release manner using transdermal absorbable patches or external preparations.

The method of administration may be appropriately selected according to the age and the symptoms of the subject. When an HMGB1, HMGB2, HMGB3, S100A8, or S100A9 protein is administered, the dose per time of the protein can be selected within a range of 0.0000001 mg to 1,000 mg per kg body weight of a subject. Alternatively, the dose can be selected within a range of 0.00001 mg to 100,000 mg per body of subject, for example. When administering cells secreting HMGB1, HMGB2, HMGB3, S100A8, or S100A9 proteins or gene therapy vectors inserted with DNAs encoding HMGB1, HMGB2, HMGB3, S100A8, or S100A9 proteins they may be administered such that the amounts of HMGB1, HMGB2, HMGB3, S100A8, or S100A9 protein in the damaged tissues are within the above range. However, the dosage of extracts, heparin-binding fractions, or HMGB1, HMGB2, HMGB3, S100A8, or S100A9 proteins of the present invention is not limited thereto.

When administered, extracts, heparin-binding fractions, or HMGB1, HMGB2, HMGB3, S100A8, or S100A9 proteins can be formulated according to the usual methods (for example, Remington's Pharmaceutical Science, latest edition, Mark Publishing Company, Easton, U.S.A), and may contain pharmaceutically acceptable carriers and additives together. Examples include surfactants, excipients, colorants, perfumes, preservatives, stabilizers, buffers, suspending agents, isotonizing agents, binders, disintegrants, lubricants, flow promoters, and flavoring agents, although they are not limited thereto and other common carriers may be appropriately used. Specific examples include light anhydrous silicic acid, lactose, crystalline cellulose, mannitol, starch, carmellose calcium, carmellose sodium, hydroxypropylcellulose, hydroxypropylmethylcellulose, polyvinylacetaldiethylamino acetate, polyvinylpyrrolidone, gelatin, medium-chain fatty acid triglyceride, polyoxyethylene hydrogenated castor oil 60, white sugar, carboxymethyl cellulose, corn starch, and inorganic salts.

Extracts, heparin-binding fractions, HMGB1, HMGB2, HMGB3, S100A8, or S100A9 protein of the present invention can be placed into a vessel by injection using the following method. Specifically, each solution or solute is dissolved in physiological saline, and the resulting solution is manually injected using an injector or pipette. Alternatively, the solution is mechanically injected into a tube at the time of tube production.

Meanwhile, the amount of extracts, heparin-binding fractions, HMGB1, HMGB2, HMGB3, S100A8, or S100A9 protein of the present invention to be injected into a vessel is determined appropriately according to the volume of the vessel used for cell collection. For example, when the vessel is implanted into abdominal subcutaneous adipose, it is possible to inject about 10 ml of an agent of the present invention. Alternatively, when the vessel is implanted under non-abdominal skin, the amount of injection is expected to be approximately several milliliters.

The present invention provides cell populations collected by the above-described methods for harvesting cell population.

The present invention also provides bone marrow cells collected by the above-described methods for harvesting bone marrow cells.

Cell populations and bone marrow cells of the present invention can be administered to treat diseases with tissue damage such as hereditary diseases, skin diseases (thermal injury, cutaneous ulcer, or such), brain and nerve diseases (brain infarction, Alzheimer's disease, spinal cord injury, brain injury, or such), cardiovascular diseases (myocardial infarction, cardiac myopathy, arterial embolism, or such), and osteocartilaginous diseases (bone fracture, rheumatism, or such). Tissues can be regenerated by directly administering the cells into blood circulation via a vein or artery, or by directly administering the cells into tissues at the damaged site immediately after cell harvest. Alternatively, tissues can be regenerated by administering cells in a dispersed or aggregated state, or when they are formed in a sheet shape after the cells are cultured using culture dishes or flasks. With regard to the amount of administration, 1 to $10^{14}$ cells, and preferably $10^2$ to $10^{10}$ cells can be administered. Thus, the present invention also provides tissue-regenerating agents comprising a cell population harvested by the above-described methods for harvesting cell populations or bone marrow cells harvested by the above-described methods for harvesting bone marrow cells.

The type of tissues to be regenerated is not particularly limited. The target tissue may be any tissue, as long as it is a damaged tissue. Such tissues include, for example, live skin tissues and tissues obtained by biopsy (surgery) from the body (brain, lung, heart, liver, stomach, small and large intestines, pancreas, kidney, urinary bladder, spleen, uterus, testis, blood, and such). In particular, the agents of the present invention are effectively used to regenerate tissues that are difficult for direct administration of agents from outside of the body (brain, heart, or such). In the present invention, damaged tissues include tissues damaged due to various pathological conditions such as those that result in ischemia, hemostasis or hypoxia, trauma, burn, inflammation, autoimmunity, genetic abnormalities, and such, but are not limited to these examples. Furthermore, damaged tissues include necrotic tissues.

Tissues of the present invention are not particularly limited, as long as they are differentiable from bone marrow cells. Such tissues include, for example, all biological tissues such as skin tissues, bone tissues, cartilage tissues, muscle tissues, adipose tissues, myocardial tissues, nerve tissues, lung tissues, gastrointestinal tissues, liver tissues, gallbladder tissues, pancreatic tissues, and urogenital system. Furthermore, the above-described tissue-regenerating agents can be used to treat not only skin diseases such as intractable cutaneous ulcer, skin wounds, bullosis, and alopecia, but also tissue damages such as those that are due to brain infarction, myocardial infarction, bone fracture, pulmonary infarction, gastric ulcer, and enteritis. The species of animals to be administered with the above-described tissue-regenerating agents include, but are not limited to human and non-human animals, for example, humans, mice, rats, monkeys, pigs, dogs, rabbits, hamsters, and guinea pigs. Furthermore, the agents of the present invention can be administered to diabetes patients. It is known that intractable cutaneous ulcer which is a complication of diabetes is difficult to treat as compared to cutaneous ulcer in normal persons. The agents of the present invention are also effectively used for such diabetes patients.

Following cell harvest, the cells are diffused in physiological saline, and the resulting cell suspension can be administered as a tissue-regenerating agent of the present invention into circulatory blood flow such as a vein or artery to achieve tissue regeneration. Alternatively, the tissue-regenerating agent of the present invention may be applied or plastered onto the surface of a tissue damage site to achieve tissue regeneration. Alternatively, the agent may be injected into the damaged site using a syringe or the like to achieve tissue regeneration. Alternatively, the cells may be cultured using culture dishes or flasks, and then administered to the damaged site in a diffused or aggregated state, or when they are formed in a sheet shape, to achieve tissue regeneration. With regard to the amount of administration, 1 to $10^{14}$ cells, and preferably $10^2$ to $10^{10}$ cells can be administered.

All prior art documents cited herein are incorporated by reference herein.

EXAMPLES

Hereinbelow, the present invention will be specifically described with reference to the Examples, but it is not to be construed as being limited thereto.

Example 1

Purpose: To develop novel highly efficient and minimally invasive techniques for collecting functional cells such as stem cells which exist in an extremely low number in vivo.

Methods: Studies were conducted to achieve the above purpose.

(1) After irradiating at 10 Gy, eight-week-old mice (male) were transplanted via the caudal vein with bone marrow cells ($5 \times 10^6$ cells/0.1 ml of phosphate buffered saline, pH 7.4) derived from green fluorescent protein (GFP) transgenic mice to prepare GFP bone marrow-transplanted mice.

Figure 1:
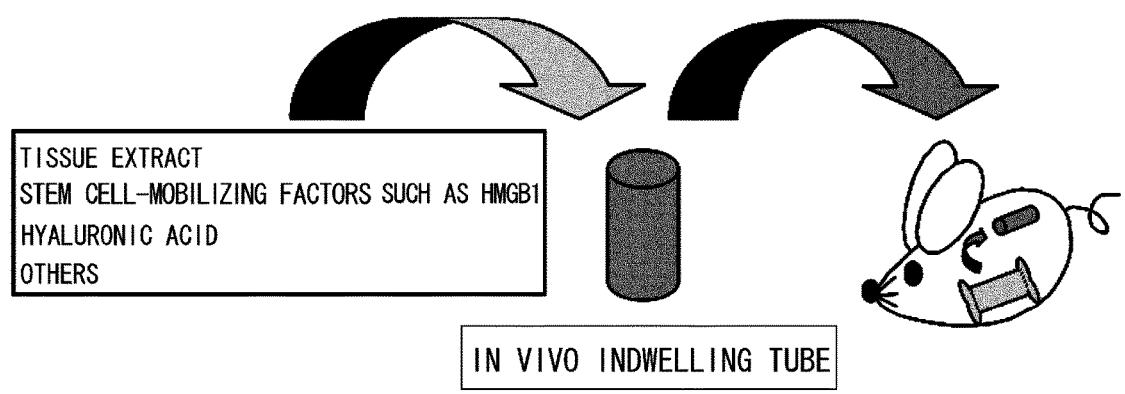
FIG. 1 shows in a schematic diagram a high-efficiency method for collecting biologically functional cells. A hypoallergenic tube (silicone tube or such) filled with a factor that specifically mobilizes biologically functional cells is placed in the body. As a result, functional cells are selectively mobilized into the tube from the peripheral blood circulation or tissue.

(2) Tubes made of biologically hypoallergenic material (silicone) were filled with HMGB1, hyaluronic acid, skin extract, or phosphate buffered saline (pH 7.4), and then implanted under the dorsal skin of GFP bone marrow-transplanted mice (FIG. 1).

Figure 2:
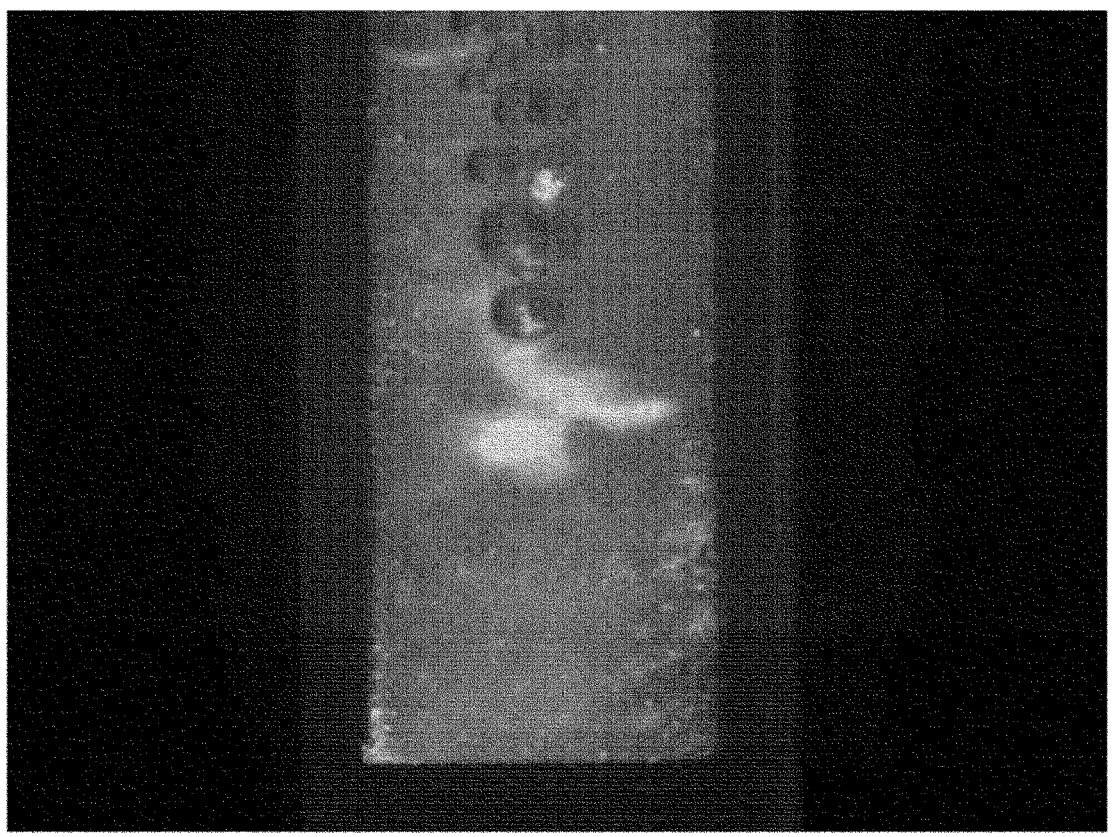
FIG. 2 shows in a photograph that cells accumulated in a tube (tube-entrapping cells; TECs) are GFP-positive.

(3) The implanted tubes were removed two weeks after implantation (FIG. 2). Cells accumulated in the tubes (tube-entrapping cells (TECs)) were collected and then cultured in Dulbecco's medium (D-MEM) supplemented with 10% fetal bovine serum at 37° C. under 5% carbon dioxide gas.

(4) When the culture density of TECs reached about 80% confluent on the bottom surface of culture dish, the culture medium was changed with a bone differentiation-inducing medium, adipose differentiation-inducing medium, or epidermis differentiation-inducing medium. Then, the cells were further cultured. Two weeks after the start of culture in each differentiation-inducing medium, differentiation into bone, adipose, and epidermis was assessed by alizarin red staining, oil red staining, and immunostaining for keratin 5, respectively.

(5) The proportion of platelet-derived growth factor receptor α and CD44 double-positive cells to TECs was analyzed by flow cytometry.

Figure 3:
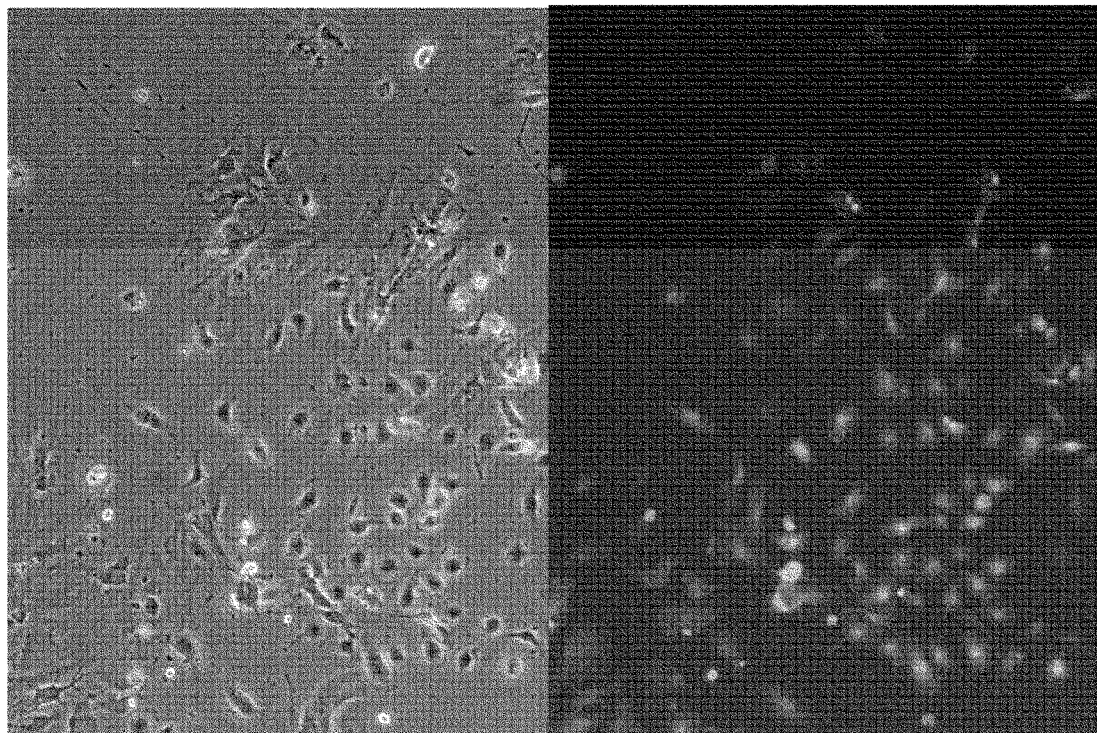
FIG. 3 shows in a set of photographs TECs 24 hours after start of culture. Left photograph shows a light-field image of proliferating fibroblast-like cells and epithelial cell-like cells adhering to a plastic culture dish. Right photograph shows a GFP fluorescence image of the dark field.
Figure 4:
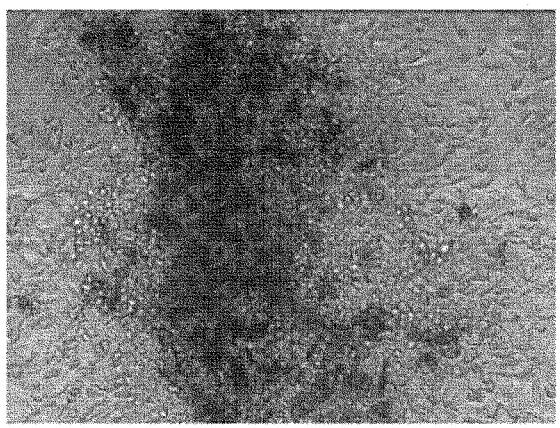
FIG. 4 shows in a set of photographs assessment of TECs collected from a tube for their ability to differentiate into osteoblasts. Cells harvested from the tube were cultured in an osteoblast differentiation-inducing culture medium and were confirmed to differentiate into osteoblasts positive for alizarin red stain in about two weeks.
Figure 4:
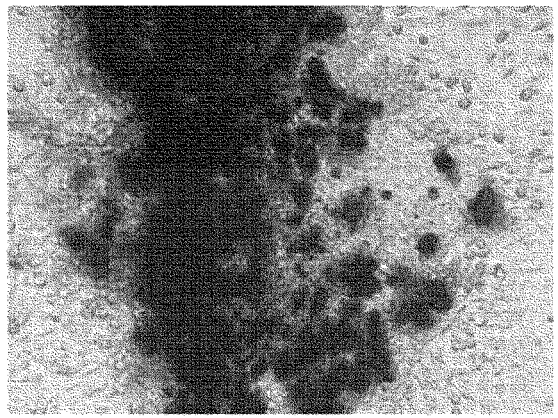
Figure 5:
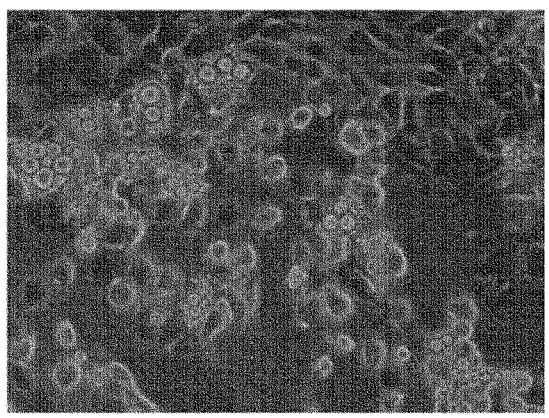
FIG. 5 shows in a set of photographs assessment of TECs collected from a tube for their ability to differentiate into adipocytes. Cells harvested from the tube were cultured in an adipocyte differentiation-inducing culture medium and were confirmed to differentiate into adipocytes positive for oil red stain in about two weeks.
Figure 5:
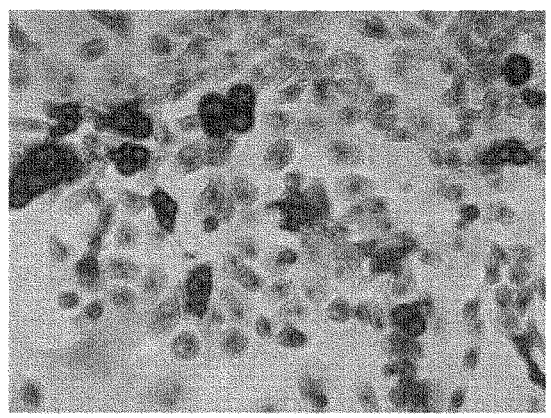
Figure 6:
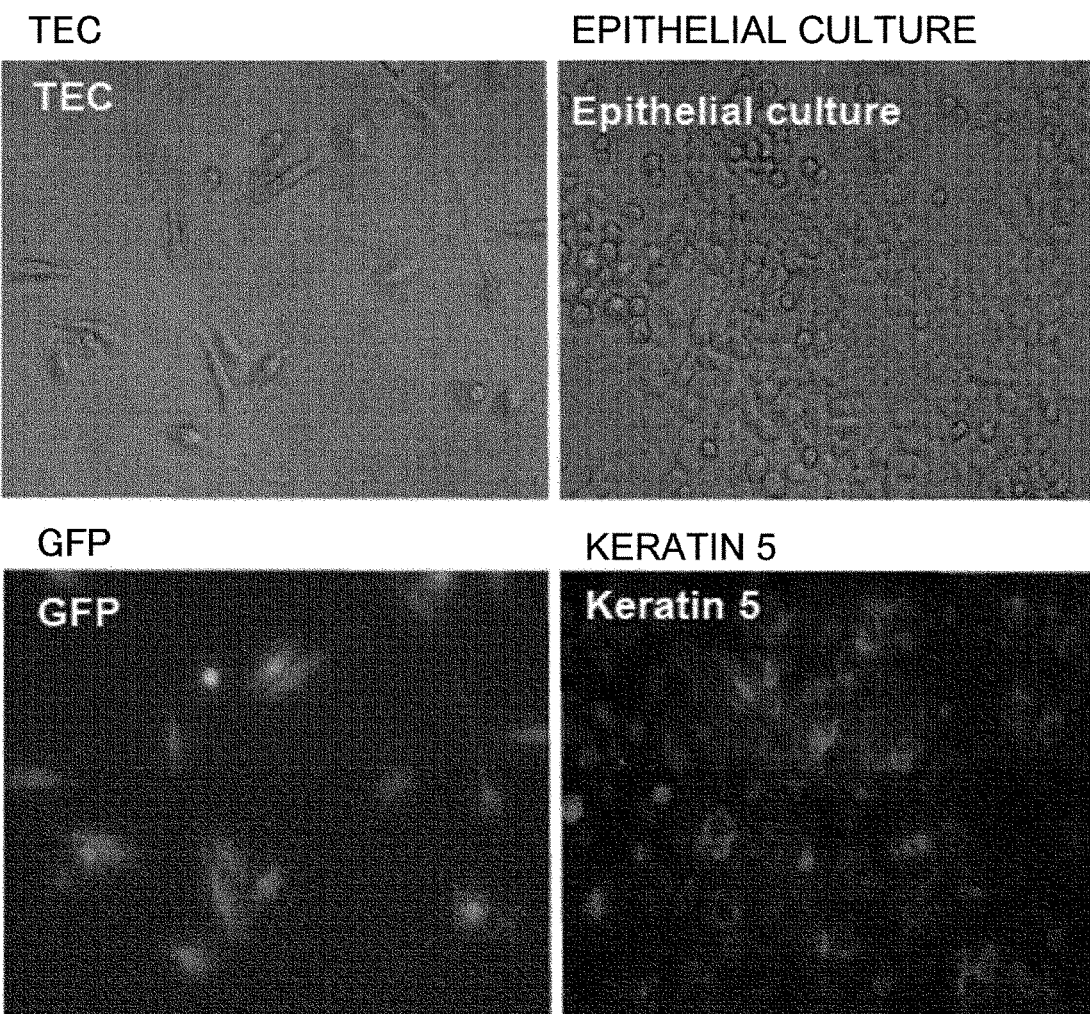
FIG. 6 shows in a set of photographs assessment of TECs collected from a tube for their ability to differentiate into epidermal cells. Cells collected from the tube were cultured in an epidermal cell differentiation-inducing culture medium and were confirmed to differentiate into epidermal cells expressing keratinocyte-specific keratin 5 in about two weeks.
Figure 7:
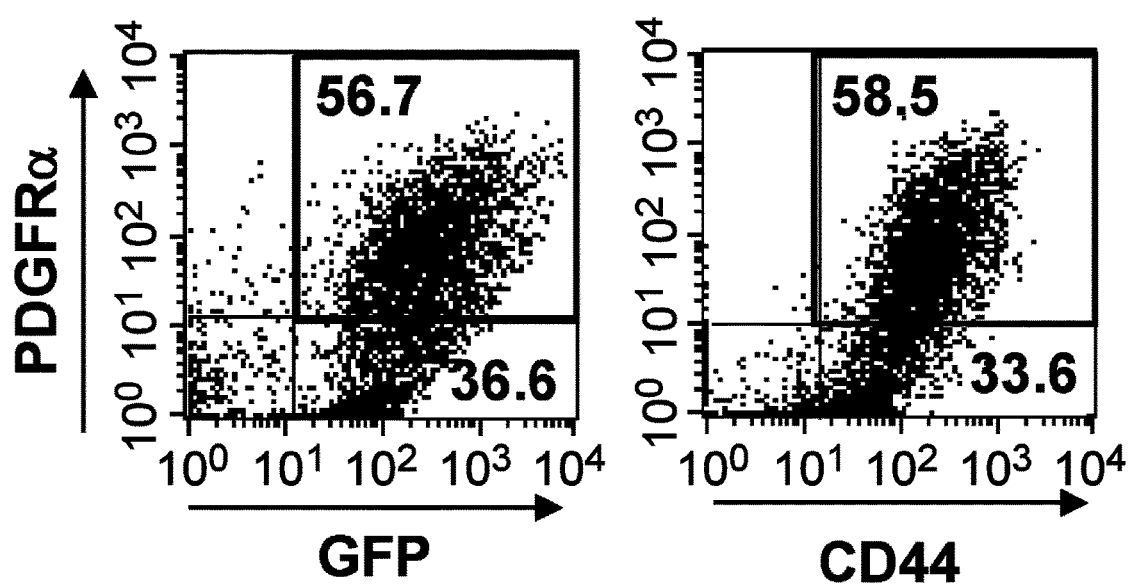
FIG. 7 shows in a set of diagrams assessment of the expression of PDGFRα and CD44 on TECs. Collection of PDGFRα and CD44 double-positive cells in the tube was confirmed.

Results: Silicone tubes filled with HMGB1, hyaluronic acid, or skin extract were implanted under the skin of GFP bone marrow-transplanted mice. As a result, when the tubes were filled with any of these solutions, a large number of GFP-positive bone marrow-derived cells (TECs) were accumulated in the tubes in one week. An image of GFP-positive cells accumulated in a silicone tube filled with HMGB1 is shown in FIG. 2. Meanwhile, the number of adhesive TECs in the silicone tubes filled with phosphate buffer was significantly smaller. When cells collected from silicone tubes filled with HMGB1 were cultured, proliferating adherent TECs were observed to be adhered to the culture dish 24 hours after the start of culture (FIG. 3). Adherent TECs that had migrated into silicone tubes filled with HMGB1 were cultured in a bone differentiation-inducing medium, adipose differentiation-inducing medium, or epidermis differentiation-inducing medium. The result showed that the cells had the ability to differentiate into alizarin red-positive osteoblasts, oil red-positive adipocytes, and keratin 5-positive epidermal cells, and thus among adherent TECs exist cell populations capable of mesenchymal and epithelial differentiation (FIGS. 4 to 6). Furthermore, the expression of PDGFRα and CD44 on TECs was assessed by flow cytometry. PDGFRα and CD44 are known to be expressed on the surface of mesenchymal stem cells. The result showed that about 60% of TECs were positive for both PDGFRα and CD44 (FIG. 7).

In addition, tubes filled with hyaluronic acid at 100 ng/ml (in PBS) were implanted under the dorsal skin of GFP bone marrow-transplanted mice. After two weeks, the tubes were removed and cells mobilized into the tubes were analyzed for their surface markers by FACS. The results were similar to that obtained with TECs isolated from HMGB1 tubes, and demonstrated that about 60% of the cells were P44 cells positive for both CD44 and PDGFRα and had the ability to differentiate into mesenchymal cells and epithelial cells such as osteoblasts and adipocytes.

Discussion: In the present invention, the present inventors revealed that bone marrow-derived TECs having the ability to differentiate into bone, adipose, and epidermis could be very efficiently collected by implanting under the skin, silicone tubes filled with HMGB1, hyaluronic acid, or skin extract. The following findings suggest that mesenchymal stem cells are selectively mobilized to TECs: most of the bone marrow-derived TECs express PDGFRα and CD44 which are known to be expressed on the surface of mesenchymal stem cells; and HMGB1, hyaluronic acid, and skin extract all have the activity of mobilizing mesenchymal stem cells. By selecting a solution for filling the silicone tube, specific biologically functional cells can be selectively harvested with high efficiency according to the substance contained in the solution, which is responsible for mobilizing the specific biologically functional cells. This novel technique of the present invention enables one to collect desired biologically functional cells without using highly invasive methods such as inserting a needle into the bone marrow. Thus, the technique is expected to enable the designing of order-made regenerative medical techniques according to the purpose. Furthermore, collected cells can be provided as materials for various types of basic studies including stem cell research. Thus, the present inventors believe that the present invention contributes largely to the development of basic and clinical studies, as well as drug discovery and progress of medical technologies.

Example 2

Purpose: To assess the therapeutic effect of bone marrow-derived cells mobilized into hypodermal device on skin ulcer Methods:

(1) Devices to be implanted into the body were prepared.

(2) To prepare skin tissue extract containing factors that mobilize bone marrow pluripotent stem cells, free skin pieces were isolated from two heads of C57/BL6 neonatal mice (two-day-old) and immersed in 2 ml of phosphate buffered saline (PBS), pH 7.4. After 24 hours of incubation at 4° C., the sample was centrifuged at 440 G and 4° C. for ten minutes to remove the tissues. The resulting supernatant was collected as skin extract. Furthermore, to prepare peripheral blood mononuclear cell extract, peripheral whole blood was collected from two heads of 4-week-old C57/BL6 mice and then diluted with PBS to a total volume of 4 ml. After placing 3 ml of Ficoll-Paque Plus (GE) in a centrifuge tube, the diluted blood was overlaid onto the Ficoll layer. The tube was centrifuged at 100 G at 18° C. for ten minutes. The resulting middle layer containing mononuclear cells was transferred into a fresh centrifuge tube. To remove Ficoll-Paque Plus from the collected middle layer, 45 ml of PBS was added and the resulting mixture was centrifuged at 440 G at 18° C. for five minutes. The supernatant was removed, and again 45 ml of PBS was added, and the suspension was centrifuged at 440 G at 18° C. for five minutes. The supernatant was removed, and the precipitated cells were suspended in 200 µl of PBS. The cell suspension was frozen in a freezer at −80° C. for 30 minutes, and then transferred onto ice for thawing. This freeze-thaw treatment was repeated three times. The sample was centrifuged at 440 G at 4° C. for 15 minutes. The resulting supernatant was collected (peripheral blood extract).

(3) Male C57/BL6 mice (six to eight weeks old) were irradiated at a lethal dose (10 Gy). Immediately after irradiation, green fluorescent protein (GFP) transgenic mouse-derived bone marrow cells ($5 \times 10^6$ cells/0.1 ml of phosphate buffered saline, pH 7.4) were transplanted to the mice via the caudal vein. Only mice that had survived for eight weeks after transplantation were used in subsequent experiments.

(4) 40 µl of the skin extract and peripheral blood extract prepared as described in (2), or PBS as a negative control were each inserted into the devices. A pair of devices was implanted into the mice as prepared in (3) (a total of two devices per head). The devices were placed under the dorsal skin: one was placed on the right and the other on the left, arranged so that their openings were in contact with the fascia. Two weeks after implantation, the devices were removed from the mice.

(5) After removing dorsal hair from eight-week-old C.B-17/lcr-scid/scidJcl (Charles River Japan, Inc), round-shaped cutaneous ulcers with a diameter of 6 mm were formed on either side of the back. To prevent shrinkage of mouse skin, a silicone disc with an outer diameter of 10 mm, inner diameter of 6 mm, and thickness of 1 mm was adhered to the ulcer site using two-sided adhesive tape and medical adhesive, Aron alpha A (Sankyo). Cells were collected from the inside of either one of the left and right devices removed as described in (3) and administered to the cutaneous ulcer. A silicone disc with a diameter of 10 mm and thickness of 1 mm was placed over the ulcer to prevent desiccation and bacterial infection. Then, the ulcer was covered with Tegaderm (3M) for protection. The area of the ulcer was measured after seven days (FIG. 27).

As a result, the negative control ulcer was not closed at the surface even after seven days. Meanwhile, in the ulcer administered with cells collected with the blood extract, reduction of the ulcer surface area was observed on day 5. On the other hand, when administered with cells collected using the skin extract, the ulcer was found to be closed on the surface on day 7 (FIG. 27).

This example demonstrated that when administered to cutaneous ulcer lesions, bone marrow-derived cells mobilized into an in vivo implantation device that contains tissue extract produced a therapeutic effect on the ulcer. The therapeutic method of the present invention which uses bone marrow cells mobilized into implanted devices but does not collect bone marrow cells from the bone marrow is an entirely novel therapeutic method.

Example 3

(1) Skin extract and peripheral blood extract were prepared by the method described above in Example 2.

1-ml HiTrap Heparin HP columns (GE) were equilibrated with 10 ml of 10 mM phosphate buffer (pH 7.5). Each skin extract and peripheral blood extract was diluted with ten volumes of 10 mM phosphate buffer (pH 7.5) and loaded onto equilibrated columns. To wash off non-specifically adsorbed materials, the columns were washed with 10 ml of 10 mM phosphate buffer (pH 7.5). The adsorbed components were eluted with 10 mM phosphate buffer (pH 7.5) containing 1,000 mM NaCl, and aliquoted (120 µl) into plastic tubes. The protein contents were determined using a protein assay kit (Bio-Rad), and three fractions with the highest protein concentration were recovered (heparin-adsorbed tissue extract).

(2) 10 µl of PBS containing 0.1% hyaluronic acid was combined with 40 µl of the tissue extract. The resulting mixture was added into the devices described in Example 2. A mixture of hyaluronic acid and 10 mM phosphate buffer (pH 7.5) containing 1,000 mM NaCl was used as negative control.

(3) GFP bone marrow-transplanted mice were prepared by the same method as described in Example 2. The devices prepared as described in (2) were implanted under the dorsal skin of the mice. Ten days after implantation, the devices were removed from under the skin and cells were collected from the devices. The collected cells were cultured in culture dishes containing IMDM (Invitrogen) supplemented with 10% fetal bovine serum at 37° C. under an atmosphere of 5% $CO_2$. To remove non-adherent cells, the medium was changed one day after the start of culture. Then, the medium was changed every three days. One week after cell harvest, the cells were observed under a fluorescence microscope to detect bone marrow-derived cells (GFP-positive cells) (FIG. 28). Furthermore, the number of GFP-positive cells was determined using an image analysis software (Image J) (FIG. 29).

The mixture of hyaluronic acid and heparin-binding fraction of tissue extract (blood extract (FIG. 28C), and skin extract (FIG. 28D)) were demonstrated to have a strong activity of mobilizing bone marrow-derived adherent cells into the device (FIGS. 28 and 29), as compared to PBS (FIG. 28A) or hyaluronic acid alone (FIG. 28B).

This Example demonstrates that bone marrow cell-mobilizing factors can be purified from tissue extracts using heparin columns. Skin extract contains HMGB1, HMGB2, HMGB3, S100A8, and S100A9. These components bind to heparin columns, suggesting the possibility that these cells are involved in the mobilization of bone marrow cells. Alternatively, since various cytokines such as growth factors also bind to heparin columns, it is thought that the net effect of the various factors is responsible for the mobilization of bone marrow cells.

Example 4

(1) RNA was extracted from neonatal mouse skin using Trizol (Invitrogen), and then cDNA was synthesized from the RNA using the SuperScript III cDNA Synthesis Kit (Invitrogen). S100A8 cDNA was amplified by the polymerase chain reaction (PCR) method using the synthesized cDNA as a template. For purification, S100A8 cDNA was inserted into the mammalian cell protein-expression plasmid vector pCAGGS to be expressed as a protein having Flag-tag and 6×His-tag sequences at the N terminus of the amino acid sequence. pCAGGS-Flag-His-S100A8 was transfected into a human fetal kidney cell-derived cultured cell line HEK293 using polyethyleneimine (PEI). After 48 hours, the cells and culture supernatant were separately collected by centrifugation at 4,400 G and 4° C. for five minutes. Then, the collected supernatant was filtered through a cellulose acetate filter having pores with a diameter of 0.8 µm (Nalgene) and then through a nitrocellulose filter having pores with a diameter of 0.45 µm (Corning) to prepare a sample removed of insoluble fractions. The sample was loaded onto 5-ml HisTrap FF (GE) equilibrated with 50 ml of 50 mM Tris HCl (pH 8.0) containing 50 mM NaCl, and then the adsorbed components were washed with 50 mM Tris HCl (pH 8.0) containing 50 mM NaCl and 10 mM imidazole to remove nonspecifically adsorbed components. The adsorbed specific components were eluted from the column using 50 mM Tris HCl (pH 8.0) containing 50 mM NaCl and 100 mM imidazole. The adsorbed fractions were fractionated into silicone-coated plastic tubes (500 µl/tube). Protein-containing fractions were combined together and mixed with anti-Flag Antibody M2 Beads (Sigma). The mixtures were incubated at 4° C. for 12 hours with gentle mixing. After incubation, the beads were centrifuged at 440 G for five minutes. After removing the supernatant, the beads were resuspended in PBS and centrifuged in the same way. The supernatant was removed. The beads were loaded onto a 3-ml column with an inner diameter of 1 cm, and the adsorbed protein was eluted from the column using 100 mM glycine (pH 3.5). The eluate was neutralized with a 1/10 volume of 500 mM Tris HCl (pH 7.5). The purified protein was quantified using a protein assay kit (Bio-Rad).

(2) RNA was extracted from neonatal mouse skin using Trizol (Invitrogen), and then cDNA was synthesized from the RNA using the SuperScript III cDNA Synthesis Kit (Invitrogen). HMGB1 cDNA was amplified by the polymerase chain reaction (PCR) method using the synthesized cDNA as a template. For purification, HMGB1 cDNA was inserted into the mammalian cell protein-expression plasmid vector pCAGGS to be expressed as a protein having Flag-tag and 6×His-tag sequences at the N-terminus of the amino acid sequence. pCAGGS-Flag-His-S100A8 was transfected into a human fetal kidney cell-derived cultured cell line HEK 293 using polyethyleneimine (PEI). After 48 hours, the cells and culture supernatant were separately collected by centrifuging at 4,400 G at 4° C. for five minutes. Then, the collected supernatant was filtered through a cellulose acetate filter having pores with a diameter of 0.8 µm (Nalgene) and then through a nitrocellulose filter having pores with a diameter of 0.45 µm (Corning) to prepare a sample removed of insoluble fractions. The sample was loaded onto 5-ml HisTrap FF (GE) equilibrated with 50 ml of 50 mM Tris HCl (pH 8.0) containing 50 mM NaCl, and then the absorbed components were washed with 50 mM Tris HCl (pH 8.0) containing 50 mM NaCl and 10 mM imidazole to remove nonspecifically adsorbed components. The adsorbed specific components were eluted from the column using 50 mM Tris HCl (pH 8.0) containing 50 mM NaCl and 100 mM imidazole. The adsorbed fractions were fractionated into silicone-coated plastic tubes (500 µl/tube). Protein-containing fractions were combined together, and then imidazole was removed using a desalting column PD10 (GE). The fractions were eluted using 50 mM Tris HCl (pH. 7.5) containing 150 mM NaCl. HRV3C (Novagen) was added to the eluted samples and the mixture was incubated at 4° C. for three hours. After cleavage, the sample was loaded onto a 1-ml HiTrap Heparin column (GE) equilibrated with 50 mM Tris HCl (pH 7.5) containing 150 mM NaCl. The inside of the column was washed with 50 mM Tris HCl (pH 7.5) containing 150 mM NaCl. The protein bound to the column was eluted with 50 mM Tris HCl (pH 7.5) containing 1,000 mM NaCl. The eluted sample was aliquoted to silicone-coated plastic tubes (500 µl/tube).

(3) 40 µg each of S100A8, HMGB1, HMGB2, and HMGB3 were added into silicone devices. The devices were implanted under the right and left dorsal skin so that the openings of devices were in contact with the fascia. Ten days after implantation, the devices were removed from under the skin, and cells accumulated in the devices were collected from the devices. The cells were cultured in culture dishes containing IMDM (Invitrogen) supplemented with 10% fetal bovine serum at 37° C. under an atmosphere of 5% $CO_2$. To remove non-adherent cells, the medium was changed one day after the start of culture. Then, the medium was changed every three days. One week after cell collection, the cells were observed under a fluorescence microscope to detect bone marrow-derived cells (GFP-positive cells) (FIG. 30).

(4) Round-shaped cutaneous ulcers with a diameter of 6 mm were formed on the back (left and right sides) of eight-week-old BALB/cAJcl-nu/nu (Charles River Japan, Inc). To prevent shrinkage of the mouse skin, a silicone disc with an outer diameter of 10 mm, inner diameter of 6 mm, and thickness of 1 mm was adhered to the ulcer site using two-sided adhesive tape and medical adhesive, Aron alpha A (Sankyo).

(5) The cells described in (3) were detached from the culture dishes by treatment with a solution containing 0.5 g/l Trypsin and 0.53 mmol/l EDTA (Nacalai Tesque). After inactivating trypsin with IMDM containing 10% FBS, the cells were centrifuged at 440 G at 4° C. for five minutes. After removing the supernatant, the cells were administered to the ulcer formed as described in (4). A silicone disc with a diameter of 10 mm and thickness of 1 mm was placed over the ulcer to prevent desiccation and bacterial infection at the site. Then, the ulcer was also covered with Tegaderm (3M) for protection. The area of the ulcer was measured seven days after administration (FIG. 31).

All of S100A8, HMGB1, HMGB2, and HMGB3 exhibited the activity of mobilizing bone marrow cells (FIG. 30; A, S100A8; B, HMGB1; C, HMGB2; D, HMGB3) as compared to the negative control (E). In particular, HMGB1 and HMGB2 showed stronger mobilizing activity.

Furthermore, cutaneous ulcer was treated by administering bone marrow-derived cells mobilized by HMGB1, HMGB2, or S100A8. The effect of reducing ulcer (FIG. 31) was observed as compared to the negative control (PBS-administered).

This Example demonstrated that all of S100A8, HMGB1, HMGB2, and HMGB3 exhibited the activity of mobilizing bone marrow-derived adherent cells into the device. Major cells in the bone marrow are hematopoietic cells such as erythrocytes and hemocytes and most of the cells are non-adherent cells. Meanwhile, mesenchymal cells such as mesenchymal stem cells are known as adherent cells. Such cells are speculated to include pluripotent cells capable of differentiating into epithelial and nerve cells. Since this Example demonstrated that cells mobilized into the device using S100A8, HMGB1, or HMGB2 exerted therapeutic effect on cutaneous ulcer, the cells mobilized into the devices are bone marrow-derived cells capable of inducing healing of tissue damages. It has been reported that bone marrow mesenchymal stem cells produced therapeutic effect when administered to lesions of cutaneous ulcer (Mesenchymal stem cells enhance wound healing through differentiation and angiogenesis. Wu Y, Chen L, Scott P G, Tredget E E. Stem Cells 2007 October; 25(10): 2648-59; Epub 2007 Jul. 5). It is thus suggested that bone marrow mesenchymal stem cells are involved in the therapeutic effect described in this Example. Furthermore, bone marrow-derived cells such as bone marrow mesenchymal stem cells are known to differentiate into nerve cells, adipocytes, osteocytes, chondrocytes, and epithelial cells. Cells collected by using the devices of the present invention are applicable to novel regeneration-inducing medicine where damaged tissues are treated by supplying the tissues with the cells.

Reference Example 1

Objective: Identification of the HMGB1 family in the skin extract and examination of bone marrow mesenchymal stem cell-inducing activity Methods: Whether or not the neonatal mouse skin extract contained the HMGB protein family was confirmed using the Western blot method. Free skin pieces from 400 neonatal mice were immersed in 400 ml of physiological phosphate buffer solution (PBS; pH 7.4) and the solution was incubated at 4° C. for 24 hours. To remove the tissues, the samples were centrifuged at 440 G at 4° C. for 10 minutes and the supernatant was collected as skin extract. Ten µl of the skin extract obtained was used as a sample and subjected to SDS-PAGE electrophoresis. The proteins separated within the gel were transferred onto a PVDF membrane using a blotting device (ATTO). The membrane was incubated with PBS containing 3% skim milk and 0.1% Tween20 (S-T-PBS) at room temperature for one hour, and then was allowed to react with each of rabbit anti-mouse HMGB1 antibody, rabbit anti-mouse HMGB2 antibody, or rabbit anti-mouse HMGB3 antibody which were diluted 1,000-fold with S-T-PBS, at 4° C. for 16 hours. After the reaction, the PVDF membrane was washed with S-T-PBS five times for 5 minutes. Then, the PVDF membrane was incubated with 2,000-fold diluted (diluted with S-T-PBS) peroxidase-labeled goat anti-rabbit IgG antibody (GE Healthcare) at 25° C. for 1 hour. Further, after washing with S-T-PBS five times for 5 minute, the PVDF membrane was allowed to react with ECL Western Blotting Detection System (GE Healthcare). The ECL film was exposed and developed to detect the presence of HMGB1, HMGB2, and HMGB3 proteins.

RNA was extracted from the skin of neonatal mouse using Trizol (Invitrogen), and further cDNA was synthesized using the SuperScript III cDNA Synthesis Kit (Invitrogen). Using this cDNA as a template, cDNAs of HMGB1, HMGB2, and HMGB3 were amplified using the polymerase chain reaction (PCR) method. The cDNAs were inserted into the plasmid vector pCAGGS for expressing proteins in mammalian cells, such that proteins with an additional Flag-tag sequence (Asp-Tyr-Lys-Asp-Asp-Asp-Lys; SEQ ID: 30) at the N-terminus of the amino acid sequence could be expressed. These plasmid vectors were transfected into HEK293 (Human embryonic kidney derived culture cell line) and cultured for 48 hours to express the proteins. Cells expressing each of the HMGB1, HMGB2, and HMGB3 proteins and the culture supernatant were incubated at 4° C. for 16 hours, which was then centrifuged at 4,400 g for 5 minutes to collect the supernatant. 100 µL of the anti-Flag antibody Gel (Sigma) was mixed into 50 mL of this supernatant, and was then incubated at 4° C. for 16 hours. Centrifugation was then performed to collect the gel, and washed with PBS five times. Further, the protein was eluted using 3× Flag peptide (final 100 µg/ml). Expressions of recombinant proteins were observed by the Western blot method using 1,000-fold diluted (diluted with S-T-PBS) mouse anti-Flag antibody and 2,000-fold diluted (diluted with S-T-PBS) peroxidase-labeled anti-mouse IgG antibody (GE Healthcare). The mouse bone marrow mesenchymal stem cell migration activity in these purified recombinant proteins was assessed using a Boyden chamber. Moreover, in order to observe the in vivo drug efficacy of the HMGB family, the dorsal skin of 8-week-old C57BL/6 mice was cut out in a circle having a diameter of 8 μm to prepare cutaneous ulcer models. Purified HMGB1, HMGB2, and HMGB3 (100 ng/μl) were each mixed with the same amount of hyaluronic acid solution having a concentration of 1 g/100 mL of PBS, and 100 μL of it was administered to the ulcer surface. The ulcer surface was covered with a transparent adhesive wound dressing/protective material Tegaderm (3M Healthcare) to avoid drying, and the wound area was measured over time to determine the therapeutic effect.

Further, to examine whether or not the human skin extract and the purified human HMGB1 has an activity to allow migration of human bone marrow mesenchymal stem cells, a Boyden chamber was used for assessment. A human skin having an area of 1 cm$^2$ was immersed in 1 ml PBS, and then was incubated at 4° C. for 16 hours and subsequently centrifuged at 440 G at 4° C. for 10 minutes. The supernatant alone was collected to be used as a human skin extract. Moreover, human bone marrow mesenchymal stem cells (Cambrex) were used as the cells to be placed in the upper chamber of the Boyden chamber (as a result of surface antigen analysis by flow cytometry, these cells have been confirmed to be CD105-positive, CD166-positive, CD29-positive, CD44-positive, CD34-negative, and CD45-negative. They have also been found to differentiate into adipocytes, chondrocytes, and osteocytes by differentiation induction tests). Moreover, 100 ng/well of human HMGB1 (R&D) and human skin extract diluted 10-fold with PBS were placed in the lower chamber. PBS was used as a control.

Figure 8:
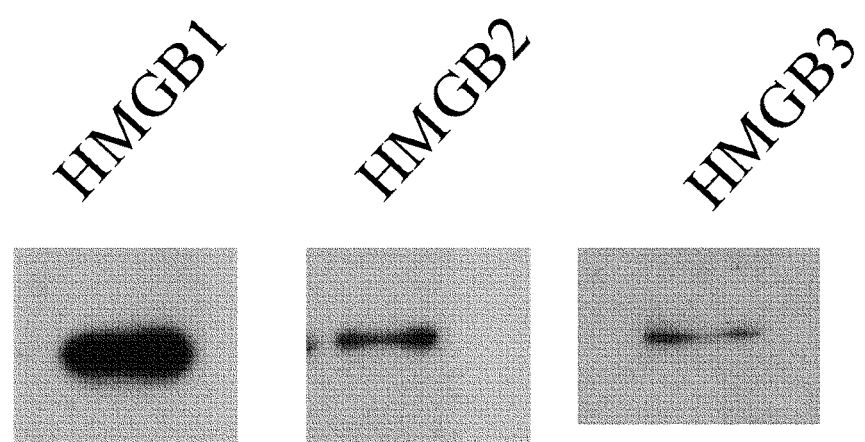
FIG. 8 shows in a set of photographs Western blot detection of the HMGB family in neonatal mouse skin extract.
Figure 9:
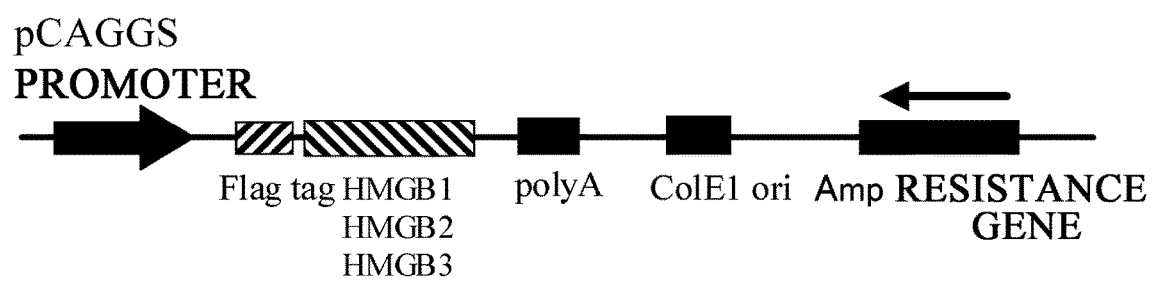
FIG. 9 shows in a diagram an HMGB1 expression vector.
Figure 10:
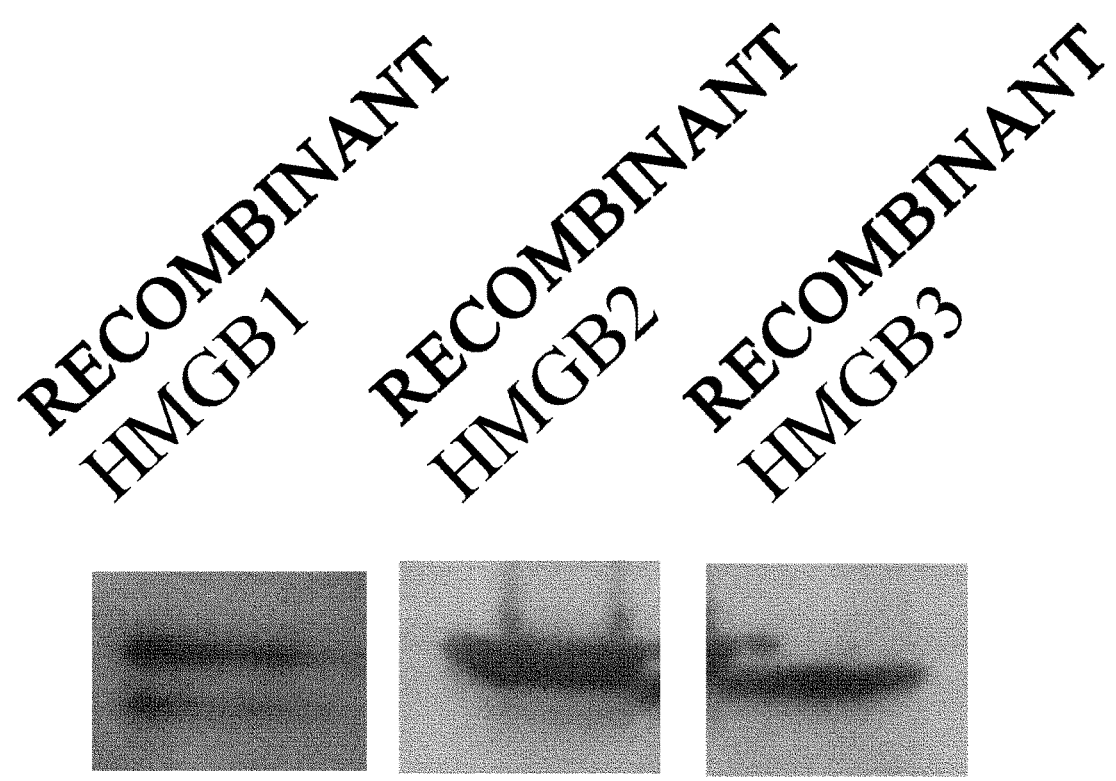
FIG. 10 shows in a set of photographs Western blot results for the purified recombinant Flag tag-HMGB family-fusion proteins expressed in HEK293 cells.
Figure 11:
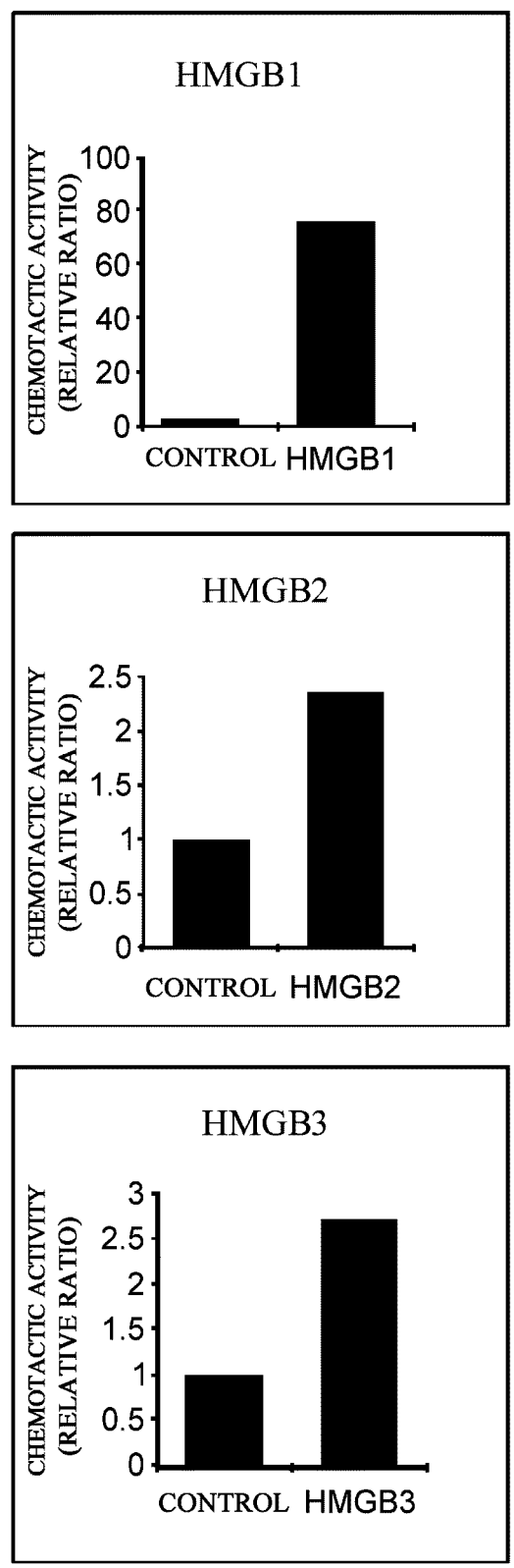
FIG. 11 shows in a set of graphs the chemotactic activity of recombinant HMGB1/HMGB2/HMGB3 for bone marrow mesenchymal stem cells using a Boyden chamber. All recombinant proteins showed higher chemotactic activities as compared to the control groups.
Figure 12:
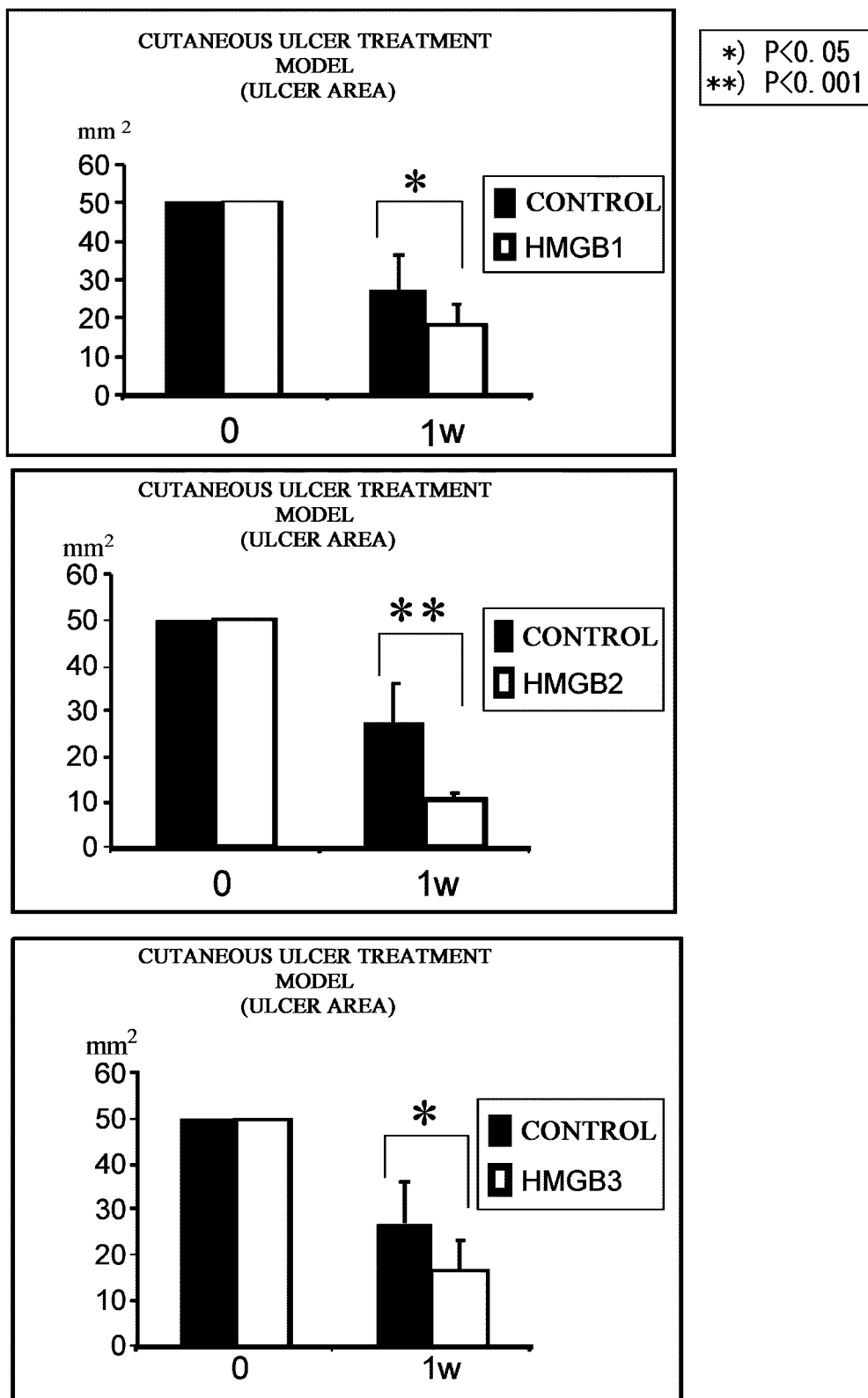
FIG. 12 shows in a set of graphs the result of treatment in a mouse cutaneous ulcer treatment model using the HMGB family proteins. HMGB1, HMGB2, and HMGB3 all showed significant effects on reducing the ulcer area as compared to the control groups.
Figure 13:
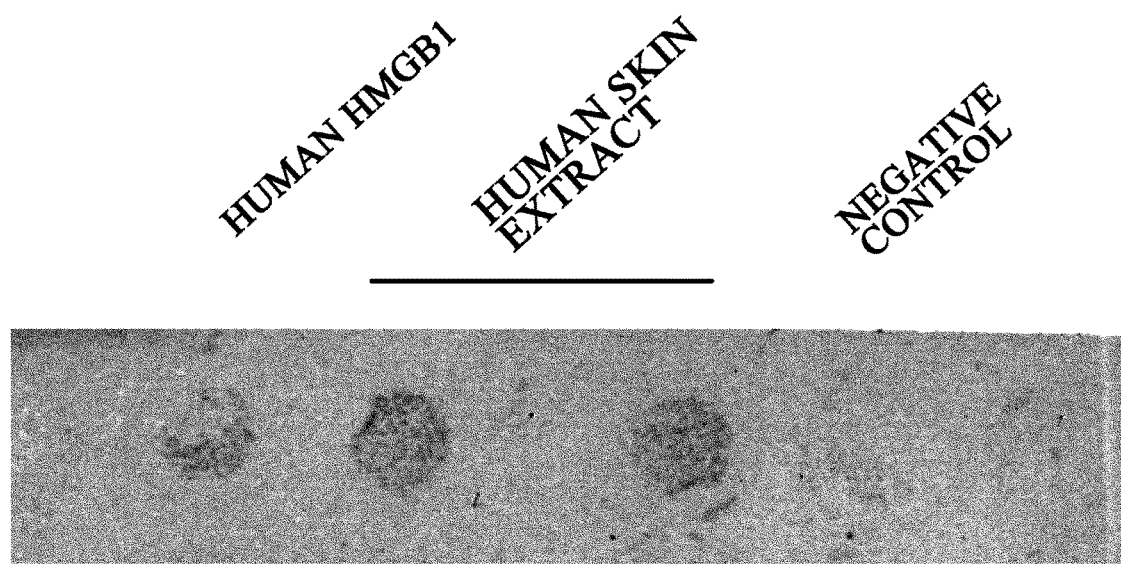
FIG. 13 shows in a photograph the activity of human HMGB1 and a human skin extract to induce the migration of human bone marrow-derived mesenchymal stem cells as confirmed using a Boyden chamber.

Results: As a result of Western blotting, bands of HMGB2 and HMGB3 were detected as well as the HMGB1 band. Therefore, the neonatal mouse skin extract was confirmed to contain the family proteins, HMGB2 and HMGB3, besides HMGB1 (FIG. 8). Expression vectors of HMGB1/HMGB2/HMGB3 having a Flag-tag added at the N-terminus of each protein were prepared (FIG. 9). These expression vectors were transfected into HEK293 cells, and the expressed proteins were purified using the Flag-tag, and Western blotting was carried out to observe these proteins (FIG. 10). The mouse bone marrow mesenchymal stem cell migration activity was measured using these purified proteins, and the activity was confirmed in all of the proteins (FIG. 11). The ulcer area produced in the back of the mouse was measured every 7 days, and a significant effect on reducing ulcer area was confirmed in the HMGB1, 2, and 3 treatment groups, as compared to the untreated group (FIG. 12). Similar to the mouse case, human HMGB1 and the human skin extract were revealed to have the activity of inducing the migration of human bone marrow mesenchymal stem cell (FIG. 13).

Discussion: HMGB2 and HMGB3 are known as proteins having high homologies to HMGB1. These proteins are also expected to have properties similar to HMGB1. It was confirmed that HMGB2 and HMGB3 of the HMGB1 family are also produced from the extract of the free skin section. Further, HMGB1/HMGB2/HMGB3 recombinant proteins were produced, and their in vitro bone marrow mesenchymal stem cell migration activity and the in vivo therapeutic effect on a cutaneous ulcer were also confirmed. It was revealed that the HMGB family (HMGB1/HMGB2/HMGB3) and the recombinant HMGB family in the neonatal mouse free skin section have a bone marrow mesenchymal stem cell-inducing activity and an activity of locally inducing bone marrow-derived stem cells which are differentiatable into epithelium, and that the thus induced bone marrow-derived cell group differentiates into various cells such as epidermal keratinocytes, hair follicles, and fibroblasts in the damaged tissue to promote the recovery of the damaged tissue. Moreover, since bone marrow mesenchymal stem cells are multipotent stem cells, the present inventors believe that therapeutic effects can also be expected in the same manner by systematic administration or local administration of the HMGB family to treat damaged states in other tissues, for example, tissue damages such as brain injury, myocardial infarction, and bone fracture.

Moreover, it is known that, between human and mouse, amino acid sequence homology for HMGB1 is 98% (213/215), 96% (202/210) for HMGB2, and 97% (195/200) for HMGB3. Therefore, human HMGB and mouse HMGB are considered to have similar activities, and the results revealed that human skin extract and human HMGB1 have bone marrow mesenchymal stem cell-inducing activities in a manner same as those of mouse skin extract and mouse HMGB1.

Reference Example 2

Objective: Establishment of a method of producing a tissue extract containing bone marrow mesenchymal stem cell-inducing factors Methods: Brain, heart, intestine, kidney, and liver of a 6-week-old C57BL6 mouse and skin of a neonatal mouse were immersed in 1 ml of physiological phosphate buffer solution (PBS) at pH 7.4. The solutions were incubated at 4° C. for 24 hours, and then centrifuged at 440 G at 4° C. for 10 minutes to remove the tissues. The supernatants were collected to prepare tissue extracts. To confirm whether the thus obtained extract has a bone marrow-derived mesenchymal stem cell-inducing activity, the migration activity of bone marrow-derived mesenchymal stem cells was examined using a Boyden chamber. Moreover, the HMGB1 concentration contained in these samples was measured using an HMGB1 ELISA Kit (Shino-Test). Further, tissue extracts of the brain, heart, and skin were allowed to bind to a heparin affinity column, and the bone marrow-derived mesenchymal stem cell-inducing activity in the protein-bound fraction was confirmed using Boyden chamber.

Figure 14:
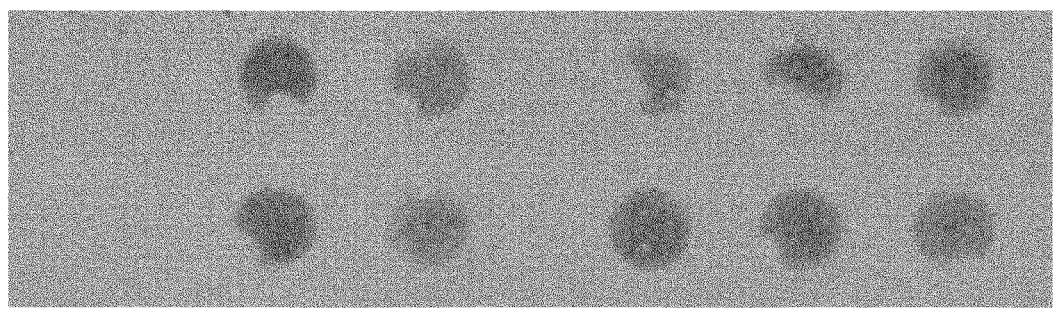
FIG. 14 shows in a set of photographs the activity of activators purified on a heparin column from mouse heart, brain, and skin extracts to induce bone marrow mesenchymal stem cells as confirmed using a Boyden chamber.
Figure 14:
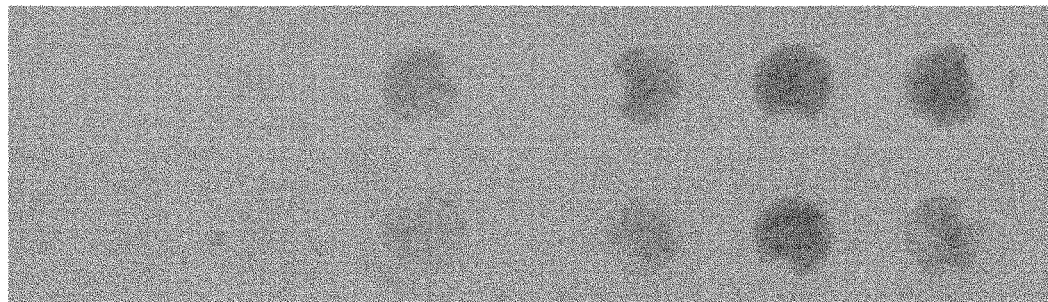

Results: The mouse brain extract contained an amount of HMGB1 equivalent to the neonatal mouse skin extract. Further, bone marrow mesenchymal stem cell-inducing activity was also observed in the mouse brain as well as in the skin. Although the mouse intestine extract and the mouse heart extract contained little HMGB1, bone marrow mesenchymal stem cell-inducing activities were observed. Moreover, the heparin column-bound fractions of mouse brain and mouse heart, as well as the heparin column-bound fraction of mouse skin, showed bone marrow mesenchymal stem cell-inducing activities (FIG. 14). Table 1 shows the measurement results of the HMGB1 concentration and the bone marrow mesenchymal stem cell-inducing activity in each of the mouse tissue extracts.

TABLE 1

|  | HMGB1 concentration (ng/mL) | Bone marrow mesenchymal stem cell inducing activity |
|---|---|---|
| Skin | 110 | Present |
| Brain | 140 | Present |

TABLE 1-continued

| | HMGB1 concentration (ng/mL) | Bone marrow mesenchymal stem cell inducing activity |
|---|---|---|
| Heart | 4 | Present |
| Intestine | 0 | Present |
| Kidney | 115 | ND |
| Liver | 61 | ND |

ND: Not Determined

Discussion: A method in which HMGB1 can be conveniently extracted not only from the skin but also from the brain was developed by simply immersing these organs in a physiological buffer. This method is also applicable to other organs such as liver and kidney. Moreover, although the extracts from intestine and heart contain little HMGB1, a bone marrow mesenchymal stem cell-inducing activity was observed. This suggests these extracts contain other bone marrow mesenchymal stem cell-inducing substance(s) apart from HMGB1. Such substances contained in these extracts are originally present in each tissue, and are considered to physiologically induce bone marrow mesenchymal stem cells to the damaged tissue when the tissue is damaged. The present invention developed a novel method for conveniently and functionally extracting from various organs multiple bone marrow mesenchymal stem cell-inducing substances including HMGB1. Further, a method for purifying bone marrow mesenchymal stem cell-inducing substances from a tissue extract using the binding to the heparin column was also developed. These substances having bone marrow mesenchymal stem cell-inducing activities can be purified from the brain and heart in the same manner as in the skin using a heparin column.

Reference Example 3

Objective: Establishment of a method for extracting mesenchymal stem cell migration activators from cultured cells.

Methods: Human embryonic kidney derived cultured cell line HEK293 and human cervix carcinoma cell line HeLa were each cultured in 10% fetal bovine serum-containing D-MEM (Nacalai). These cells were each washed with PBS, and then $10^7$ cells were immersed in 5 ml of PBS (Nacalai) at 4° C. for 16 hours. The solution was centrifuged at 440 G (acceleration of gravity) at 4° C. for 5 minutes, and then the supernatant was collected. Human bone marrow mesenchymal stem cells were placed in the upper chamber of a Boyden chamber, and a 5-fold diluted (with DMEM) cell extract was placed in the lower chamber, to confirm the migration activity of human bone marrow mesenchymal stem cells.

Figure 15:
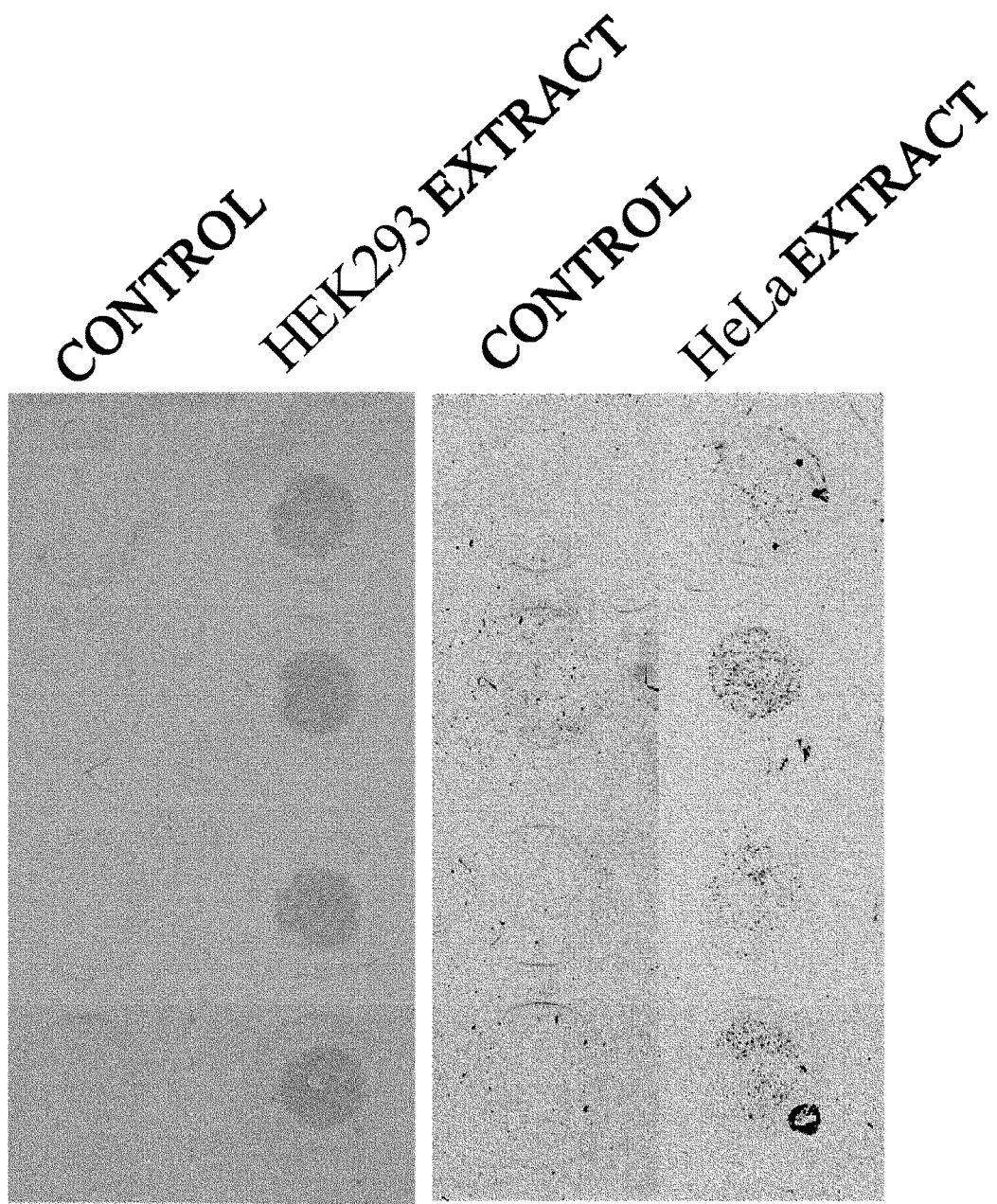
FIG. 15 shows in a set of photographs the activity of an extract of the cultured cell line HEK293 or HeLa to induce migration of human bone marrow mesenchymal stem cells as confirmed using a Boyden chamber. Both cultured cell lines showed chemotactic activity for human bone marrow mesenchymal stem cells.

Results: HEK293 extract and HeLa extract both showed similar bone marrow mesenchymal stem cell migration activities (FIG. 15).

Discussion: Bone marrow mesenchymal stem cell migration activators were successfully extracted by the convenient method of immersing cultured cells in PBS.

Reference Example 4

Objective: Whether or not regeneration of neural cells can be induced is examined by producing mouse brain-defective models, to which a heparin-column purified fraction of skin extract is administered in a sustained-release manner at the local lesion site, by which stem cells contained in a mouse myeloid system is allowed to migrate into the local lesion site.

Methods:

(1) Preparation of Heparin-Column Purified Fraction of Skin Extract

An excised skin section of a neonatal mouse was incubated in PBS (mouse/ml) at 4° C. for 16 hours, and a skin extract was obtained. The skin extract was diluted 10-fold with 9 volumes of 20 mM phosphate buffer at pH 7.5 at 4° C. 20 mM phosphate buffer at pH 7.5 (30 ml) was poured into HiTrap Hepalin HP column (column volume: 5 ml, GE Healthcare) in advance to equilibrate the column. The diluted solution was then allowed to bind to the column. Thereafter, the column was washed with 20 mM phosphate buffer at pH 7.5 and 100 mM NaCl (30 ml). To elute the adsorbed proteins, 20 mM phosphate buffer at pH 7.5 and 1,000 mM NaCl were poured into the column, and the factions were eluted into the tubes. Each of the adsorbed factions were evaluated according to the mouse bone marrow-derived cell migration activity assessment using the Boyden chamber method, and fraction(s) having migratory activity was collected. Solution(s) having the activity was used as a heparin purified fraction(s) of the skin extract in the following Reference Example.

(2) Production of Myelosuppressive Mice

Mice were irradiated with single-dose of X-ray at 10 Gy to produce myelosuppressive mice.

(3) Transplantation of GFP Mouse Bone Marrow to Myelosuppressive Mice

Bone marrow cells were collected from both femurs and crus bones of GFP mice. These cells were administered to the myelosuppressive mice through the caudal vein 24 hours after the irradiation. The administration was carried out under inhalational anesthesia using isoflurane.

(4) Production of a Brain-Defective (Brain Tissue-Defective) Mouse Model

Figure 16:
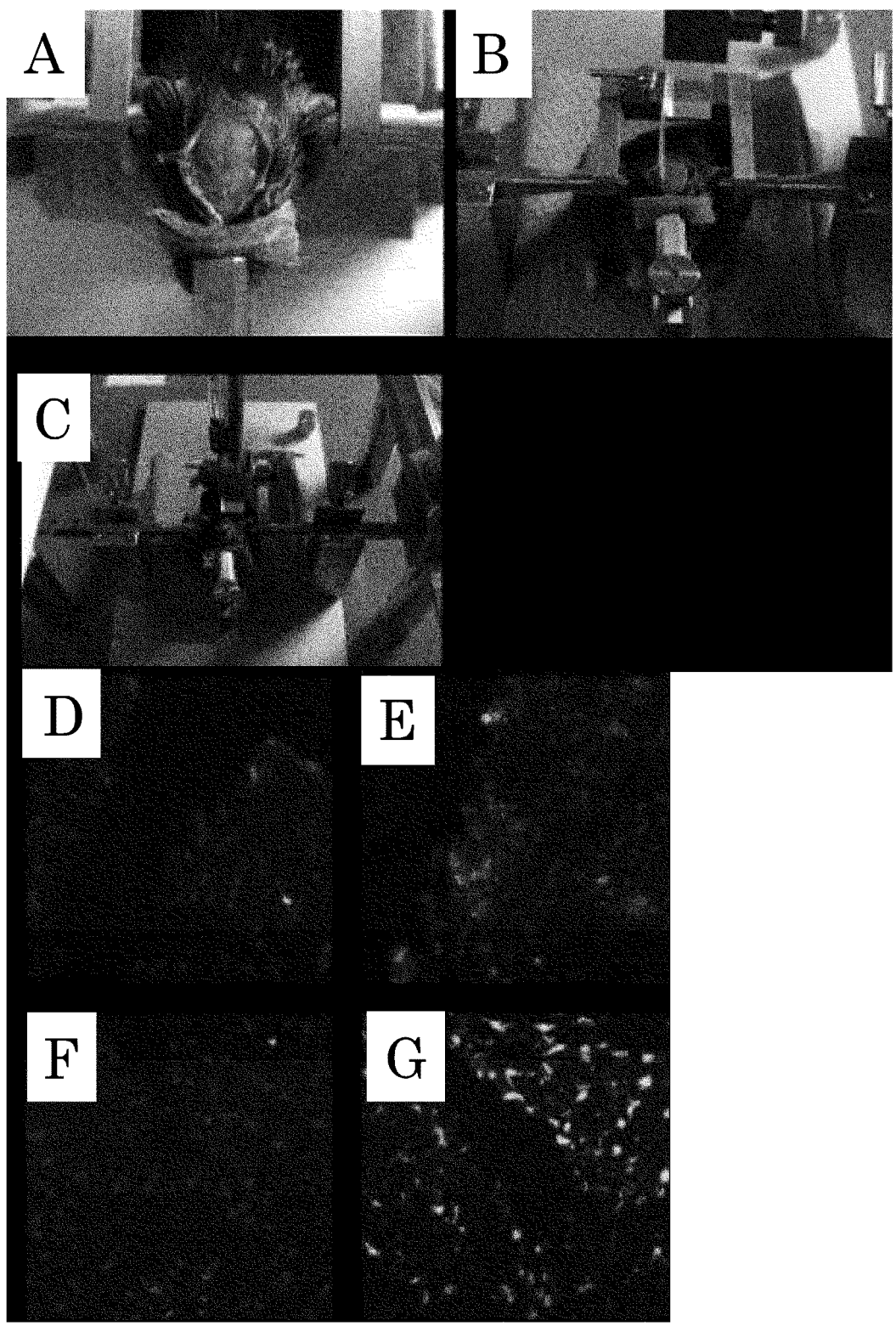

The myelosuppressive mice transplanted with GFP mouse bone marrow cells were subjected to inhalational anesthesia using isoflurane, and pentobarbital (45 mg/kg) was intraperitoneally injected to the mice. The mice were fixed onto a brain stereotaxis apparatus and subjected to a midline incision in the head with a scalpel. Trepanation was carried out at 2.5 mm right-lateral and 12.5 mm anterior to the bregma using a drill (FIG. 16A). At a 3 mm depth from this site, a 20 G Surflow needle was inserted and fixed. Then, a negative pressure was applied using a syringe to suck part of the brain tissue (FIG. 16B).

(5) Administration of a Heparin-Column Purified Fraction of Skin Extract to the Brain Tissue-Defective Site Five microliters of a heparin-column purified fraction of skin extract dissolved in a fibrin tissue adhesive formulation (fibrinogen) (Bolheal (Kaketsuken)) was injected to the above site, and subsequently, 5 µl of a fibrin tissue adhesive formulation (thrombin) (Bolheal (Kaketsuken)) was injected using a Hamilton syringe and a 26 G syringe (FIG. 16C). The aim of this operation was to exert the sustained-release agent effect of a heparin-column-purified fraction of the skin extract.

(6) Assessment of the Effects of Neural Cell Regeneration in Brain Tissue-Defective Sites Mice of the control group and the treatment group were used for the assessment. An appropriate elapsed time setting (over time) was determined, the mice were perfused with 4% paraformaldehyde and fixed and then the brain was cut out. Further, external fixation was performed with 4% paraformaldehyde. These were then dehydrated in a 15% and 30% sucrose gradient to produce frozen sections.

The nucleus were stained with a DAPI (4',6-Diamidino-2-phenylindole, dihydrochloride) solution and the section was sealed using a photobleaching inhibitor. The accumulation of GFP-positive cells in the lesion site (brain tissue-defective site) was assessed using a confocal laser microscope.

Results: The accumulation of GFP-positive cells is qualitatively shown for 2 weeks, and 6 weeks after the administration. The accumulation of GFP-positive cells tends to be higher in the lesion sites of the treatment group rather than the control group, for both 2 weeks (control; FIG. 16D, skin extract heparin-column-purified fraction; FIG. 16E) and 6 weeks (control; FIG. 16F, skin extract heparin-column-purified fraction; FIG. 16G) after the administration.

Discussion: The administration of the heparin-column-purified fraction of the skin extract resulted in the accumulation of bone marrow-derived cells in the brain tissue-defective site, which showed a nerve cell form. Bone marrow-derived mesenchymal stem cells are also known to differentiate into nerve cells and the result revealed that the heparin-column purified fraction of the skin extract is capable of inducing neural cell regeneration of the injured site in the brain. Moreover, this is also applicable to neuronal regeneration of damaged sites in brain tissues in cerebral ischemic diseases and cerebral contusions.

Reference Example 5

Purpose: To identify bone marrow-derived tissue stem cell-inducing factors in skin tissue extracts Methods: By the method described below, study was conducted to identify factors responsible for mobilizing bone marrow mesenchymal stem cells, which were predicted to be released from excised skin under hemostatic condition.

(1) Bone marrow cells were harvested from the thighbones or crural bones of C57BL/6 mice to obtain mouse bone marrow-derived mesenchymal stem cells. The cells were seeded into a cell culture dish with D-MEM (Nacalai) supplemented with 10% fetal bovine serum as a culture medium and cultured at 37° C. under 5% carbon dioxide gas. When the cells were grown to occupy an area of 70 to 100% relative to the bottom of the culture dish, the cells were detached from the culture dish using 0.25% trypsin/1 mM EDTA (Nacalai). The cells were then passaged under the same culture conditions. After at least five passages, the adherent cells were isolated and further cultured, and analyzed for cell surface antigens by flow cytometry. The result showed that the cells were positive for CD44 and Sca-1, and negative for Lin, CD45, and c-kit. It was confirmed that the cells can differentiate into osteocytes and adipocytes and thus have the characteristics of bone marrow mesenchymal stem cells.

(2) Free skin pieces isolated from five heads of neonatal mice (two-day-old) were immersed in 5 ml of physiological phosphate buffered saline (PBS, pH 7.4). After 24 hours of incubation at 4° C., the sample was centrifuged at 440 G at 4° C. for ten minutes to remove tissues. The supernatant was collected as skin extract. In addition, in the same way, free skin pieces isolated from a six-week-old mouse were immersed in 5 ml of physiological phosphate buffered saline (PBS, pH 7.4). After incubation at 4° C. for 24 hours, the samples were centrifuged at 440 G at 4° C. for ten minutes to remove tissues. The supernatants were collected as skin extract.

(3) To confirm whether the prepared skin extract has the activity of inducing bone marrow mesenchymal stem cells, the present inventors used the Boyden chamber to examine the chemotactic activity for previously cloned bone marrow-derived mesenchymal cells derived from C57BL6 mice. Specifically, a mixture of DMEM (20 µl) and skin extract (5 µl) from two-day-old or six-week-old mice was added into the bottom compartment (a volume of 25 µl) of a Boyden chamber, and a polycarbonate membrane with 8-µm micropores was placed on top. Then, the upper compartment (a volume of 50 µl) of the Boyden chamber was placed in contact with the membrane, and a suspension of bone marrow-derived mesenchymal stem cells ($5 \times 10^4$ cells/50 ml of culture medium (DMEM supplemented with 10% fetal bovine serum)) was added to the upper compartment. The chamber was incubated in a $CO_2$ incubator at 37° C. for four to 24 hours. After incubation, the upper unit of the chamber was removed. The thin silicone film was detached and the number of bone marrow-derived mesenchymal stem cells migrating into the bottom compartment through the micropores was quantitatively determined by staining the cells (FIG. 17).

(4) About 2-$cm^2$ skin specimens were excised from two-day-old and six-week-old mice and immediately frozen in liquid nitrogen. The skin specimens were crushed in a mortar. RNAs were extracted and purified from the samples using RNeasy (Qiagen). Using the purified RNAs, microarray assay was carried out to screen for mRNA expressed at higher levels in the two-day-old mice. 767 genes showed two or more times greater scores in the two-day-old mice. Of these genes, proteins with high affinity for heparin, potential secretory proteins, and genes whose scores were six or more times greater in the two-day-old mice were examined and S100A9 was found as the $57^{th}$ gene from the top. Thus, S100A8 which is known to form a heterodimer with S100A9 in the skin extract from the two-day-old mice was detected by Western blotting. Specifically, 5 µl of the skin extract from the two-day-old mice was combined with 5 µl of SDS-PAGE sample buffer (Bio-Rad). The mixture was heated in a heat block at 98° C. for five minutes, and then cooled to 25° C. The resulting sample was applied onto 12.5% acrylamide gel e-PAGEL (ATTO) and electrophoresed at 40 mA for 75 minutes using an electrophoretic device (ATTO). The gel was collected after electrophoresis. Using a blotting device (ATTO), proteins in the gel were transferred to PVDF membrane (7 cm by 9 cm, Millipore) pretreated with 100% methanol. After 75 minutes of protein transfer at 120 mA, the PVDF membrane was removed and shaken at room temperature for 30 minutes in PBS (Nacalai) containing 4% skim milk. Then, the removed PVDF membrane was soaked in 5 µl of anti-S100A8 antibody (R&D) or anti-S100A9 antibody (R&D) each diluted with 10 ml of PBS containing 4% skim milk, and shaken at room temperature for 60 minutes. After the antibody solution was removed, the membrane was shaken in 30 ml of PBS containing 0.1% Tween20 at room temperature for five minutes. This washing was repeated five times. Then, the membrane was soaked in 5 µl of HRP-labeled anti-goat IgG antibody (GE healthcare) diluted with 10 ml of PBS containing 4% skim milk, and shaken at room temperature for 45 minutes. After the antibody solution was removed, the membrane was washed with 30 ml of PBS containing 0.1% Tween20 at room temperature for five minutes while shaking. This washing was repeated five times. The membrane was treated for luminescence using ECL Detection Kit (GE healthcare), and then exposed on a film. Signals for S100A8 and S100A9 proteins were gained by developing the film in a developing apparatus (FIG. 18).

(5) Factors having the activity of mobilizing bone marrow-derived mesenchymal stem cells in skin extracts were purified by heparin affinity column chromatography. The experiment described below was carried out using an FPLC device (GE healthcare). First, the skin extract of two-day-old mice was diluted 10-fold with nine volumes of 20 mM phosphate buffer (pH 7.5) at 4° C. (dilution solution A). 300 ml of 20 mM phosphate buffer (pH 7.5) was run through a HiPrep 16/10 Heparin FF (GE Healthcare) column to equilibrate the column in advance, and dilution solution A was loaded onto the column. Then, the column was washed with 300 ml of 20 mM phosphate buffer (pH 7.5). 20 mM phosphate buffer (pH 7.5) containing 10 mM NaCl (solution A) and 20 mM phosphate buffer (pH 7.5) containing 500 mM NaCl (solution B) were prepared to elute the adsorbed protein. Elution was started with [100% solution A+0% solution B], and then the proportion of solution B was gradually increased. Finally, the column was eluted with [0% solution A+100% solution B]. The total elution volume was 150 ml. The eluate was fractionated into silicone-coated tubes (3 ml/tube). 5 µl each of the fractionated samples were mixed with 5 µl of SDS-PAGE sample buffer (Bio-Rad). The mixtures were heated in a heat block at 98° C. for five minutes, and then cooled to 25° C. The samples were applied onto an acrylamide gel e-PAGEL (5-20% gradient, ATTO), and electrophoresed at 40 mA for 75 minutes using an electrophoresis device. After the electrophoresis, the electrophoresed protein was detected using the Dodeca Silver Stain Kit (Bio-Rad) (FIG. 19).

The chemotactic activity of fractionated samples was assayed in the same way as described above using a Boyden chamber (FIG. 20).

The presence of S100A8 and S100A9 proteins in the fractionated samples was detected in the same way as described above by Western blotting (FIG. 21).

(6) RNA was extracted from neonatal mouse skin using Trizol (Invitrogen), and then cDNA was synthesized from the RNA using the SuperScript III cDNA Synthesis Kit (Invitrogen). cDNAs of S100A8 and S100A9 were amplified by the polymerase chain reaction (PCR) method using the cDNA as a template. These cDNAs were each inserted into a mammalian cell protein-expression plasmid vector, pCAGGS, to express the proteins in which a GST-tag sequence (amino acid sequence/SEQ ID NO: 31; DNA sequence/SEQ ID NO: 32) is attached to the N-terminus of their amino acid sequences (FIG. 22). pCAGGS-GST-S100A8 or pCAGGS-GST-S100A9 were each transfected into a human fetal kidney cell-derived cultured cell line HEK293 using a lipofection reagent (Invitrogen). 48 hours after transfection, the cells and culture supernatant were collected, and centrifuged at 4,400 G at 4° C. for five minutes. The supernatant (Supernatant A) and cells were collected separately. PBS containing 0.1% Tween20 was added to the cells, and the suspension was sonicated on ice for 30 seconds to disrupt the cell membrane. After centrifugation at 4,400×g at 4° C. for five minutes, the resulting supernatant was collected (Supernatant B). Supernatants A and B were combined together and loaded onto a HiTrap GST FF column (5 ml; GE Healthcare) whose buffer had been replaced with 30 ml of PBS in advance. After loading, the column was washed with 100 ml of PBS, and the adsorbed protein was eluted with 20 mM phosphate buffer (pH 8) containing reduced glutathione. The chemotactic activity of recombinant S100A8 and S100A9 for bone marrow mesenchymal stem cells was assessed using the Boyden chamber. The samples were prepared by dissolving purified S100A8 or S100A9 protein at 0.1 ng/µl in DMEM, or by diluting the skin extract of two-day-old mice with four volumes of DMEM, and added into the bottom compartment of the Boyden chamber. A negative control prepared as follows was used the same way: protein was extracted from cells transfected with a control vector which does not carry the cDNA of S100A8 or S100A9 as an insert; and then a fraction was eluted from a HiTrap GST FF column. After a sample was added into the bottom compartment, a polycarbonate membrane with 8-µm micropores was placed on top. Then, the upper unit (a volume of 50 µl) of Boyden chamber was placed in contact with the membrane, and a suspension of bone marrow-derived mesenchymal stem cells ($5 \times 10^4$ cells/50 ml of culture medium (DMEM supplemented with 10% fetal bovine serum)) was added to the upper chamber. The chamber was incubated in a $CO_2$ incubator at 37° C. for four to 24 hours. After incubation, the upper unit of the chamber was removed. The thin silicone film was detached and the number of bone marrow-derived mesenchymal stem cells migrating into the bottom compartment through the micropores was quantitatively determined by staining the cells (FIG. 23).

(7) Eight-week-old male mice were injected with 250 µl of the above-described purified GST-S100A8 or S100A9 recombinant proteins (1 ng/µl) via the caudal vein. 12 hours after injection 1 ml of peripheral blood was collected from the hearts of the mice under inhalation anesthesia with isoflurane using a 1-ml heparin-coated syringe. The blood samples were each combined with 3 ml of PBS, and then gently overlaid onto 3 ml of Ficoll (GE healthcare). The resulting samples were centrifuged using centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells, and the cells were incubated at room temperature for five minutes. This hemolytic treatment was repeated twice. After adding 10 ml of PBS, the cells were centrifuged at 440×g at 25° C. for five minutes. The resulting supernatants were removed, and the cells were collected. 1,000,000 cells were incubated at room temperature for 20 minutes with a PE-labeled anti-mouse PDGFRα antibody (e-Bioscience), PE-labeled anti-mouse PDGFRβ antibody (e-Bioscience), FITC-labeled anti-mouse CD45 antibody (BD biosciences), and PerCy5-labeled anti-mouse CD44 antibody (BD biosciences), each diluted 100-fold with PBS. Then, the cells were centrifuged at 440×g at 25° C. for five minutes. The supernatants were removed. 400 µl of PBS containing 1% paraformaldehyde was added to the cells to prepare samples for flow cytometric analysis. Antibodies were used in the following combinations:

(I) PDGFRα/CD45/CD44
(II) PDGFβ/CD45/CD44

The ratio of cells expressing PDGFRα (or β) and CD44 to cells that were weakly positive or negative for CD45 was determined based on the analysis result (FIGS. 24A and B).

Figure 24:
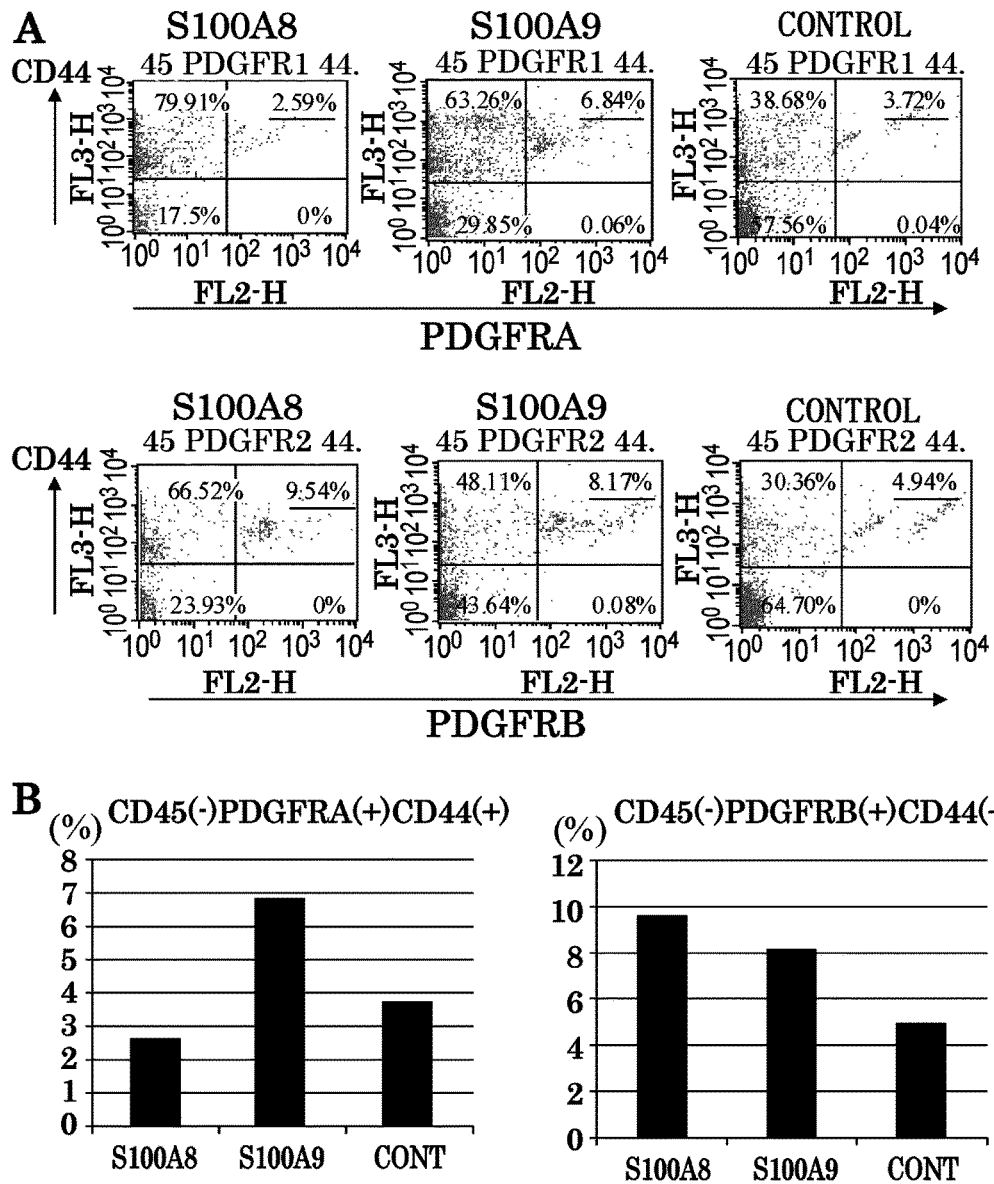

Results: Skin samples excised from two-day-old and six-week-old mice were assessed for the activity of mobilizing bone marrow mesenchymal stem cells. The activity of skin extract from two-day-old mice was demonstrated to be stronger than that of the skin extract from six-week-old mouse. Strong S100A9 expression in the skin from two-day-old mice was found by DNA microarray analysis. Crude samples of skin extracts purified on a heparin column exhibited correlation between the migrating activity of mesenchymal stem cells and the contents of S100A9 and S100A8. Expression vectors for these proteins were constructed, and the recombinant proteins were produced using HEK293 and purified. The migrating activity of bone marrow mesenchymal stem cells was confirmed in the purified S100A8 and S100A9 samples by assays using Boyden chamber. Furthermore, when intravenously administered to mice, the proteins also exhibited the activity of mobilizing a population of PDGFRα and CD44 double-positive cells to peripheral blood (FIG. 24).

Discussion: The present inventors for the first time in the world discovered in the present invention that free skin pieces produce S100A8 and S100A9, and the produced S100A8 and S100A9 proteins had strong activities of mobilizing bone marrow-derived mesenchymal stem cells. Meanwhile, bone marrow mesenchymal stem cells are known as pluripotent stem cells that differentiate into bone tissues, adipose tissues, cartilage tissues, fibroblasts, and the like. Recently, it has been indicated that bone marrow-derived cells also include pluripotent stem cells that differentiate into tissues such as cardiac muscle, nerve cells, and epidermal cells. Since the present invention demonstrates that the epidermal cells, hair follicle cells, fibroblasts of subcutaneous tissues, and such in the grafted skin are constituted by bone marrow-derived cells, S100A8 and S100A9 can be speculated to be responsible for mobilizing bone marrow-derived tissue stem cells to the skin graft to induce functional repair of damaged tissues. Even by intravenous injection, S100A8 and S100A9 can mobilize bone marrow mesenchymal stem cells to peripheral blood. Thus, S100A8 and S100A9 can also be administered via peripheral circulation to tissues located deep inside the body where local administration is difficult (brain, heart, spinal cord, etc.). The present inventors believe that effects such as shortening the healing time, functional regeneration of damaged tissues, and such can be expected in the healing process for not only damaged skin tissues but also various damaged tissues such as brain, muscle, and bone by using the present invention in pharmaceuticals, which enables local mobilization of the bone marrow-derived tissue stem cells including mesenchymal stem cells in regeneration of damaged tissues.

Reference Example 6

Purpose: To assess the therapeutic effect of S100A8 on cutaneous ulcer in normal and diabetic mice Methods: Recombinant S100A8 protein was administered to cutaneous ulcer model mice to assess its therapeutic effect on ulcer. Test mice used were: C57/Bl6 mice transplanted with bone marrow cells expressing GFP, and BKS.Cg-m+/+ Leprdb/J (db mice), which are diabetes model mice. Cutaneous ulcers with a diameter of 6 mm were formed on the skin of the mice. When cutaneous ulcer is formed in mice, the surrounding skin close to the skin defect rapidly shrinks. In this experiment, to create a therapeutic model for skin defect, in which skin defect is treated not through shrinkage but by covering it with regenerated skin, a silicone rubber disc with an outer diameter of 10 mm, inner diameter of 6 mm, and thickness of 0.5 mm was fixed at the skin defect site to the skin surrounding the ulcer using an adhesive agent for skin surgery (Aron alpha A) and nylon suture to prepare a model for treating skin defect by covering it with regenerated skin, not by shrinkage of the skin. Then, the recombinant S100A8 protein was directly administered to the ulcer surface at 1.5 μg/day every day for seven days. Furthermore, the ulcer surface was protected with film dressing Tegaderm (3M) to prevent desiccation of the ulcer surface. The ulcer surface area was measured over time to assess the therapeutic effect.

Results and discussion: In normal mice, the ulcer surface area was significantly reduced in the S100A8-treated group seven days after the start of treatment as compared to the control group (FIG. 25). Furthermore, in diabetes mice, the ulcer surface area was also significantly reduced in the S100A8-treated group seven days after the start of treatment as compared to the control group (FIG. 26). In other words, the significant cutaneous ulcer-reducing effect was observed in both normal and diabetes mice. From this result, it is confirmed that S100A8 has the therapeutic effect on cutaneous ulcer in not only normal mice but also diabetes mice.

Reference Example 7

Purpose: Mobilization of bone marrow tissue stem cells to peripheral blood using bone marrow-derived tissue stem cell-inducing factors in skin tissue extract Methods: To achieve the above purpose, a study was conducted by the method described below.

(1) Preparation of bone marrow-derived tissue stem cell-inducer. Free skin pieces isolated from 25 neonatal mice (two days old) were immersed in 25 ml of phosphate buffered saline (PBS), pH 7.4. After 24 hours of incubation at 4° C., the sample was centrifuged at 440 G at 4° C. for ten minutes to remove the tissue. The supernatant was collected as skin extract (SE).

Meanwhile, RNA was extracted from neonatal C57/Bl6 mice skin using Trizol (Invitrogen), and then cDNA was synthesized using the SuperScript III cDNA Synthesis Kit (Invitrogen). Polymerase chain reaction (PCR) was carried out using this cDNA as a template to amplify HMGB1 cDNA. The HMGB1 cDNA was inserted into an mammalian cell protein expression plasmid vector, pCAGGS, to express a protein in which a Flag-tag sequence (Asp-Tyr-Lys-Asp-Asp-Asp-Lys, SEQ ID NO: 30) is attached to the N-terminus of its amino acid sequence (FIG. 32). The plasmid vector was transfected into HEK293 (cultured cell line derived from human fetal kidney cell). The cells were cultured for 48 hours to express the protein. Each sample of cells expressing the HMGB1 protein and the culture supernatant were incubated at 4° C. for 16 hours, and then centrifuged at 4,400×g for five minutes. The supernatant was collected, and anti-Flag Antibody Gel (Sigma) was added thereto in an amount of 100 μl per 50 ml of the supernatant. The mixture was incubated at 4° C. for 16 hours. The gel was collected by centrifugation, followed by five PBS washes. Then, the gel was eluted with 3× Flag peptide (final 100 μg/ml). The concentration of the eluted protein was determined using the HMGB1 ELISA Kit (Shino-Test Co.). After freeze-drying, the protein concentration was adjusted to 200 μg/ml with PBS.

(2) Eight-week-old male mice (C57/Bl6) were administered with 500 μl of the above-described skin extract (SE), or 500 μl of PBS as a negative control group, via the caudal vein using syringes attached with a 30 G ½ injection needle (FIG. 33). Six, 12, 24, and 48 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged using a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience), PE-labeled anti-mouse PDGFRβ antibody (e-Bioscience), and PerCy5-labeled anti-mouse CD44 antibody (BD biosciences). After incubation, the cells were centrifuged at 440×g at 25° C. for five minutes. The supernatant was removed. 400 μl of PBS containing 1% paraformaldehyde was added to the cells to prepare a sample for flow cytometric analysis.

Eight-week-old male mice (C57/Bl6) were administered with 250 μl of mouse HMGB1 (1 μg/μl), or 250 μl of PBS as a negative control group, via the caudal vein using syringes attached with a 30 G ½ injection needle (FIG. 35). 12 hours after administration, 1 ml of peripheral blood was collected from the hearts of the mice under inhalation anesthesia with isoflurane using a heparin-coated 1-ml syringe. The blood samples were each combined with 3 ml of PBS, and then gently overlaid onto 3 ml of Ficoll (GE healthcare). The resulting samples were centrifuged in a centrifuge at 400×g at 25° C. for 40 minutes. The cells in the opaque middle layer were collected as a mononuclear cell fraction. 1 ml of HLB solution (Immuno-Biological Laboratories Co., Ltd.), a hemolytic agent, was added to the collected cells. The cells were incubated at room temperature for five minutes. This hemolytic treatment was repeated twice. After adding 10 ml of PBS, the cells were centrifuged at 440×g at 25° C. for five minutes. The supernatants were removed, and the cells were collected. 1,000,000 cells were incubated at room temperature for 20 minutes with antibodies each diluted 100-fold with PBS including a PE-labeled anti-mouse PDGFRα antibody (e-Bioscience) and PerCy5-labeled anti-mouse CD44 antibody (BD biosciences). After incubation, the cells were centrifuged at 440×g at 25° C. for five minutes. The supernatant was removed. 400 μl of PBS containing 1% paraformaldehyde was added to the cells to prepare a sample for flow cytometric analysis.

Results: PDGFRα and CD44 double-positive cells were demonstrated to be significantly mobilized to peripheral blood 12 hours after injection of the skin extract (SE) (FIG. 34). Furthermore, PDGFRα and CD44 double-positive cells were demonstrated to be significantly mobilized to peripheral blood 12 hours after injection of HMGB1 (FIG. 36).

Reference Example 8

Purpose: To test whether mesenchymal stem cells are mobilized to peripheral blood by intravenous administration of recombinant HMGB1 protein.

Methods: C57BL6 mice (eight to ten weeks old, male) were administered with 400 μl of physiological saline containing 100 μg/ml recombinant HMGB1 protein (40 μg of HMGB1) or 400 μl of physiological saline alone through the caudal vein. After 12 hours, peripheral blood was collected from the mice. The blood samples were diluted with PBS to a total volume of 4 ml. The diluted blood samples were overlaid onto 3 ml of Ficoll-Paque Plus (GE) placed in centrifuge tubes. The samples were centrifuged at 100 G at 18° C. for ten minutes. The middle layer containing mononuclear cells was transferred to a fresh centrifuge tube, and 45 ml of PBS was added thereto. The tube was centrifuged at 440 G at 18° C. for five minutes. The supernatant was removed. Again, 45 ml of PBS was added, and the tube was centrifuged at 440 G at 18° C. for five minutes. The supernatant was removed. The prepared mononuclear cells were incubated with Phycoerythrobilin (PE)-labeled anti-mouse PDGFRα antibody and Allophycocyanin (APC)-labeled anti-mouse CD44 antibody. Then, the abundance of PDGFRα and CD44 double-positive cells in the mononuclear cell fraction was assessed by flow cytometry (Facscan; Becton, Dickinson and Company).

Figure 37:
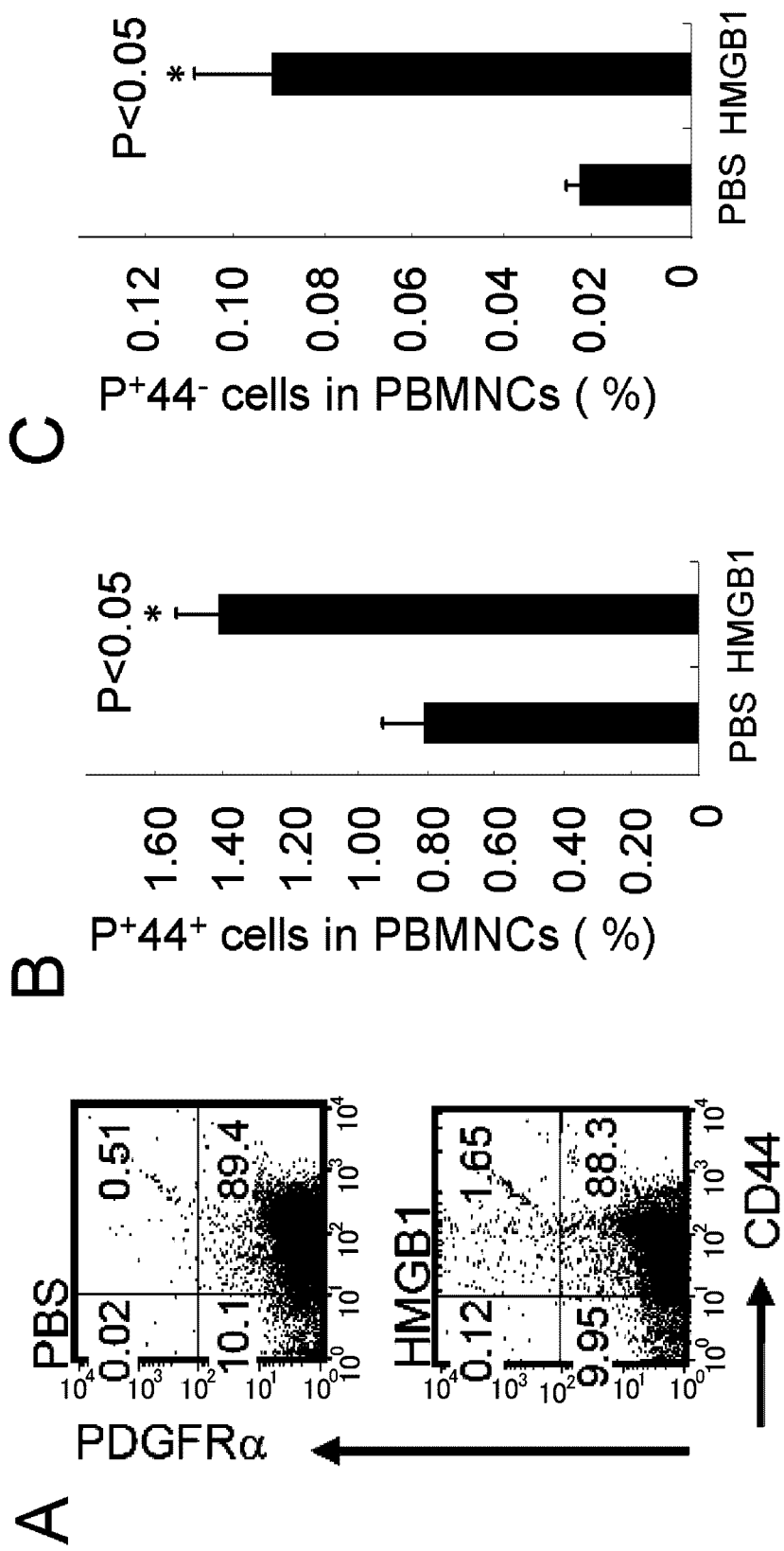

Results: PDGFRα and CD44 double-positive cells, and PDGFRα-positive, CD44-negative cells in the peripheral blood mononuclear cell fraction were demonstrated to be significantly increased 12 hours after HMGB1 administration (FIG. 37). Specifically, HMGB1 was demonstrated to have the activity of mobilizing PDGFRα-positive cells to peripheral blood from bone marrow. PDGFRα is known as a mesenchymal stem cell marker.

Discussion: PDGFRα and CD44 are known as surface markers of bone marrow mesenchymal stem cells, which are representative of bone marrow-derived pluripotent stem cells. Bone marrow mesenchymal stem cells are pluripotent stem cells capable of differentiating into nerve cells, epithelial cells, or such as well as osteocytes, chondrocytes, and adipocytes. Meanwhile, the skin pieces used in this experiment are in an ischemic condition. Thus, the tissues gradually necrotize and intracellular proteins such as nuclear proteins as well as cell surface proteins are released to the outside. HMGB1 is a protein contained in the skin extract. In skin grafting or the like, such proteins serve as a signal to mobilize bone marrow-derived tissue stem cells into grafted skin. It is thus speculated that functional skin regeneration is achieved in the skin graft due to reconstitution of epidermis, hypodermis, follicular tissues, or such stemmed from the bone marrow cells. Based on this experiment, the present invention for the first time successfully discovered that bone marrow-derived tissue stem cells are mobilized into peripheral blood circulation by intravenous administration of HMGB1 or skin extract as described above. This discovery enables new therapeutic methods for treating intractable diseases with tissue damages such as brain infarction, myocardial infarction, bone fracture, and cutaneous ulcer, which are based on mobilization of bone marrow-derived pluripotent stem cells into peripheral blood. In addition, cells mobilized to peripheral blood can be collected in the same way as conventional method for blood collection. Thus, the present invention enables simpler and safer methods for collecting bone marrow-derived tissue stem cells as compared to the conventional method for treating brain infarction in which cells are collected from the bone marrow.

INDUSTRIAL APPLICABILITY

The present invention enables collection of biologically functional cells in a minimally invasive manner, which was difficult previously. This can be expected to promote basic studies using biologically functional cells as well as regeneration medicine using the collected cells. Thus, the present invention is expected to be an innovative technique that provides patients suffering from intractable diseases with a new type of remedy. Furthermore, the vessels to be implanted in the body serve as a seed for the development of novel medical materials, and thus are expected to contribute to the industrial development in this field.

The invention claimed is:

1. A method for collecting bone-marrow-derived stem cells from a subject, wherein the method comprises:
   (I) implanting for at least 12 hours a vessel that contains a substance of any of (a) to (j) below, completely under the skin in subcutaneous adipose of the subject, to induce stem cells present in the bone marrow of the subject to migrate to the vessel implanted in subcutaneous tissue, wherein, as a result of the presence of the substance, stem cells present in bone marrow of the subject enter the vessel implanted in subcutaneous adipose:
   (a) an HMGB1 protein,
   (b) a cell that secretes an HMGB1,
   (c) an HMGB2 protein,
   (d) a cell that secretes an HMGB2,
   (e) an HMGB3 protein,
   (f) a cell that secretes an HMGB3 protein,
   (g) an S100A8 protein,
   (h) a cell that secretes an S100A8 protein,
   (i) an S100A9 protein,
   and (j) a cell that secretes an S100A9 protein,
   wherein the vessel is made from a material that is biologically hypoallergenic when implanted into the subject without any of (a) to (j), and wherein the vessel has one closed end to form an area therein to collect the bone-marrow-derived stem cells; and
   (II) collecting bone-marrow-derived stem cells from the vessel.

2. The method according to claim 1, wherein the bone-marrow-derived stem cells comprise bone marrow-derived mesenchymal stem cells, bone marrow stromal pluripotent stem cells, and/or bone marrow pluripotent stem cells.

3. The method according to claim 1, wherein the step of collecting bone-marrow-derived stem cells is performed using vacuum aspiration.

4. The method according to claim 1, wherein the vessel is implanted for at least one week.

5. The method according to claim 1, wherein the vessel is implanted for at least 10 days.

6. The method according to claim 1, wherein the vessel is implanted for at most two weeks.

7. The method according to claim 1, wherein the vessel is implanted for 12 hours to two weeks.

8. The method according to claim 1, wherein the vessel is implanted for one to two weeks.

9. The method according to claim 1, wherein the vessel is implanted for 10 days to two weeks.

10. A method for collecting bone-marrow-derived stem cells from a subject, wherein the method comprises:
    (I) implanting for at least 12 hours a vessel that contains a substance of any of (a) to (j) below, completely under the skin in subcutaneous adipose of the subject, to induce stem cells present in the bone marrow of the subject to migrate to the vessel implanted in subcutaneous tissue, wherein, as a result of the presence of the substance, stem cells present in bone marrow of the subject enter the vessel implanted in subcutaneous adipose:
    (a) an HMGB1 protein,
    (b) a cell that secretes an HMGB1,
    (c) an HMGB2 protein,
    (d) a cell that secretes an HMGB2,
    (e) an HMGB3 protein,
    (f) a cell that secretes an HMGB3 protein,
    (g) an S100A8 protein,
    (h) a cell that secretes an S100A8 protein,
    (i) an S100A9 protein, and
    (j) a cell that secretes an S100A9 protein,
    wherein the vessel is made from a material that is biologically hypoallergenic when implanted into the subject without any of (a) to (j), and wherein the vessel has one closed end to form an area therein to collect the bone-marrow-derived stem cells;
    (II) removing the vessel to outside the body from under the skin in subcutaneous adipose of the subject; and
    (III) collecting bone-marrow-derived stem cells from the vessel.

11. The method according to claim 10, wherein the bone-marrow-derived stem cells comprise bone marrow-derived mesenchymal stem cells, bone marrow stromal pluripotent stem cells, and/or bone marrow pluripotent stem cells.

12. The method according to claim 10, wherein the step of collecting bone-marrow-derived stem cells is performed using vacuum aspiration.

13. The method according to claim 10, wherein the vessel is implanted for at least one week.

14. The method according to claim 10, wherein the vessel is implanted for at least 10 days.

15. The method according to claim 10, wherein the vessel is implanted for at most two weeks.

16. The method according to claim 10, wherein the vessel is implanted for 12 hours to two weeks.

17. The method according to claim 10, wherein the vessel is implanted for one to two weeks.

18. The method according to claim 10, wherein the vessel is implanted for 10 days to two weeks.

19. A method for collecting bone-marrow-derived stem cells from a subject, wherein the method comprises:
    (I) implanting for at least 12 hours a vessel that contains a substance of any of (a) to (j) below, completely under the skin in subcutaneous adipose of the subject, to induce stem cells present in the bone marrow of the subject to migrate to the vessel implanted in subcutaneous tissue, wherein, as a result of the presence of the substance, stem cells present in bone marrow of the subject enter the vessel implanted in subcutaneous adipose:

(a) an HMGB1 protein,
(b) a cell that secretes an HMGB1,
(c) an HMGB2 protein,
(d) a cell that secretes an HMGB2,
(e) an HMGB3 protein,
(f) a cell that secretes an HMGB3 protein,
(g) an S100A8 protein,
(h) a cell that secretes an S100A8 protein,
(i) an S100A9 protein, and
(j) a cell that secretes an S100A9 protein,
wherein the vessel is made from a material that is biologically hypoallergenic when implanted into the subject without any of (a) to (j), and wherein the vessel has one closed end to form an area therein to collect the bone-marrow-derived stem cells; and
(II) collecting bone-marrow-derived stem cells from the vessel, which is still under the skin in subcutaneous adipose of the subject.

20. The method according to claim 19, wherein the bone-marrow-derived stem cells are a bone marrow-derived mesenchymal stem cell, a bone marrow stromal pluripotent stem cell, or a bone marrow pluripotent stem cell.

21. The method according to claim 19, wherein the step of collecting bone-marrow-derived stem cells is performed using vacuum aspiration.

22. The method according to claim 19, wherein the vessel is implanted for at least one week.

23. The method according to claim 19, wherein the vessel is implanted for at least 10 days.

24. The method according to claim 19, wherein the vessel is implanted for at most two weeks.

25. The method according to claim 19, wherein the vessel is implanted for 12 hours to two weeks.

26. The method according to claim 19, wherein the vessel is implanted for one to two weeks.

27. The method according to claim 19, wherein the vessel is implanted for 10 days to two weeks.

* * * * *